US012110526B2

(12) United States Patent
MacEachran et al.

(10) Patent No.: US 12,110,526 B2
(45) Date of Patent: *Oct. 8, 2024

(54) CELL-FREE PRODUCTION OF SUGARS

(71) Applicant: GreenLight Biosciences, Inc., Medford, MA (US)

(72) Inventors: Daniel MacEachran, Medford, MA (US); Drew S. Cunningham, Winchester, MA (US); William Jeremy Blake, Winchester, MA (US); Matthew Eduardo Moura, Cambridge, MA (US)

(73) Assignee: GreenLight Biosciences, Inc., Medford, MA (US)

( * ) Notice: Subject to any disclaimer, the term of this patent is extended or adjusted under 35 U.S.C. 154(b) by 11 days.

This patent is subject to a terminal disclaimer.

(21) Appl. No.: 17/507,939

(22) Filed: Oct. 22, 2021

(65) Prior Publication Data

US 2022/0282291 A1    Sep. 8, 2022

Related U.S. Application Data

(63) Continuation of application No. 16/892,696, filed on Jun. 4, 2020, now abandoned, which is a continuation of application No. 16/745,164, filed on Jan. 16, 2020, now Pat. No. 10,704,067, which is a continuation of application No. 16/395,548, filed on Apr. 26, 2019, now Pat. No. 10,577,635, which is a continuation of application No. 16/033,317, filed on Jul. 12, 2018, now Pat. No. 10,316,342, which is a continuation of application No. PCT/US2018/012516, filed on Jan. 5, 2018.

(60) Provisional application No. 62/538,181, filed on Jul. 28, 2017, provisional application No. 62/443,447, filed on Jan. 6, 2017.

(51) Int. Cl.
| | |
|---|---|
| C12P 19/02 | (2006.01) |
| C12N 9/10 | (2006.01) |
| C12N 9/90 | (2006.01) |
| C12N 9/92 | (2006.01) |
| C12N 15/52 | (2006.01) |
| C12P 19/14 | (2006.01) |

(52) U.S. Cl.
CPC ............ *C12P 19/02* (2013.01); *C12N 9/1051* (2013.01); *C12N 9/90* (2013.01); *C12N 9/92* (2013.01); *C12N 15/52* (2013.01); *C12P 19/14* (2013.01); *C12Y 204/01049* (2013.01); *C12Y 503/01* (2013.01); *C12Y 503/01009* (2013.01); *C12Y 504/02002* (2013.01); *C12Y 504/02005* (2013.01); *C12Y 504/02006* (2013.01)

(58) Field of Classification Search
CPC ... C12N 9/90; C12N 9/92; C12P 19/02; C12P 504/02005

See application file for complete search history.

(56) References Cited

U.S. PATENT DOCUMENTS

| | | | |
|---|---|---|---|
| 4,266,034 A | 5/1981 | Patel et al. | |
| 5,001,055 A | 3/1991 | Imahori et al. | |
| 6,168,931 B1 | 1/2001 | Swartz et al. | |
| 6,994,986 B2 | 2/2006 | Swartz et al. | |
| 7,041,479 B2 | 5/2006 | Swartz et al. | |
| 7,094,582 B2 | 8/2006 | Bao et al. | |
| 7,223,390 B2 | 5/2007 | Brown | |
| 7,226,767 B2 | 6/2007 | Maruyama et al. | |
| 7,312,049 B2 | 12/2007 | Calhoun et al. | |
| 7,338,789 B2 | 3/2008 | Swartz et al. | |
| 7,341,852 B2 | 3/2008 | Voloshin et al. | |
| 7,351,563 B2 | 4/2008 | Swartz et al. | |
| 7,579,005 B2 | 8/2009 | Keeler et al. | |
| 8,011,739 B2 | 9/2011 | Busley | |
| 8,030,035 B2 | 10/2011 | Oh et al. | |
| 8,859,247 B2 | 10/2014 | Koltermann et al. | |
| 8,916,358 B2 | 12/2014 | Swartz | |
| 8,956,833 B2 | 2/2015 | Swartz | |
| 9,217,166 B2 | 12/2015 | Kim et al. | |
| 9,469,861 B2 | 10/2016 | Blake et al. | |
| 9,611,487 B2 | 4/2017 | Blake et al. | |
| 9,637,746 B2 | 5/2017 | Klein-Marcuschamer | |
| 9,688,977 B2 | 6/2017 | Blake et al. | |
| 10,036,001 B2 | 7/2018 | Swartz | |
| 10,316,342 B2 * | 6/2019 | MacEachran | C12Y 504/02005 |
| 10,577,635 B2 * | 3/2020 | MacEachran | C12N 9/1051 |
| 10,704,067 B2 * | 7/2020 | MacEachran | C12N 9/1051 |
| 2002/0058303 A1 | 5/2002 | Swartz et al. | |
| 2002/0127633 A1 | 9/2002 | Dilley et al. | |
| 2002/0160459 A1 | 10/2002 | Berry et al. | |
| 2003/0022178 A1 | 1/2003 | Schneewind et al. | |
| 2003/0040086 A1 | 2/2003 | Dodge et al. | |

(Continued)

FOREIGN PATENT DOCUMENTS

| | | |
|---|---|---|
| CN | 102307987 A | 1/2012 |
| CN | 105219822 A | 1/2016 |

(Continued)

OTHER PUBLICATIONS

International Preliminary Report on Patentability for PCT/US2018/012516, mailed Jul. 18, 2019.

(Continued)

*Primary Examiner* — Tekchand Saidha

(74) *Attorney, Agent, or Firm* — Wolf, Greenfield & Sacks, P.C.

(57) ABSTRACT

Provided herein, in some embodiments, are systems, methods, and compositions (e.g., cells and cell lysates) for enzymatically converting a polymeric glucose carbohydrate (e.g., starch) to sugar.

20 Claims, 3 Drawing Sheets

Specification includes a Sequence Listing.

(56) References Cited

U.S. PATENT DOCUMENTS

| | | |
|---|---|---|
| 2003/0113778 A1 | 6/2003 | Schulte et al. |
| 2004/0002103 A1 | 1/2004 | Short |
| 2004/0038250 A1 | 2/2004 | Nunez et al. |
| 2004/0091976 A1 | 5/2004 | Deng et al. |
| 2004/0209321 A1 | 10/2004 | Swartz et al. |
| 2005/0054044 A1 | 3/2005 | Swartz et al. |
| 2005/0239174 A1 | 10/2005 | Bao et al. |
| 2006/0234358 A1 | 10/2006 | Anderlei et al. |
| 2006/0281148 A1 | 12/2006 | Swartz et al. |
| 2007/0111283 A1 | 5/2007 | Cannon et al. |
| 2007/0154983 A1 | 7/2007 | Calhoun et al. |
| 2007/0161092 A1 | 7/2007 | Townsend et al. |
| 2007/0202198 A1 | 8/2007 | Purcell |
| 2008/0021205 A1 | 1/2008 | Blau et al. |
| 2008/0131925 A1 | 6/2008 | Berk et al. |
| 2009/0042244 A1 | 2/2009 | Voloshin et al. |
| 2009/0053779 A1 | 2/2009 | Lee et al. |
| 2009/0124012 A1 | 5/2009 | Nikolsky et al. |
| 2009/0155867 A1 | 6/2009 | Soucaille |
| 2009/0275096 A1 | 11/2009 | Burgard et al. |
| 2009/0275097 A1 | 11/2009 | Sun et al. |
| 2009/0312539 A1 | 12/2009 | Gnanaprakasam et al. |
| 2009/0325245 A1 | 12/2009 | Soucaille et al. |
| 2010/0120105 A1 | 5/2010 | Anthony et al. |
| 2010/0143997 A1 | 6/2010 | Buelter et al. |
| 2010/0291653 A1 | 11/2010 | Ness et al. |
| 2011/0008867 A1 | 1/2011 | Zarur et al. |
| 2011/0099670 A1 | 4/2011 | Koops et al. |
| 2011/0124069 A1 | 5/2011 | Mampel et al. |
| 2011/0262946 A1 | 10/2011 | Roy et al. |
| 2011/0269198 A1 | 11/2011 | Klein-Marcuschamer |
| 2011/0275116 A1 | 11/2011 | Swartz |
| 2011/0312052 A1 | 12/2011 | Koltermann et al. |
| 2012/0052547 A1 | 3/2012 | Swartz |
| 2012/0070870 A1 | 3/2012 | Way et al. |
| 2013/0065878 A1 | 3/2013 | Blake et al. |
| 2014/0193869 A1 | 7/2014 | Blake et al. |
| 2014/0271559 A1 | 9/2014 | Baum et al. |
| 2015/0037868 A1 | 2/2015 | Blake et al. |
| 2015/0064751 A1 | 3/2015 | Swartz |
| 2015/0191753 A1 | 7/2015 | Swartz |
| 2016/0028101 A1 | 1/2016 | Zhang et al. |
| 2016/0115558 A1 | 4/2016 | Swartz |
| 2017/0096692 A1 | 4/2017 | Blake et al. |
| 2017/0159058 A1 | 6/2017 | Blake et al. |
| 2017/0247724 A1 | 8/2017 | Klein-Marcuschamer |
| 2017/0253866 A1 | 9/2017 | Blake et al. |
| 2017/0292138 A1 | 10/2017 | Blake et al. |
| 2018/0087045 A1 | 3/2018 | Blake et al. |
| 2018/0273985 A1 | 9/2018 | Blake |
| 2018/0320210 A1 | 11/2018 | MacEachran et al. |
| 2019/0017070 A1 | 1/2019 | Kim et al. |
| 2019/0136276 A1 | 5/2019 | Kim et al. |
| 2019/0249210 A1 | 8/2019 | MacEachran et al. |
| 2019/0249212 A1 | 8/2019 | Wichelecki et al. |
| 2020/0140907 A1 | 5/2020 | MacEachran et al. |
| 2021/0123082 A1 | 4/2021 | MacEachran et al. |
| 2022/0098630 A1 | 3/2022 | MacEachran et al. |

FOREIGN PATENT DOCUMENTS

| | | |
|---|---|---|
| CN | 105814191 A | 7/2016 |
| CN | 109196109 A | 1/2019 |
| CN | 110325641 A | 10/2019 |
| EP | 3 388 526 A1 | 10/2018 |
| JP | 2013-21967 A | 2/2013 |
| JP | 2015-530105 A | 10/2015 |
| KR | 2006/0059622 A | 6/2006 |
| KR | 10-2011-0035805 A | 4/2011 |
| KR | 10-1203586 B1 | 11/2012 |
| KR | 10-2014-0123284 A | 10/2014 |
| WO | WO 2000/055353 A1 | 9/2000 |
| WO | WO 2003/038117 A2 | 5/2003 |
| WO | WO 2005/030995 A1 | 4/2005 |
| WO | WO 2005/098048 A1 | 10/2005 |
| WO | WO 2006/001382 A1 | 1/2006 |
| WO | WO 2007/053655 A2 | 5/2007 |
| WO | WO 2007/110619 A1 | 10/2007 |
| WO | WO 2007/137144 A2 | 11/2007 |
| WO | WO 2008/002661 A2 | 1/2008 |
| WO | WO 2008/002663 A2 | 1/2008 |
| WO | WO 2008/002673 A2 | 1/2008 |
| WO | WO 2008/066583 A2 | 6/2008 |
| WO | WO 2008/088884 A2 | 7/2008 |
| WO | WO 2008/094546 A2 | 8/2008 |
| WO | WO 2010/046713 A2 | 4/2010 |
| WO | WO 2010/074760 A1 | 7/2010 |
| WO | WO 2010/077806 A1 | 7/2010 |
| WO | WO 2011/017560 A1 | 2/2011 |
| WO | WO 2011/072287 A2 | 6/2011 |
| WO | WO 2011/140516 A2 | 11/2011 |
| WO | WO 2012/030980 A1 | 3/2012 |
| WO | WO 2012/040414 A2 | 3/2012 |
| WO | WO 2010/053052 A1 | 4/2012 |
| WO | WO 2012/109274 A1 | 8/2012 |
| WO | WO 2012/135902 A1 | 10/2012 |
| WO | WO 2013/020118 A1 | 2/2013 |
| WO | WO 2014/151190 A1 | 9/2014 |
| WO | WO 2014/197655 A1 | 12/2014 |
| WO | WO 2014/197702 A1 | 12/2014 |
| WO | WO 2015/021058 A2 | 2/2015 |
| WO | WO 2016/160936 A1 | 10/2016 |
| WO | WO 2017/002978 A1 | 1/2017 |
| WO | WO 2017/059278 A1 | 4/2017 |
| WO | WO 2018/112139 A1 | 6/2018 |
| WO | WO 2018/129275 A1 | 7/2018 |
| WO | WO 2018/169957 A1 | 9/2018 |
| WO | WO 2020/132027 A2 | 6/2020 |

OTHER PUBLICATIONS

International Search Report and Written Opinion for PCT/US2018/012516, mailed Apr. 9, 2018.

Extended European Search Report for EP 18736632.3, mailed Sep. 7, 2020.

International Search Report and Written Opinion for PCT/US2019/067113, mailed Jun. 25, 2020.

Invitation to Pay Additional Fees for PCT/US2019/067113, mailed Apr. 17, 2020.

International Preliminary Report on Patentability for PCT/US2019/067113, mailed Jul. 1, 2021.

Beaucage et al., Deoxynucleoside phosphoramidites—A new class of key intermediates for deoxypolynucleotide synthesis. Tetra Lett. 1981;22(20):1859-62.

Bhuiyan et al., Characterization of a hyperthermostable glycogen phosphorylase from Aquifex aeolicus expressed in *Escherichia coli*. J Mol Catalysis B:Enzy. Jun. 2, 2003;22(3-4):173-180.

Boiteux et al., Design of glycolysis. Philos Trans R Soc Lond B Biol Sci. Jun. 26, 1981;293(1063):5-22.

Bongaerts et al., Metabolic engineering for microbial production of aromatic amino acids and derived compounds. Metab Eng. Oct. 2001;3(4):289-300.

Boyer et al., Cell-free synthesis and maturation of [FeFe] hydrogenases. Biotechnol Bioeng. Jan. 1, 2008;99(1):59-67.

Bujara et al., Exploiting cell-free systems: Implementation and debugging of a system of biotransformations. Biotechnol Bioeng. Jun. 15, 2010;106(3):376-89. doi: 10.1002/bit.22666.

Bujara et al., Optimization of a blueprint for in vitro glycolysis by metabolic real-time analysis. Nat Chem Biol. May 2011;7(5):271-7. doi: 10.1038/nchembio.541. Epub Mar. 20, 2011.

Calhoun et al., An economical method for cell-free protein synthesis using glucose and nucleoside monophosphates. Biotechnol Prog. Jul.-Aug.2005;21(4):1146-53.

Calhoun et al., Energizing cell-free protein synthesis with glucose metabolism. Biotechnol Bioeng. Jun. 5, 2005;90(5):606-13.

Calhoun et al., Energy systems for ATP regeneration in cell-free protein synthesis reactions. Methods in Molecular Biology. In vitro transcription and translation protocols. 2007;375(2):3-17.

Calhoun et al., Total amino acid stabilization during cell-free protein synthesis reactions. J Biotechnol. May 17, 2006;123(2):193-203. Epub Jan. 26, 2006.

(56) References Cited

OTHER PUBLICATIONS

Endoh et al., Cell-free protein synthesis at high temperatures using the lysate of a hyperthermophile. J Biotechnol. Nov. 1, 2006;126(2):186-95. Epub May 30, 2006.

Flores et al., Pathway engineering for the production of aromatic compounds in *Escherichia coli*. Nat Biotechnol. May 1996;14(5):620-3.

Flores et al., Growth-rate recovery of *Escherichia coli* cultures carrying a multicopy plasmid, by engineering of the pentose-phosphate pathway. Biotechnol Bioeng. Aug. 20, 2004;87(4):485-94.

Goerke et al., Cell-free metabolic engineering promotes high-level production of bioactive Gaussia princeps luciferase.Metab Eng. May-Jul. 2008;10(3-4):187-200. doi: 10.1016/j.ymben.2008.04.001. Epub May 2, 2008.

Goerke et al., Development of cell-free protein synthesis platforms for disulfide bonded proteins. Biotechnol Bioeng. Feb. 1, 2008;99(2):351-67. Epub Jul. 11, 2007.

Goody, A simple and rapid method for the synthesis of nucleoside 5'-monophosphates enriched with 170 or 180 on the phosphate group. Anal Biochem. Jan. 15, 1982;119(2):322-4.

Hansen et al., Novel type of glucose-6-phosphate isomerase in the hyperthermophilic archaeon Pyrococcus furiosus. J Bacteriol. 2001;183(11):3428-3435. doi:10.1128/JB.183.11.3428-3435.2001.

Hethke et al., Cell-free transcription at 95 degrees: thermostability of transcriptional components and DNA topology requirements of Pyrococcus transcription. Genetics. Aug. 1999;152(4):1325-33.

Jang et al., Sugar sensing in higher plants. Plant Cell. Nov. 1994;6(11):1665-79.

Jenny et al., A critical review of the methods for cleavage of fusion proteins with thrombin and factor Xa. Protein Expr Purif. Sep. 2003;31(1):1-11.

Jermutus et al., Recent advances in producing and selecting functional proteins by using cell-free translation. Curr Opin Biotechnol. Oct. 1998;9(5):534-48.

Jewett et al., An integrated cell-free metabolic platform for protein production and synthetic biology. Mol Syst Biol. 2008;4:220. Epub Oct. 14, 2008.

Jewett et al., Mimicking the *Escherichia coli* cytoplasmic environment activates long-lived and efficient cell-free protein synthesis. Biotechnol Bioeng. Apr. 5, 2004;86(1):19-26.

Jonnalagadda et al., Flux regulation in glycogen-induced oscillatory glycolysis in cell-free extracts of *Saccharomyces carlsbergensis*. Biosystems. 1982;15(1):49-58.

Kim et al., Prolonged cell-free protein synthesis using dual energy sources: Combined use of creatine phosphate and glucose for the efficient supply of ATP and retarded accumulation of phosphate. Biotechnol Bioeng. Aug. 15, 2007;97(6):1510-5.

Kim et al., Regeneration of adenosine triphosphate from glycolytic intermediates for cell-free protein synthesis.Biotechnol Bioeng. Aug. 20, 2001;74(4):309-16.

Knapp et al., Cell-free production of active *E. coli* thioredoxin reductase and glutathione reductase. FEBS Lett. Feb. 13, 2004;559(1-3):66-70.

Lee et al., Fermentative production of thymidine by a metabolically engineered *Escherichia coli* strain. Appl Environ Microbiol. Apr. 2009;75(8):2423-32. Epub Feb. 27, 2009.

Lee et al., Systems metabolic engineering of *Escherichia coli* for L-threonine production. Mol Syst Biol. 2007;3:149. Epub Dec. 4, 2007.

Li et al., Improved cell-free RNA and protein synthesis system. PLoS One. Sep. 2, 2014;9(9):e106232. doi: 10.1371/journal.pone.0106232. eCollection 2014.

Li et al., Rational strain improvement for enhanced clavulanic acid production by genetic engineering of the glycolytic pathway in *Streptomyces clavuligerus*. Metab Eng. May 2006;8(3):240-52. Epub Mar. 10, 2006.

Liu et al., Combined biosynthetic pathway for de novo production of UDP-galactose: catalysis with multiple enzymes immobilized on agarose beads. Chembiochem. Apr. 2, 2002;3(4):348-55.

Liu et al., Streamlining *Escherichia coli* S30 extract preparation for economical cell-free protein synthesis. Biotechnol Prog. Mar.-Apr. 2005;21(2):460-5.

Meynial-Salles et al., New tool for metabolic pathway engineering in *Escherichia coli*: one-step method to modulate expression of chromosomal genes. Appl Environ Microbiol. Apr. 2005;71(4):2140-4.

Michel-Reydellet et al., Amino acid stabilization for cell-free protein synthesis by modification of the *Escherichia coli* genome. Metab Eng. Jul. 2004;6(3):197-203.

Ninh et al., Development of a continuous bioconversion system using a thermophilic whole-cell biocatalyst. Appl Environ Microbiol. Mar. 2013;79(6):1996-2001. doi: 10.1128/AEM.03752-12. Epub Jan. 18, 2013. PMID: 23335777; PMCID: PMC3592215.

Noireaux et al., Principles of cell-free genetic circuit assembly. Proc Natl Acad Sci U S A. Oct. 28, 2003;100(22):12672-7. Epub Oct. 14, 2003.

Scopes, Glycolysis in cell-free systems. New beer in an old bottle: Eduard Buchner and the growth of biochemical knowledge. Ed A. Cornish-Bowden. 1997;151-8.

Spirin, High-throughput cell-free systems for synthesis of functionally active proteins.Trends Biotechnol. Oct. 2004;22(10):538-45. With Supplementary data.

Swartz et al., Advances in *Escherichia coli* production of therapeutic proteins. Curr Opin Biotechnol. Apr. 2001;12(2):195-201.

Swartz, Developing cell-free biology for industrial applications. J Ind Microbiol Biotechnol. Jul. 2006;33(7):476-85. Epub May 9, 2006. Review.

Swartz, Transforming biochemical engineering with cell-free biology. AIChE J. 2012;58(1):5-13.

Swartz, Universal cell-free protein synthesis. Nat Biotechnol. Aug. 2009;27(8):731-2. doi: 10.1038/nbt0809-731.

Voloshin et al., Efficient and scalable method for scaling up cell free protein synthesis in batch mode. Biotechnol Bioeng. Aug. 20, 2005;91(4):516-21.

Welch et al., Studies on cell-free metabolism: Ethanol production by a yeast glycolytic system reconstituted from purified enzymes. J Biotechnol. 1985;2:257-73.

Wuu et al., High yield cell-free production of integral membrane proteins without refolding or detergents. Biochim Biophys Acta. May 2008;1778(5):1237-50. doi: 10.1016/j.bbamem.2008.01.023. Epub Feb. 11, 2008.

Zawada et al., Effects of growth rate on cell extract performance in cell-free protein synthesis. Biotechnol Bioeng. Jul. 5, 2006;94(4):618-24.

Zawada et al., Maintaining rapid growth in moderate-density *Escherichia coli* fermentations. Biotechnol Bioeng. Feb. 20, 2005;89(4):407-15.

Zhu et al., A high-energy-density sugar biobattery based on a synthetic enzymatic pathway. Nat Commun. 2014;5:3026. doi: 10.1038/ncomms4026.

Chan et al., Crystal structures of D-psicose 3-epimerase from Clostridium cellulolyticum H10 and its complex with ketohexose sugars. Protein Cell. Feb. 2012;3(2):123-31. doi: 10.1007/s13238-012-2026-5. Epub Mar. 17, 2012.

Li et al., Biosynthesis of rare hexoses using microorganisms and related enzymes. Beilstein J Org Chem. Nov. 12, 2013;9:2434-45. doi: 10.3762/bjoc.9.281.

Zhang et al., Recent advances in d-allulose: Physiological functionalities, applications, and biological production. Trends in Food Science & Technology. Aug. 2016;54:127-137.

Invitation to Pay Additional Fees for PCT/US2022/080143, mailed Feb. 10, 2023.

International Search Report and Written Opinion for PCT/US2022/080143, mailed Apr. 24, 2023.

Restiawaty et al., Feasibility of thermophilic adenosine triphosphate-regeneration system using Thermus thermophilus polyphosphate kinase. Proc Biochem. Sep. 2011;46(9):1747-52. doi: 10.1016/j.procbio.2011.05.021.

Zhang et al., Progress in Researches on D-psicose, a New Sweetener. Food and Fermentation Industries. Dec. 31, 2008;34(12):125-9.

* cited by examiner

CELL-FREE PRODUCTION OF SUGARS

RELATED APPLICATIONS

This application is a continuation of U.S. application Ser. No. 16/892,696, filed Jun. 4, 2020, which is a continuation of U.S. application Ser. No. 16/745,164, filed Jan. 16, 2020, which is a continuation of U.S. application Ser. No. 16/395,548, filed Apr. 26, 2019, which is a continuation of U.S. application Ser. No. 16/033,317, filed Jul. 12, 2018, which is a continuation of international application number PCT/US2018/012516, filed Jan. 5, 2018, which claims priority under 35 U.S.C. § 119(e) to U.S. provisional application 62/443,447, filed Jan. 6, 2017, and U.S. provisional application 62/538,181, filed Jul. 28, 2017; the entire contents of each of which are incorporated herein by reference in their entireties.

BACKGROUND

Existing technologies for the conversion of starch to simple sugars employ multiple biotransformation reactions, with extensive purification processes following each biotransformation. While the biotransformation processes are relatively inexpensive, owing to the application of immobilized enzymes and continuous production systems, the downstream processing impacts cost dramatically.

SUMMARY

Provided herein are cell free systems, methods, compositions and kits for the enzymatic conversion of polymeric glucose, such as starch (e.g., amylose and/or amylopectin), glycogen, or any partially hydrolyzed derivative thereof such as maltodextrin, or cellodextrin (which may be used interchangeably with the term cellulose) to pentose (e.g., ribose, arabinose, or xylulose) or hexose (e.g., allulose, glucose, or fructose) sugars. The methods of the present disclosure implement sugar production pathways in cell-free reactions (e.g., a one-pot (single) cell-free reaction), to convert starch and/or cellulose/cellodextrin to hexose and/or pentose sugars. Unlike processes that typically involve phosphorylation of substrates such as glucose to glucose 6-phosphate and employ high-energy phosphate sources such as ATP and phosphoenoylpyruvate, the processes described herein typically replace high energy phosphate sources with, for example, inexpensive inorganic phosphate ($P_i$). In some embodiments, an α-glucan phosphorylase (also referred to as a starch phosphorylase) (EC 2.4.1.1) is used to convert starch to glucose 1-phosphate, which is then converted to glucose 6-phosphate via a phosphoglucomutase (EC 5.4.2.2, 5.4.2.5, or 5.4.2.6). In other embodiments, a cellodextrin phosphorylase (also referred to as cellulose phosphorylase or β-(1-4) glucan phosphorylase) (EC 2.4.1.49) is used to convert cellulose/cellodextrin to glucose 1-phosphate, which is then converted to glucose 6-phosphate via a phosphoglucomutase (EC 5.4.2.2, 5.4.2.5, or 5.4.2.6). Subsequent enzymatic reaction(s) of a particular sugar production pathway as provided herein are largely product specific. A sugar phosphatase (EC 3.1.3.–) is used to convert the final product. Thus, the reaction thermodynamics—phosphorylation of the substrate to desphosphorylation of the product—favor the product.

Further, the enzymatic conversion reactions described herein are essentially irreversible, thus supporting high yields of the desired hexose and pentose sugars. By contrast, typical biotransformation methods for converting starch or cellulose/cellodextrin to allulose, for example, employ three distinct processes, two of which are reversible, with the final concentration of the product being governed by the thermodynamics of the enzymes being utilized. Starch, for example, is converted to glucose, glucose is isomerized to fructose, and fructose is epimerized to allulose. The isomerization of glucose to fructose has a yield of approximately 45%, thus significant downstream processing is required to yield a pure product and recycle uncatalyzed substrate. Similarly, the epimerization of fructose to allulose has a yield of ~20%, again requiring substantial downstream processing to yield a purified product and recycle uncatalyzed substrate. The ability to directly transform starch to the product of interest in the cell-free systems described herein reduces cost by reducing downstream processing and the loss of substrate.

Advantageously, many of the enzymes used in the processes provided herein are thermostable, which (1) enables thermal inactivation of deleterious activities contained within cellular lysates in which the conversion process is performed, and (2) decreases the chances of microbial contamination negatively impacting production runs. The enzymes of these conversion pathways can be isolated from thermophilic, mesophilic, or psychrophilic organisms and/or, in some embodiments, can be engineered to increase (or decrease) the thermostability of the enzymes. A thermophilic organism (thermophile) thrives at high temperatures, between 41° C. and 122° C. (106° F. and 252° F.). A mesophilic organism (mesophile) thrives at moderate temperatures, between 20° C. and 45° C. (68° F. and 113° F.). A psychrophilic organism (psychrophile) thrives at cold temperatures, between –20° C. and 10° C. (–4° F. and 50° F.).

Thus, some aspects of the present disclosure provide methods for producing a sugar (e.g., allulose, glucose, fructose, sorbitol, ribulose, ribose, and/or arabinose), the method comprising (a) culturing at least two cell populations, wherein cells of each population are engineered to express at least one thermostable enzyme of a sugar production pathway described herein to produce at least two cultured populations of cells expressing different enzymes, (b) lysing cells of the at least two cultured populations to produce at least two cell lysates, (c) combining the at least two cell lysates to produce a cell lysate mixture that comprises thermostable enzymes of the sugar production pathway, (d) heating the cell lysate mixture to a temperature that inactivates undesired native enzymatic activities but does not inactivate the thermostable enzymes of step (c) to produce a heat-inactivated lysate, and (e) incubating the reaction mixture in the presence of a substrate (e.g., starch, glycogen, or any partially hydrolyzed derivative thereof) and a phosphate source (e.g., inorganic phosphate) to produce the sugar.

In some embodiments, a cell-free method for producing a sugar (e.g., allulose, glucose, fructose, sorbitol, ribulose, ribose, and/or arabinose) comprises (a) culturing at least two cell populations, wherein cells of each population are engineered to express at least one enzyme of a sugar production pathway described herein to produce at least two cultured populations of cells expressing different enzymes wherein at least one of the enzymes of the sugar production pathway is thermostable, (b) lysing cells of the at least two cultured populations to produce at least two cell lysates, (c) optionally heating one or more of the cell lysates of step (b) to a temperature that inactivates undesired native enzymatic activities but does not inactivate the thermostable enzyme(s) of step (a) to produce a heat-inactivated lysate, (d) combining the cell lysates of step (b) and (c) to produce a cell lysate mixture that comprises the enzymes of the sugar production pathway, wherein at least one of the foregoing enzymes is thermostable, and (e) incubating the reaction mixture in the presence of a substrate (e.g., starch, glycogen, or any partially hydrolyzed derivative thereof) and a phosphate source (e.g., inorganic phosphate) to produce the sugar.

In some embodiments, a cell-free method for producing a sugar (e.g., allulose, glucose, fructose, sorbitol, ribulose, ribose, and/or arabinose) comprises (a) culturing at least two cell populations, wherein cells of each population are engineered to express at least one thermostable enzyme of a sugar production pathway described herein to produce at least two cultured populations of cells expressing different enzymes, (b) lysing cells of the at least two cultured populations to produce at least two cell lysates, (c) combining the at least two cell lysates to produce a cell lysate mixture, (d) heating the cell lysate mixture to a temperature that inactivates undesired native enzymatic activities but does not inactivate the thermostable enzymes of step (a) to produce a heat-inactivated lysate, (e) adding to the heat-inactivated lysate at least one purified enzyme of the sugar production pathway, and (f) incubating the reaction mixture in the presence of a substrate (e.g., starch, glycogen, or any partially hydrolyzed derivative thereof) and a phosphate source (e.g., inorganic phosphate) to produce the sugar.

In some embodiments, a cell-free method for producing a sugar (e.g., allulose, glucose, fructose, sorbitol, ribulose, ribose, and/or arabinose) comprises (a) culturing at least two cell populations, wherein cells of each population are engineered to express at least one enzyme of a sugar production pathway described herein to produce at least two cultured populations of cells expressing different enzymes, wherein at least one of the foregoing enzymes is thermostable, (b) lysing cells of the at least two cultured populations to produce at least two cell lysates, (c) optionally heating one or more of the cell lysates of step (b) to a temperature that inactivates undesired native enzymatic activities but does not inactivate the thermostable enzymes of step (a) to produce a heat-inactivated lysate, (d) combining the cell lysates of step (b) and (c) to produce a cell lysate mixture, (e) adding to the cell lysate mixture at least one purified enzyme of the sugar production pathway, and (f) incubating the reaction mixture in the presence of a substrate (e.g., starch, glycogen, or any partially hydrolyzed derivative thereof) and a phosphate source (e.g., inorganic phosphate) to produce the sugar.

Some aspects of the present disclosure provide cell-free methods for producing allulose, the methods comprising (a) culturing cells engineered to express a α-glucan phosphorylase (also referred to as a starch phosphorylase), a phosphoglucomutase, a phosphoglucoisomerase, an allulose 6-phosphate epimerase, and an allulose 6-phosphate phosphatase to produce cultured cells that express the enzymes, wherein at least one of the foregoing enzymes is thermostable, (b) lysing the cultured cells to produce a cell lysate, (c) heating the cell lysate to a temperature that inactivates native enzymatic activity but does not inactivate the thermostable enzyme(s) of step (a) to produce a heat-inactivated lysate, and (d) incubating the heat-inactivated lysate in the presence of starch, glycogen, or any partially hydrolyzed derivative thereof and a phosphate source (e.g., inorganic phosphate) to produce allulose. In some embodiments, at least one purified enzyme is added to the cell lysate before or after step (c). It should be understood that the cells may be lysed by any means, including mechanical, chemical, enzymatic, osmotic or thermal lysis. Thus, the lysing step and the heating (heat inactivation) step may be combined as a single step of heating the cells to a temperature that lyses the cells and inactivates native enzymatic activity.

In some embodiments, the cell-free methods comprise (a) culturing at least two cell populations, wherein cells of each population are engineered to express at least one enzyme selected from the group consisting of α-glucan phosphorylases, phosphoglucomutases, phosphoglucoisomerases, allulose 6-phosphate epimerases, and allulose 6-phosphate phosphatases to produce at least two cultured populations of cells expressing different enzymes, wherein at least one of foregoing enzymes is thermostable, (b) lysing cells of the at least two cultured populations to produce at least two cell lysates, (c) combining the at least two cell lysates to produce a cell lysate mixture that comprises a α-glucan phosphorylase, a phosphoglucomutase, a phosphoglucoisomerase, an allulose 6-phosphate epimerase, and an allulose 6-phosphate phosphatase, (d) heating the cell lysate mixture to a temperature that inactivates native enzymatic activity but does not inactivate the thermostable enzyme(s) of step (c) to produce a heat-inactivated lysate, and (e) incubating the reaction mixture in the presence of a starch, glycogen, or any partially hydrolyzed derivative thereof and a phosphate source (e.g., inorganic phosphate) to produce allulose.

In other embodiments, the cell-free methods comprise (a) culturing at least two cell populations, wherein cells of each population are engineered to express at least one enzyme selected from the group consisting of α-glucan phosphorylases, phosphoglucomutases, phosphoglucoisomerases, allulose 6-phosphate epimerases, and allulose 6-phosphate phosphatases to produce at least two cultured populations of cells expressing different enzymes, wherein at least one of the foregoing enzymes is thermostable, (b) lysing cells of the at least two cultured populations to produce at least two cell lysates, (c) combining the at least two cell lysates to produce a cell lysate mixture (d) heating the cell lysate mixture to a temperature that inactivates native enzymatic activity but does not inactivate the thermostable enzyme(s) of step (a) to produce a heat-inactivated lysate, (e) adding to the heat-inactivated lysate at least one purified enzyme selected from the group consisting of α-glucan phosphorylases, phosphoglucomutases, phosphoglucoisomerases, allulose 6-phosphate epimerases, and allulose 6-phosphate phosphatases to produce a reaction mixture comprising a α-glucan phosphorylase, a phosphoglucomutase, a phosphoglucoisomerase, an allulose 6-phosphate epimerase, and an allulose 6-phosphate phosphatase, and (f) incubating the reaction mixture in the presence of a starch, glycogen, or any partially hydrolyzed derivative thereof and a phosphate source (e.g., inorganic phosphate) to produce allulose.

In some aspects of the present disclosure, it may be preferable to use cellulose/cellodextrin as a starting substrate. Thus, some aspects of the present disclosure provide cell-free methods for producing allulose, the methods comprising (a) culturing cells engineered to express a cellodextrin phosphorylase, a phosphoglucomutase, a phosphoglucoisomerase, an allulose 6-phosphate epimerase, and an allulose 6-phosphate phosphatase to produce cultured cells that express the enzymes, wherein at least one of the foregoing enzymes is thermostable, (b) lysing the cultured cells to produce a cell lysate, (c) heating the cell lysate to a temperature that inactivates native enzymatic activity but does not inactivate the thermostable enzyme(s) of step (a) to produce a heat-inactivated lysate, and (d) incubating the heat-inactivated lysate in the presence of cellodextrin and a phosphate source (e.g., inorganic phosphate) to produce allulose.

In some embodiments, the cell-free methods comprise (a) culturing at least two cell populations, wherein cells of each population are engineered to express at least one enzyme selected from the group consisting of cellodextrin phosphorylases, phosphoglucomutases, phosphoglucoisomerases, allulose 6-phosphate epimerases, and allulose 6-phosphate phosphatases to produce at least two cultured populations of cells expressing different enzymes, wherein at least one of foregoing enzymes is thermostable, (b) lysing cells of the at least two cultured populations to produce at least two cell lysates, (c) combining the at least two cell lysates to produce a cell lysate mixture that comprises a cellodextrin phosphorylase, a phosphoglucomutase, a phosphoglucoisomerase, an allulose 6-phosphate epimerase, and an allulose 6-phosphate phosphatase, (d) heating the cell lysate mixture to a temperature that inactivates native enzymatic activity but does not inactivate the thermostable enzyme(s) of step (c) to produce a heat-inactivated lysate, and (e) incubating the reaction mixture in the presence of a cellodextrin and a phosphate source (e.g., inorganic phosphate) to produce allulose.

In other embodiments, the cell-free methods comprise (a) culturing at least two cell populations, wherein cells of each population are engineered to express at least one enzyme selected from the group consisting of cellodextrin phosphorylases, phosphoglucomutases, phosphoglucoisomerases, allulose 6-phosphate epimerases, and allulose 6-phosphate phosphatases to produce at least two cultured populations of cells expressing different enzymes, wherein at least one of the foregoing enzymes is thermostable, (b) lysing cells of the at least two cultured populations to produce at least two cell lysates, (c) combining the at least two cell lysates to produce a cell lysate mixture (d) heating the cell lysate mixture to a temperature that inactivates native enzymatic activity but does not inactivate the thermostable enzyme(s) of step (a) to produce a heat-inactivated lysate, (e) adding to the heat-inactivated lysate at least one purified enzyme selected from the group consisting of cellodextrin phosphorylases, phosphoglucomutases, phosphoglucoisomerases, allulose 6-phosphate epimerases, and allulose 6-phosphate phosphatases to produce a reaction mixture comprising a cellodextrin phosphorylase, a phosphoglucomutase, a phosphoglucoisomerase, an allulose 6-phosphate epimerase, and an allulose 6-phosphate phosphatase, and (f) incubating the reaction mixture in the presence of a cellodextrin and a phosphate source (e.g., inorganic phosphate) to produce allulose.

The cell-free production of other sugars, such as glucose, fructose, mannose, sorbitol, ribulose, ribose, and arabinose is also encompassed by the present disclosure.

In some embodiments, the presented sugar pathways require the balancing of energetic cofactors, such as NADH, NADPH, $NAD^+$, or $NADP^+$. This can be done through cofactor regeneration systems. In these instances, NADH and NADPH are referred to as "reduced cofactors" or "reducing agents," and $NAD^+$ and $NADP^+$ are referred to as "oxidized cofactors" or "oxidizing agents." For instances with excess reducing agents, an NAD(P)H oxidase (EC #1.6.3.1, 1.6.3.2, 1.6.2.3, or 1.6.3.4), can be used to burn excess reduced cofactors producing either $H_2O_2$, $O^-_2$, or $H_2O$, depending on the type of oxidase. When producing $H_2O_2$ and $O_2^-$, which can cause detrimental damage to the lysate, superoxide dismutase (EC #1.15.1.1) and/or catalase (EC #1.11.1.6) can be used in tandem to convert the harmful species to $H_2O$ and $O_2$. For instances with excess oxidizing agents, a cofactor regeneration system can be used to reduce the oxidized cofactors back to their reduced forms. Some examples include the use of formate dehydrogenase (EC #1.2.1.2) to oxidize formate to $CO_2$ while reducing $NAD(P)^+$ NAD(P)H, or the use of phosphonate dehydrogenase (EC #1.20.1.1) or sulfite oxidoreductase (EC #1.8.1.2) to oxidize the respective inorganic salts to phosphate and sulfate, resulting in reduced NAD(P)H.

Also provided herein are engineered cells, cell lysates, and reaction mixtures comprising enzymes, such as thermostable enzymes, used for the production of a particular sugar of interest (e.g., allulose, glucose, fructose, sorbitol, ribulose, ribose, and/or arabinose).

DETAILED DESCRIPTION

Figure 1:
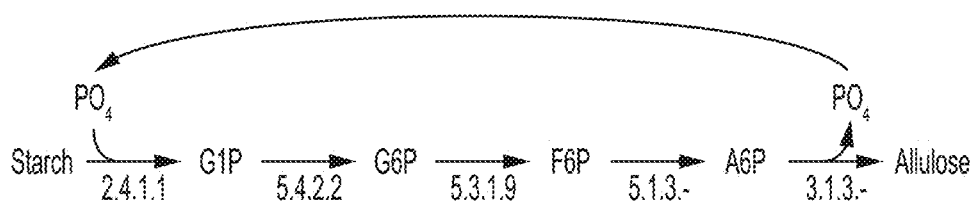
FIG. 1 is a schematic of an enzymatic pathway for the conversion of starch to allulose. The meaning of the abbreviations is as follows: G1P=glucose 1-phosphate, G6P=glucose 6-phosphate, F6P=fructose 6-phosphate, A6P=allulose 6-phosphate, and $PO_4$=inorganic phosphate.

Described herein are enzymatic pathways used for the conversion of starch (e.g., amylose or amylopectin) or cellulose/cellodextrin to pentose (e.g., ribose, arabinose, or xylulose) and/or hexose (e.g., allulose, glucose, or fructose) sugars. The enzymatic pathways utilize at least one α-glucan phosphorylase (also referred to as a starch phosphorylase) (EC 2.4.1.1) or at least one cellodextrin phosphorylase (also referred to as cellulose phosphorylase) (EC 2.4.1.49), at least one phosphoglucomutase (EC 5.4.2.2, 5.4.2.5, or 5.4.2.6) and any number of isomerases, epimerases, and/or sugar phosphatases, depending on the final product. In some embodiments, the enzymes or a portion of the enzymes are thermostable. These thermostable enzymes can withstand the heating step of the sugar production process that inactivate deleterious activities contained within cellular lysates in which the conversion processes are performed. This heat inactivation step decreases the chances of microbial contamination negatively impacting production runs.

Thus, the present disclosure provides, in some embodiments, highly-efficient and cost-effective methods, compositions, and systems for producing sugars such as hexose and pentose sugars. Non-limiting examples of sugar production pathways and pathway enzymes are provided in Table 1 below.

TABLE 1

Summary of Exemplary Pathway Enzymes

| Pathway | Substrate | Enzymes |
| --- | --- | --- |
| glucose production | α(1-4) or β(1-4) glucans | α- or β-(1-4) glucan phosphorylase (EC 2.4.1.1, 2.4.1.49), phosphoglucomutase (EC 5.4.2.2, 5.4.2.5, 5.4.2.6), glucose 6-phosphate phosphatase (EC 3.1.3.9, 3.1.3.58) |
| glucose production | α(1-4) or β(1-4) glucans | α- or β-(1-4) glucan phosphorylase (EC 2.4.1.1, 2.4.1.49), glucose 1-phosphate phosphatase (EC 3.1.3.10) |
| fructose production | α(1-4) or β(1-4) glucans | α- or β-(1-4) glucan phosphorylase (EC 2.4.1.1, 2.4.1.49), phosphoglucomutase (EC 5.4.2.2, 5.4.2.5, 5.4.2.6), phosphoglucoisomerase (EC 5.3.1.9), and fructose 6-phosphate phosphatase (EC 3.1.3.-, 3.1.3.58) |
| allulose production | α(1-4) or β(1-4) glucans | α- or β-(1-4) glucan phosphorylase (EC 2.4.1.1, 2.4.1.49), phosphoglucomutase (EC 5.4.2.2, 5.4.2.5, 5.4.2.6), phosphoglucoisomerase (EC 5.3.1.9), allulose 6-phosphate epimerase (EC 5.1.3.-), and allulose 6-phosphate phosphatase (EC 3.1.3.-, 3.1.3.58) |
| sorbitol production | α(1-4) or β(1-4) glucans | α- or β-(1-4) glucan phosphorylase (EC 2.4.1.1, 2.4.1.49), phosphoglucomutase (EC 5.4.2.2, 5.4.2.5, 5.4.2.6), aldose dehydrogenase (EC 1.1.1.200), and sorbitol-6-phosphate phosphatase (EC 3.1.3.50, 3.1.3.58) |
| sorbitol production | α(1-4) or β(1-4) glucans | α- or β-(1-4) glucan phosphorylase (EC 2.4.1.1, 2.4.1.49), phosphoglucomutase (EC 5.4.2.2, 5.4.2.5, 5.4.2.6), phosphoglucoisomerase (EC 5.3.1.9) sorbitol-6-phosphate 2-dehydrogenase (EC 1.1.1.140) sorbitol-6-phosphate phosphatase (EC 3.1.3.50, 3.1.3.58) |
| ribulose production | α(1-4) or β(1-4) glucans | α- or β-(1-4) glucan phosphorylase (EC 2.4.1.1, 2.4.1.49), phosphoglucomutase (EC 5.4.2.2, 5.4.2.5, 5.4.2.6), glucose 6-phosphate dehydrogenase (EC 1.1.1.49, 1.1.1.388, 1.1.1.363), 6-phosphogluconolactonase (EC 3.1.1.31), 6-phosphogluconate dehydrogenase (EC 1.1.1.44, 1.1.1.343, 1.1.1.351), and ribulose 5-phosphate phosphatase (EC 3.1.3.-, 3.1.3.58) |
| ribose production | α(1-4) or β(1-4) glucans | α- or β-(1-4) glucan phosphorylase (EC 2.4.1.1, 2.4.1.49), phosphoglucomutase (EC 5.4.2.2, 5.4.2.5, 5.4.2.6), glucose 6-phosphate dehydrogenase (EC 1.1.1.49, 1.1.1.388, 1.1.1.363), 6-phosphogluconolactonase (EC 3.1.1.31), 6-phosphogluconate dehydrogenase (EC 1.1.1.44, 1.1.1.343, 1.1.1.351), and ribose 5-phosphate isomerase (EC 5.3.1.6), and ribose 5-phosphate phosphatase (EC 3.1.3.-, 3.1.3.58) |
| arabinose production | α(1-4) or β(1-4) glucans | α- or β-(1-4) glucan phosphorylase (EC 2.4.1.1, 2.4.1.49), phosphoglucomutase (EC 5.4.2.2, 5.4.2.5, 5.4.2.6), glucose 6-phosphate dehydrogenase (EC 1.1.1.49, 1.1.1.388, 1.1.1.363), 6-phosphogluconolactonase (EC 3.1.1.31), 6-phosphogluconate dehydrogenase (EC 1.1.1.44, 1.1.1.343, 1.1.1.351), and arabinose 5-phosphate isomerase (EC 5.3.1.13), and arabinose 5-phosphate phosphatase (EC 3.1.3.-, 3.1.3.58) |
| mannose production | α(1-4) or β(1-4) glucans | α- or β-(1-4) glucan phosphorylase (EC 2.4.1.1, 2.4.1.49), phosphoglucomutase (EC 5.4.2.2, 5.4.2.5, 5.4.2.6), phosphoglucoisomerase (EC 5.3.1.9), mannose 6-phosphate isomerase (EC 5.3.1.8), and mannose 6-phosphate phosphatase (EC 3.1.3.-, 3.1.3.58) |

Allulose Production

Some aspects of the present disclosure provide methods, compositions, and systems for producing allulose. These methods, in some embodiments, include culturing cells engineered to express at least one α-glucan phosphorylase and/or at least one cellodextrin phosphorylase, at least one phosphoglucomutase, at least one phosphoglucoisomerase, at least one allulose 6-phosphate epimerase, at least one allulose 6-phosphate phosphatase, or a combination of at least two (e.g., at least three, or at least four) of the foregoing enzymes. In some embodiments, the α-glucan phosphorylase (and/or cellodextrin phosphorylase) and the phosphoglucomutase are expressed as a single fusion (chimeric) protein or a bifunctional protein.

A fusion protein may be created by joining two or more gene or gene segments that code for separate proteins. Translation of this fusion gene results in a single or multiple polypeptides with functional properties derived from each of the original proteins. A polyfunctional protein is a single protein that has at least two different activities, wherein that functionality is a native biological function or the result of an engineered enzyme fusion. Other enzymes may also be expressed as a single fusion protein or a polyfunctional protein. Thus, a fusion protein may contain multiple functionalities of any of the pathway enzymes described herein.

Enzymes of the allulose production pathways as provided herein are typically heterologous to the host cell (initially cloned from or obtained from a different cell type), although some of the enzymes may be endogenous (native) to the host cell. Thus, in some embodiments, at least one enzyme (e.g., thermostable enzyme) used to convert starch and/or cellodextrin to allulose is heterologous to the host cell. In some embodiments, at least two, at least three, or at least four enzymes are heterologous to the host cell. In some embodiments, at least one enzyme is endogenous (native) to the host cell. In some embodiments, at least two, at least three, or at least four enzymes are endogenous to the host cell.

The host cells may be prokaryotic cells, such as bacterial cells (e.g., *Escherichia coli* cells), or eukaryotic cells, such as yeast cells or plant cells. Other cell types are described below.

In some embodiments, at least one of the enzymes used to convert starch and/or cellulose/cellodextrin to allulose is a thermostable enzyme. In some embodiments, at least two (e.g., at least three or at least four) of the enzymes are thermostable enzymes. In some embodiments, all of the enzymes are thermostable enzymes. Thus, in some embodiments, the methods include culturing cells engineered to express at least one thermostable α-glucan phosphorylase, at least one thermostable phosphoglucomutase, at least one thermostable phosphoglucoisomerase, at least one thermostable allulose 6-phosphate epimerase, at least one thermostable allulose 6-phosphate phosphatase, or a combination of at least two or more of the foregoing thermostable enzymes. In some embodiments, the methods include culturing cells engineered to express at least one thermostable cellodextrin phosphorylase, at least one thermostable phosphoglucomutase, at least one thermostable phosphoglucoisomerase, at least one thermostable allulose 6-phosphate epimerase, at least one thermostable allulose 6-phosphate phosphatase, or a combination of at least two or more of the foregoing thermostable enzymes.

In some embodiments, the methods of producing allulose include lysing (e.g., thermal, osmotic, mechanical, chemical, or enzymatic lysis) the cultured cells to produce at least one (e.g., at least two, at least three, or at least four) cell lysate. It should be understood that multiple cell lysates (and thus multiple cell populations, e.g., from the same organism (e.g., bacteria) or from different organisms (e.g., bacteria, yeast, and/or plant cells)) may be used in an enzymatic reaction as provided herein. For example, one cell population may be engineered to express one or more enzymes(s) of the allulose production pathway, while another cell population (or several other cell populations) may be engineered to express another (at least one other) enzyme of the allulose production pathway. Thus, in some embodiments, the methods comprise culturing at least one population of cells engineered to express at least one α-glucan phosphorylase, culturing at least one cell population engineered to express at least one phosphoglucomutase, culturing at least one cell population engineered to express at least one phosphoglucoisomerase, culturing at least one cell population engineered to express at least one allulose 6-phosphate epimerase, and/or culturing at least one cell population engineered to express at least one allulose 6-phosphate phosphatase. In some embodiments, the methods comprise culturing at least one population of cells engineered to express at least one cellodextrin phosphorylase, culturing at least one cell population engineered to express at least one phosphoglucomutase, culturing at least one cell population engineered to express at least one phosphoglucoisomerase, culturing at least one cell population engineered to express at least one allulose 6-phosphate epimerase, and/or culturing at least one cell population engineered to express at least one allulose 6-phosphate phosphatase. Following lysis of the cells, the cell lysates are combined such that the enzymes are present in a single cell lysate/reaction mixture.

It should be understood that in any one of the methods described herein, the cells may be lysed by any means, including mechanical, chemical, enzymatic, osmotic and/or thermal lysis. Thus, a lysing step and a heating (heat inactivation) step may be combined as a single step of heating the cells to a temperature that lyses the cells and inactivates undesired native enzymatic activities.

In some embodiments, the methods further include heating the cell lysate(s) (or a cell lysate mixture) to a temperature that inactivates undesired native enzymatic activities but does not inactivate any of the thermostable enzymes of the production pathway, to produce a heat-inactivated lysate. The cell lysate(s), in some embodiments, is heated to a temperature of at least 50° C. For example, the cell lysate(s) may be heated to a temperature of at least 55° C., 60° C., 65° C., 70° C., 75° C., 80° C., 85° C., or 90° C. A native enzyme (or other non-thermostable enzyme) is considered inactive, in some embodiments, when its level of activity is reduced by at least 50%. In some embodiments, a native enzyme (or other non-thermostable enzyme) is considered inactive when its level of activity is reduced by at least 55%, 60%, 65%, 70%, 75%, 80%, 85%, 90%, 95%, 98%, 99%, or 100%.

The cell lysate(s) may be heated for a period of time sufficient to inactive native enzymes (or other non-thermostable enzymes) of the cell. For example, the cell lysate(s) may be heated for at least 2, 3, 4, or 5 minutes. In some embodiments, the cell lysate(s) are heated for longer than 5 minutes. In some embodiments, the cell lysate(s) are heated for a period of time sufficient to reduce the activity of at least some of the native enzymes (or other non-thermostable enzymes) by at least 50% (e.g., at least 60%, 70%, 80%, or 90%).

Following heat inactivation, in some embodiments, at least one (e.g., at least two or at least three) purified enzyme (or partially purified enzyme) is added to the cell lysate/reaction mixture. Thus, a reaction mixture, in some embodiments, includes a combination of enzymes present in the cell lysate (expressed by the engineered host cell(s)) and at least one purified enzyme. At least one purified enzyme may be selected from the group consisting of α-glucan phosphorylases or cellodextrin phosphorylases, phosphoglucomutases, phosphoglucoisomerases, allulose 6-phosphate epimerases, and allulose 6-phosphate phosphatases.

In some embodiments, the methods also include incubating the heat-inactivated lysate(s) in the presence of a starch and inorganic phosphate to produce allulose. In some embodiments, the methods also include incubating the heat-inactivated lysate(s) in the presence of a cellodextrin and inorganic phosphate to produce allulose. In some embodiments, the heat-inactivated lysates are incubated at a temperature of at least 50 C. In some embodiments, the heat-inactivated lysates are incubated for at least 2 minutes (e.g., at least 3, 4, or 5 minutes). For example, the heat-inactivated lysates may be incubated for 2-5 minutes, or 2-10 minutes. The starch may be, for example, amylose, amylopectin, or a mixture of amylose and amylopectin. In some embodiments, biomass is used instead of starch. For example, the reaction may include cellodextrin phosphorylase(s). In some embodiments, the starch or cellodextrin is present as a component of a compound (e.g., part of the biomass). For example, in some embodiments, the heat-inactivated lysate(s) (e.g., microbial cell lysates) are incubated in the presence of corn pulp and inorganic phosphate to produce allulose (or any other sugar described herein).

Also provided herein are cells and cell lysates used for the production of allulose. Thus, an engineered cell (e.g., bacterial cell, yeast cell, and/or plant cell) or cell lysate(s) of the present disclosure may include at least one (e.g., at least two, at least three, or at least four) enzyme selected from the group consisting of α-glucan phosphorylases, phosphoglucomutases, phosphoglucoisomerases, allulose 6-phosphate epimerases, and allulose 6-phosphate phosphatases. In some embodiments, an engineered cell (e.g., bacterial cell and/or yeast cell) or cell lysate(s) of the present disclosure may include at least one (e.g., at least two, at least three, or at least four) enzyme selected from the group consisting of cellodextrin phosphorylases, phosphoglucomutases, phosphoglucoisomerases, allulose 6-phosphate epimerases, and allulose 6-phosphate phosphatases. In some embodiments, an engineered cell (e.g., bacterial cell, yeast cell, and/or plant cell) or cell lysate(s) of the present disclosure includes at least one (e.g., at least two, at least three, or at least four) enzyme selected from the group consisting of thermostable α-glucan phosphorylases, thermostable phosphoglucomutases, thermostable phosphoglucoisomerases, thermostable allulose 6-phosphate epimerases, and thermostable allulose 6-phosphate phosphatases. In some embodiments, an engineered cell (e.g., bacterial cell and/or yeast cell) or cell lysate(s) of the present disclosure includes at least one (e.g., at least two, at least three, or at least four) enzyme selected from the group consisting of thermostable cellodextrin phosphorylases, thermostable phosphoglucomutases, thermostable phosphoglucoisomerases, thermostable allulose 6-phosphate epimerases, and thermostable allulose 6-phosphate phosphatases.

TABLE 2

Exemplary Allulose Pathway Enzymes

| Pathway Step | Enzyme Name | EC No. | Native Organism | NCBI No. |
|---|---|---|---|---|
| 1 | α-glucan phosphorylase | 2.4.1.1 | Aquifex aeolicus | WP_010880430 |
| | | | Thermocrinis minervae | WP_079654205 |
| | | | Thermosulfidibacter takaii | WP_068550435 |
| | | | Thermosulfurimonas dismutans | WP_068671361 |
| | | | Thermococcus litoralis | WP_004066514 |
| | | | Palaeococcus pacificus | WP_048164525 |
| | | | Thermotoga neapolitana | WP_015919877 |
| | | | Ruminiclostridium thermocellum | WP_003512623 |
| | | | Pyrococcus abyssi | WP_048146597 |
| | | | Thermococcus thioreducens | WP_055429034 |
| | | | Deinococcus radiodurans | NP_295917 |
| | | | Sulfolobus acidocaldarius | WP_011277212 |
| | | | Thermus caldophilus | AAV68178 |
| | | | Meiothermus silvanus | ADH63988 |
| | | | Oceanithermus profundus | WP_013457575 |
| | | | Ardenticatena maritima | WP_054491617 |
| | | | Thermococcus barophilus | WP_013466486 |
| | | | Pseudothermotoga thermarum | WP_013931760 |
| | | | Hydrogenobacter thermophilus | WP_012962737 |
| | | | Thermus oshimai | AFV76231 |
| | | | Meiothermus ruber | WP_013013285 |
| | | | Marinitoga piezophila | WP_014295659 |
| | Cellodextrin phosphorylase (also referred to as cellodextrin phosphorylase) | 2.4.2.49 | Clostridium thermocellum | BAB71818 |
| | | | Clostridium straminisolvens | GAE90338 |
| | | | Thermotoga RQ2 | WP_011943512 |
| | | | Ignisphaera aggregans | ADM28607 |
| | | | Thermotoga maritima | WP_004082399 |
| | | | Spirochaeta thermophila | WP_013314871 |
| | | | Caldicellulosiruptor bescii | WP_015907054 |
| | | | Dictyoglomus thermophilum | WP_012548338 |
| | | | Thermoanaerobacterium thermosaccharolyticum | WP_013297089 |

TABLE 2-continued

Exemplary Allulose Pathway Enzymes

| Pathway Step | Enzyme Name | EC No. | Native Organism | NCBI No. |
|---|---|---|---|---|
| | | | Thermosipho africanus | ACJ76363 |
| | | | Caldisalinibacter kiritimatiensis | WP_006313788 |
| | | | Defluviitalea phaphyphila | WP_058486419 |
| | | | Caldicellulosiruptor kronotskyensis | WP_013429146 |
| | | | Thermococcus sibiricus | WP_015848606 |
| | | | Thermosphaera aggregans | WP_013129904 |
| 2 | Phosphoglucomutase | 5.4.2.6 | Thermococcus kodakaraensis | BAD42440 |
| | | | Pyrococcus kukulkanii | WP_068320630 |
| | | | Ammonifex degensii | WP_015738524 |
| | | | Methanothermobacter wolfeii | WP_074359679 |
| | | | Methanothermus fervidus | WP_013413625 |
| | | | Sulfolobus acidocaldarius | WP_011277678 |
| | | | Archaeoglobus fulgidus | WP_010877965 |
| | | | Ferroglobus placidus | WP_012964640 |
| | | | Geoglobus ahangari | WP_048096365 |
| | | | Archaeoglobus veneficus | WP_013683858 |
| | | | Archaeoglobus sulfaticallidus | WP_015589873 |
| | | | Aciduliprofundum boonie | WP_012997480 |
| | | | Clostridium thermocellum | WP_003517493 |
| | | | Defluviitalea phaphyphila | WP_058485855 |
| | | | Caminicella sporogenes | WP_072968430 |
| | | | Caloranaerobacter ferrireducens | WP_069650396 |
| | | | Thermosipho malanesiensis | WP_012056981 |
| | | | Fervidobacterium pennivorans | WP_014451812 |
| | | | Symbiobacterium thermophilum | WP_011196853 |
| | | | Spirochaeta thermophila | ADN02136 |
| | | | Thermoanaerobacter wiegelii | AEM79998 |
| 3 | Phosphoglucoisomerase | 5.3.1.9 | Thermus thermophilus | WP_041443619 |
| | | | Meiothermus timidus | WP_018467230 |
| | | | Thermus filiformis | WP_038061840 |
| | | | Marinithermus hydrothermalis | WP_013704730 |
| | | | Thermosipho africanus | WP_004103575 |
| | | | Sulfurihydrogenibium azorense | WP_012674892 |
| | | | Persephonella marina | WP_012675923 |
| | | | Marinitoga piezophila | WP_014295589 |
| | | | Kosmotoga olearia | WP_012744692 |
| | | | Thermotoga maritima | WP_004081585 |
| | | | Geobacillus stearothermophilus | KZE97846 |
| | | | Anoxybacillus flavithermus | WP_041638934 |
| | | | Thermosulfidibacter takaii | BAT72177 |
| | | | Fervidobacterium nodosum | WP_011994042 |
| | | | Clostridium thermocellum | WP_003512317 |
| | | | Thermoanaerobacterium thermosaccharolyticum | WP_013297353 |
| | | | Methanococcus jannaschii | WP_010871130 |
| | | | Methanotorris igneus | WP_013799854 |
| | | | Methanocaldococcus villosus | WP_004589908 |
| | | | Methanothermococcus okinawensis | WP_013867340 |
| | | | Pseudothermotoga thermarum | WP_013931655 |
| | | | Deferribacter desulfuricans | WP_013007743 |
| | | | Thermovibrio ammonificans | WP_013537727 |
| 4 | Allulose 6-phosphate epimerase | 5.3.1.- | Thermobacterium thermosaccharolyticum | WP_013298194 |
| | | | Thermoanaerobacter brockii | WP_003868217 |
| | | | Caldanaerobacter subterraneus | WP_011025758 |
| | | | Deferribacter desulfuricans | WP_013008817 |
| | | | Thermocrinis ruber | WP_025305325 |
| | | | Hydrogenivirga sp. 128-5-R1-1 | WP_008287078 |
| | | | Brevibacillus thermoruber | WP_029098887 |
| | | | Thermosipho atlanticus | WP_073071389 |
| | | | Thermosulfidibacter takaii | WP_068550718 |

TABLE 2-continued

Exemplary Allulose Pathway Enzymes

| Pathway Step | Enzyme Name | EC No. | Native Organism | NCBI No. |
|---|---|---|---|---|
| 5 | Allulose 6-phosphate phosphatase | 3.1.3.- | *Thermoanaerobacter wiegelii* | WP_014063120 |
| | | | *Thermoanaerobacter ethanolicus* | WP_003870772 |
| | | | *Thermus islandicus* | WP_022799086 |
| | | | *Deinococcus geothermalis* DSM11300 | ABF44399 |
| | | | *Thermosphaera aggregans* | WP_013129214 |
| | | | *Crenarchaeota archaeon* 13_1_40CM_3_53_5 | WP_013335457 |
| | | | *Pyrococcus horikoshii* Ot3 | WP_010884566 |
| | | | *Aquifex aeolicus* | WP_010880861 |
| | | | *Ruminiclostridium thermocellum* | WP_003512401 |
| | | | *Desulfotomaculum kuznetsovii* | AEG14852 |
| | | | *Caldanaerobacter subterraneus* | WP_009610632 |
| | | | *Acidothermus cellulolyticus* | WP_011718939 |
| | | | *Methanothermobacter thermautotrophicus* | WP_010877362 |
| | | | *Thermobifida fusca* | AAZ54262 |
| | | | *Thermotoga neapolitana* | ACM23496 |
| | | | *Petrotoga mobilis* | WP_012207996 |
| | | | *Thermodesulfatator indicus* | WP_013908370 |
| | | | *Thermus thermophilus* | AAS81813 |
| | | | *Bacteroides vulgatus* | ABR41712 |
| | | | *Bacteroides fragilis* | CAH06673 |

It should be understood that the pathway for producing allulose may be include any combination of enzymes selected from each of Pathways Steps 1-5 of Table 2. For example, the α-glucan phosphorylase of Pathway Step 1 may be selected from any one of the α-glucan phosphorylases of *Aquifex aeolicus, Thermocrinis minervae, Thermosulfidibacter takaii, Thermosulfurimonas dismutans, Thermococcus litoralis, Palaeococcus pacificus, Thermotoga neapolitana, Ruminiclostridium thermocellum, Pyrococcus abyssi, Thermococcus thioreducens, Deinococcus radiodurans, Sulfolobus acidocaldarius, Thermus caldophilus, Meiothermus silvanus, Oceanithermus profundus, Ardenticatena maritima, Thermococcus barophilus, Pseudothermotoga thermarum, Hydrogenobacter thermophilus, Thermus oshimai, Meiothermus ruber,* and *Marinitoga piezophila* and combined with a phosphoglucomutase of Pathway Step 2 selected from any one of the phosphoglucomutase of *Thermococcus kodakaraensis, Pyrococcus kukulkanii, Ammonifex degensii, Methanothermobacter wolfeii, Methanothermus fervidus, Sulfolobus acidocaldarius, Archaeoglobus fulgidus, Ferroglobus placidus, Geoglobus ahangari, Archaeoglobus veneficus, Archaeoglobus sulfaticallidus, Aciduliprofundum boonie, Clostridium thermocellum, Defluviitalea phaphyphila, Caminicella sporogenes, Caloranaerobacter ferrireducens, Thermosipho malanesiensis, Fervidobacterium pennivorans, Symbiobacterium thermophilum, Spirochaeta thermophila,* and *Thermoanaerobacter wiegelii*.

Glucose Production

Other aspects of the present disclosure provide methods, compositions, and systems for producing glucose. These methods, in some embodiments, include culturing cells engineered to express at least one α-glucan phosphorylase and/or at least one cellodextrin phosphorylase, at least one phosphoglucomutase, at least one glucose 6-phosphate phosphatase, or a combination of at least two of the foregoing enzymes. In some embodiments, the α-glucan phosphorylase (and/or cellodextrin phosphorylase) and the phosphoglucomutase are expressed as a single fusion (chimeric) protein or a bifunctional protein. In some embodiments, these methods include culturing cells engineered to express at least one α-glucan phosphorylase and/or at least one cellodextrin phosphorylase, at least one glucose 1-phosphate phosphatase, or a combination of at least two of the foregoing enzymes. In some embodiments, the α-glucan phosphorylase (and/or cellodextrin phosphorylase) and the phosphoglucomutase are expressed as a single fusion (chimeric) protein or a bifunctional protein.

Enzymes of the glucose production pathways as provided herein are typically heterologous to the host cell (initially cloned from or obtained from a different cell type), although some of the enzymes may be endogenous (native) to the host cell. Thus, in some embodiments, at least one enzyme (e.g., thermostable enzyme) used to convert starch and/or cellodextrin to glucose is heterologous to the host cell. In some embodiments, at least two enzymes are heterologous to the host cell. In some embodiments, at least one enzyme (e.g., thermostable enzyme) is endogenous (native) to the host cell. In some embodiments, at least two enzymes are endogenous to the host cell.

The host cells may be prokaryotic cells, such as bacterial cells (e.g., *Escherichia coli* cells), or eukaryotic cells, such as yeast cells or plant cells. Other cell types are described below.

In some embodiments, at least one of the enzymes used to convert starch and/or cellodextrin to glucose is a thermostable enzyme. In some embodiments, at least two of the enzymes are thermostable enzymes. In some embodiments, all of the enzymes are thermostable enzymes. Thus, in some embodiments, the methods include culturing cells engineered to express at least one thermostable α-glucan phosphorylase, at least one thermostable phosphoglucomutase, at least one thermostable glucose 6-phosphate phosphatase, or a combination of at least two or more of the foregoing thermostable enzymes. In some embodiments, the methods include culturing cells engineered to express at least one thermostable cellodextrin phosphorylase, at least one thermostable phosphoglucomutase, at least one thermostable glucose 6-phosphate phosphatase, or a combination of at least two or more of the foregoing thermostable enzymes. In some embodiments, the methods include culturing cells engineered to express at least one thermostable α-glucan phosphorylase, at least one thermostable glucose 1-phosphate phosphatase, or a combination of at least two or more of the foregoing thermostable enzymes. In some embodiments, the methods include culturing cells engineered to express at least one thermostable cellodextrin phosphorylase, at least one thermostable glucose 1-phosphate phosphatase, or a combination of at least two or more of the foregoing thermostable enzymes.

In some embodiments, the methods of producing glucose include lysing (e.g., thermal, mechanical, chemical, or enzymatic lysis) the cultured cells to produce at least one (e.g., at least two, at least three, or at least four) cell lysate. It should be understood that multiple cell lysates (and thus multiple cell populations, e.g., from the same organism (e.g., bacteria) or from different organisms (e.g., bacteria, yeast and or plant cells)) may be used in an enzymatic reaction as provided herein. For example, one cell population may be engineered to express one or more enzymes(s) of the glucose production pathway, while another cell population (or several other cell populations) may be engineered to express another (at least one other) enzyme of the glucose production pathway. Thus, in some embodiments, the methods comprise culturing at least one population of cells engineered to express at least one α-glucan phosphorylase, culturing at least one cell population engineered to express at least one phosphoglucomutase, and/or culturing at least one cell population engineered to express at least one glucose 6-phosphate phosphatase. In some embodiments, the methods comprise culturing at least one population of cells engineered to express at least one cellodextrin phosphorylase, culturing at least one cell population engineered to express at least one phosphoglucomutase, and/or culturing at least one cell population engineered to express at least one glucose 6-phosphate phosphatase. In some embodiments, the methods comprise culturing at least one population of cells engineered to express at least one α-glucan phosphorylase, and/or culturing at least one cell population engineered to express at least one glucose 1-phosphate phosphatase. In some embodiments, the methods comprise culturing at least one population of cells engineered to express at least one cellodextrin phosphorylase, and/or culturing at least one cell population engineered to express at least one glucose 1-phosphate phosphatase. Following lysis of the cells, the cell lysates are combined such that the enzymes are present in a single cell lysate/reaction mixture.

In some embodiments, the methods further include heating the cell lysate(s) (or a cell lysate mixture) to a temperature that inactivates undesired native enzymatic activities but does not inactivate any of the thermostable enzymes of the production pathway, to produce a heat-inactivated lysate. The cell lysate(s), in some embodiments, is heated to a temperature of at least 50° C. For example, the cell lysate(s) may be heated to a temperature of at least 55° C., 60° C., 65° C., 70° C., 75° C., 80° C., 85° C., or 90° C.

The cell lysate(s) may be heated for a period of time sufficient to inactive native enzymes (or other non-thermostable enzymes) of the cell. For example, the cell lysate(s) may be heated for at least 2, 3, 4, or at least 5 minutes. In some embodiments, the cell lysate(s) are heated for longer than 5 minutes. In some embodiments, the cell lysate(s) are heated for a period of time sufficient to reduce the activity of native enzymes (or other non-thermostable enzymes) by at least 50% (e.g., at least 60%, 70%, 80%, or 90%).

Following heat inactivation, in some embodiments, at least one (e.g., at least two or at least three) purified enzymes is added to the cell lysate/reaction mixture. Thus, a reaction mixture, in some embodiments, includes a combination of enzymes present in the cell lysate (expressed by the engineered host cell(s)) and at least one purified enzyme. At least one purified enzyme may be selected from the group consisting of α-glucan phosphorylases or cellodextrin phosphorylases, phosphoglucomutases, and glucose 6-phosphate phosphatases. Alternatively, at least one purified enzyme may be selected from the group consisting of α-glucan phosphorylases or cellodextrin phosphorylases and glucose 1-phosphate phosphatases.

In some embodiments, the methods also include incubating the heat-inactivated lysate(s) in the presence of a starch and inorganic phosphate to produce glucose. In some embodiments, the methods also include incubating the heat-inactivated lysate(s) in the presence of a cellodextrin and inorganic phosphate to produce glucose. In some embodiments, the heat-inactivated lysates are incubated at a temperature of at least 50 C. In some embodiments, the heat-inactivated lysates are incubated for at least 2 minutes (e.g., at least 3, 4, or 5 minutes). For example, the heat-inactivated lysates may be incubated for 2-5 minutes, or 2-10 minutes.

The starch may be, for example, amylose, amylopectin, or a mixture of amylose and amylopectin. In some embodiments, biomass is used instead of starch. In these embodiments, the reaction includes cellodextrin phosphorylase(s). In some embodiments, the starch or cellodextrin is present as a component of a compound.

Also provided herein are cells and cell lysates used for the production of glucose. Thus, an engineered cell (e.g., bacterial cell and/or yeast cell) or cell lysate(s) of the present disclosure may include at least one (e.g., at least two) enzyme selected from the group consisting of α-glucan phosphorylases, phosphoglucomutases, and glucose 6-phosphate phosphatases. In some embodiments, an engineered cell (e.g., bacterial cell and/or yeast cell) or cell lysate(s) of the present disclosure may include at least one (e.g., at least two) enzyme selected from the group consisting of cellodextrin phosphorylases, phosphoglucomutases, and glucose 6-phosphate phosphatases. An engineered cell (e.g., bacterial cell and/or yeast cell) or cell lysate(s) of the present disclosure may include at least one (e.g., at least two) enzyme selected from the group consisting of α-glucan phosphorylases and glucose 1-phosphate phosphatases. In some embodiments, an engineered cell (e.g., bacterial cell and/or yeast cell) or cell lysate(s) of the present disclosure may include at least one (e.g., at least two) enzyme selected from the group consisting of cellodextrin phosphorylases and glucose 1-phosphate phosphatases. In some embodiments, an engineered cell (e.g., bacterial cell and/or yeast cell) or cell lysate(s) of the present disclosure includes at least one (e.g., at least two) enzyme selected from the group consisting of thermostable α-glucan phosphorylases, thermostable phosphoglucomutases, and thermostable glucose 6-phosphate phosphatases. In some embodiments, an engineered cell (e.g., bacterial cell and/or yeast cell) or cell lysate(s) of the present disclosure includes at least one (e.g., at least two) enzyme selected from the group consisting of thermostable cellodextrin phosphorylases, thermostable phosphoglucomutases, and thermostable glucose 6-phosphate phosphatases. In some embodiments, an engineered cell (e.g., bacterial cell and/or yeast cell) or cell lysate(s) of the present disclosure includes at least one (e.g., at least two) enzyme selected from the group consisting of thermostable α-glucan phosphorylases and thermostable glucose 1-phosphate phosphatases. In some embodiments, an engineered cell (e.g., bacterial cell and/or yeast cell) or cell lysate(s) of the present disclosure includes at least one (e.g., at least two) enzyme selected from the group consisting of thermostable cellodextrin phosphorylases and thermostable glucose 1-phosphate phosphatases.

Fructose Production

Yet other aspects of the present disclosure provide methods, compositions, and systems for producing fructose. These methods, in some embodiments, include culturing cells engineered to express at least one α-glucan phosphorylase and/or cellodextrin phosphorylase, at least one phosphoglucomutase, at least one phosphoglucoisomerase, at least one fructose 6-phosphate phosphatase, or a combination of at least two of the foregoing enzymes. In some embodiments, the α-glucan phosphorylase (and/or cellodextrin phosphorylase) and the phosphoglucomutase are expressed as a single fusion (chimeric) protein or a bifunctional protein.

Enzymes of the fructose production pathways as provided herein are typically heterologous to the host cell (initially cloned from or obtained from a different cell type), although some of the enzymes may be endogenous (native) to the host cell. Thus, in some embodiments, at least one enzyme (e.g., thermostable enzyme) used to convert starch and/or cellodextrin to fructose is heterologous to the host cell. In some embodiments, at least two or at least three enzymes are heterologous to the host cell. In some embodiments, at least one enzyme (e.g., thermostable enzyme) is endogenous (native) to the host cell. In some embodiments, at least two or at least three enzymes are endogenous to the host cell.

The host cells may be prokaryotic cells, such as bacterial cells (e.g., *Escherichia coli* cells), or eukaryotic cells, such as yeast cells or plant cells. Other cell types are described below.

In some embodiments, at least one of the enzymes used to convert starch and/or cellodextrin to fructose is a thermostable enzyme. In some embodiments, at least two or at least three of the enzymes are thermostable enzymes. In some embodiments, all of the enzymes are thermostable enzymes. Thus, in some embodiments, the methods include culturing cells engineered to express at least one thermostable α-glucan phosphorylase, at least one thermostable phosphoglucomutase, at least one thermostable phosphoglucoisomerase, at least one thermostable fructose 6-phosphate phosphatase, or a combination of at least two or more of the foregoing thermostable enzymes. In some embodiments, the methods include culturing cells engineered to express at least one thermostable cellodextrin phosphorylase, at least one thermostable phosphoglucomutase, at least one thermostable phosphoglucoisomerase, at least one thermostable fructose 6-phosphate phosphatase, or a combination of at least two or more of the foregoing thermostable enzymes.

In some embodiments, the methods of producing fructose include lysing (e.g., thermal, mechanical, chemical, or enzymatic lysis) the cultured cells to produce at least one (e.g., at least two, at least three, or at least four) cell lysate. It should be understood that multiple cell lysates (and thus multiple cell populations, e.g., from the same organism (e.g., bacteria) or from different organisms (e.g., bacteria, yeast and or plant cells)) may be used in an enzymatic reaction as provided herein. For example, one cell population may be engineered to express one or more enzymes(s) of the fructose production pathway, while another cell population (or several other cell populations) may be engineered to express another (at least one other) enzyme of the fructose production pathway. Thus, in some embodiments, the methods comprise culturing at least one population of cells engineered to express at least one α-glucan phosphorylase, culturing at least one cell population engineered to express at least one phosphoglucomutase, culturing at least one cell population engineered to express at least one phosphoglucoisomerase, and/or culturing at least one cell population engineered to express at least one fructose 6-phosphate phosphatase. In some embodiments, the methods comprise culturing at least one population of cells engineered to express at least one cellodextrin phosphorylase, culturing at least one cell population engineered to express at least one phosphoglucomutase, culturing at least one cell population engineered to express at least one phosphoglucoisomerase, and/or culturing at least one cell population engineered to express at least one fructose 6-phosphate phosphatase. Following lysis of the cells, the cell lysates are combined such that the enzymes are present in a single cell lysate/reaction mixture.

In some embodiments, the methods further include heating the cell lysate(s) (or a cell lysate mixture) to a temperature that inactivates undesired native enzymatic activities but does not inactivate any of the thermostable enzymes of the production pathway, to produce a heat-inactivated lysate. The cell lysate(s), in some embodiments, is heated to a temperature of at least 50° C. For example, the cell lysate(s) may be heated to a temperature of at least 55° C., 60° C., 65° C., 70° C., 75° C., 80° C., 85° C., or 90° C.

The cell lysate(s) may be heated for a period of time sufficient to inactive native enzymes (or other non-thermostable enzymes) of the cell. For example, the cell lysate(s) may be heated for at least 2, 3, 4, or at least 5 minutes. In some embodiments, the cell lysate(s) are heated for longer than 5 minutes. In some embodiments, the cell lysate(s) are heated for a period of time sufficient to reduce the activity of native enzymes (or other non-thermostable enzymes) by at least 50% (e.g., at least 60%, 70%, 80%, or 90%).

Following heat inactivation, in some embodiments, at least one (e.g., at least two or at least three) purified enzymes is added to the cell lysate/reaction mixture. Thus, a reaction mixture, in some embodiments, includes a combination of enzymes present in the cell lysate (expressed by the engineered host cell(s)) and at least one purified enzyme. At least one purified enzyme may be selected from the group consisting of α-glucan phosphorylases or cellodextrin phosphorylases, phosphoglucomutases, phosphoglucoisomerases, and fructose 6-phosphate phosphatases.

In some embodiments, the methods also include incubating the heat-inactivated lysate(s) in the presence of a starch and inorganic phosphate to produce fructose. In some embodiments, the methods also include incubating the heat-inactivated lysate(s) in the presence of a cellodextrin and inorganic phosphate to produce fructose. In some embodiments, the heat-inactivated lysates are incubated at a temperature of at least 50 C. In some embodiments, the heat-inactivated lysates are incubated for at least 2 minutes (e.g., at least 3, 4, or 5 minutes). For example, the heat-inactivated lysates may be incubated for 2-5 minutes, or 2-10 minutes. The starch may be, for example, amylose, amylopectin, or a mixture of amylose and amylopectin. In some embodiments, biomass is used instead of starch. In these embodiments, the reaction includes cellodextrin phosphorylase(s). In some embodiments, the starch or cellodextrin is present as a component of a compound.

Also provided herein are cells and cell lysates used for the production of fructose. Thus, an engineered cell (e.g., bacterial cell and/or yeast cell) or cell lysate(s) of the present disclosure may include at least one (e.g., at least two or at least three) enzyme selected from the group consisting of α-glucan phosphorylases, phosphoglucomutases, and fructose 6-phosphate phosphatases. In some embodiments, an engineered cell (e.g., bacterial cell and/or yeast cell) or cell lysate(s) of the present disclosure includes at least one (e.g., at least two or at least three) enzyme selected from the group consisting of thermostable α-glucan phosphorylases, thermostable phosphoglucomutases, and thermostable fructose 6-phosphate phosphatase. In some embodiments, an engineered cell (e.g., bacterial cell and/or yeast cell) or cell lysate(s) of the present disclosure includes at least one (e.g., at least two or at least three) enzyme selected from the group consisting of thermostable cellodextrin phosphorylases, thermostable phosphoglucomutases, and thermostable fructose 6-phosphate phosphatase.

Mannose Production

Further still, some aspects of the present disclosure provide methods, compositions, and systems for producing mannose. These methods, in some embodiments, include culturing cells engineered to express at least one α-glucan phosphorylase and/or at least one cellodextrin phosphorylase, at least one phosphoglucomutase, at least one phosphoglucoisomerase, at least one mannose 6-phosphate isomerase, at least one mannose 6-phosphate phosphatase, or a combination of at least two of the foregoing enzymes. In some embodiments, the α-glucan phosphorylase (and/or cellodextrin phosphorylase) and the phosphoglucomutase are expressed as a single fusion (chimeric) protein or a bifunctional protein.

Enzymes of the mannose production pathways as provided herein are typically heterologous to the host cell (initially cloned from or obtained from a different cell type), although some of the enzymes may be endogenous (native) to the host cell. Thus, in some embodiments, at least one enzyme (e.g., thermostable enzyme) used to convert starch and/or cellodextrin to mannose is heterologous to the host cell. In some embodiments, at least two, at least three, at least four, at least five, or at least six enzymes are heterologous to the host cell. In some embodiments, at least one enzyme (e.g., thermostable enzyme) is endogenous (native) to the host cell. In some embodiments, at least two, at least three, at least four, at least five, or at least six enzymes are endogenous to the host cell.

The host cells may be prokaryotic cells, such as bacterial cells (e.g., *Escherichia coli* cells), or eukaryotic cells, such as yeast cells or plant cells. Other cell types are described below.

In some embodiments, at least one of the enzymes used to convert starch and/or cellodextrin to mannose is a thermostable enzyme. In some embodiments, at least two, at least three, at least four, at least five, or at least six of the enzymes are thermostable enzymes. In some embodiments, all of the enzymes are thermostable enzymes. Thus, in some embodiments, the methods include culturing cells engineered to express at least one thermostable α-glucan phosphorylase, at least one thermostable phosphoglucomutase, at least one thermostable phosphoglucoisomerase, at least one thermostable mannose 6-phosphate isomerase, at least one thermostable mannose 6-phosphate phosphatase, or a combination of at least two or more of the foregoing thermostable enzymes. In some embodiments, the methods include culturing cells engineered to express at least one thermostable cellodextrin phosphorylase, at least one thermostable phosphoglucomutase, at least one thermostable phosphoglucoisomerase, at least one thermostable mannose 6-phosphate isomerase, at least one thermostable mannose 6-phosphate phosphatase, or a combination of at least two or more of the foregoing thermostable enzymes.

In some embodiments, the methods of producing mannose include lysing (e.g., thermal, mechanical, chemical, or enzymatic lysis) the cultured cells to produce at least one (e.g., at least two, at least three, or at least four) cell lysate. It should be understood that multiple cell lysates (and thus multiple cell populations, e.g., from the same organism (e.g., bacteria) or from different organisms (e.g., bacteria, yeast and or plant cells)) may be used in an enzymatic reaction as provided herein. For example, one cell population may be engineered to express one or more enzymes(s) of the mannose production pathway, while another cell population (or several other cell populations) may be engineered to express another (at least one other) enzyme of the mannose production pathway. Thus, in some embodiments, the methods comprise culturing at least one population of cells engineered to express at least one α-glucan phosphorylase, culturing at least one cell population engineered to express at least one phosphoglucomutase, culturing at least one cell population engineered to express at least one phosphoglucoisomerase, culturing at least one cell population engineered to express at least one mannose 6-phosphate isomerase, and/or culturing at least one cell population engineered to express at least one mannose 6-phosphate phosphatase. In some embodiments, the methods comprise culturing at least one population of cells engineered to express at least one cellodextrin phosphorylase, culturing at least one cell population engineered to express at least one phosphoglucomutase, culturing at least one cell population engineered to express at least one phosphoglucoisomerase, culturing at least one cell population engineered to express at least one mannose 6-phosphate isomerase, and/or culturing at least one cell population engineered to express at least one mannose 6-phosphate phosphatase. Following lysis of the cells, the cell lysates are combined such that the enzymes are present in a single cell lysate/reaction mixture.

In some embodiments, the methods further include heating the cell lysate(s) (or a cell lysate mixture) to a temperature that inactivates undesired native enzymatic activities but does not inactivate any of the thermostable enzymes of the production pathway, to produce a heat-inactivated lysate. The cell lysate(s), in some embodiments, is heated to a temperature of at least 50° C. For example, the cell lysate(s) may be heated to a temperature of at least 55° C., 60° C., 65° C., 70° C., 75° C., 80° C., 85° C., or 90° C.

The cell lysate(s) may be heated for a period of time sufficient to inactive native enzymes (or other non-thermostable enzymes) of the cell. For example, the cell lysate(s) may be heated for at least 2, 3, 4, or at least 5 minutes. In some embodiments, the cell lysate(s) are heated for longer than 5 minutes. In some embodiments, the cell lysate(s) are heated for a period of time sufficient to reduce the activity of native enzymes (or other non-thermostable enzymes) by at least 50% (e.g., at least 60%, 70%, 80%, or 90%).

Following heat inactivation, in some embodiments, at least one (e.g., at least two or at least three) purified enzymes is added to the cell lysate/reaction mixture. Thus, a reaction mixture, in some embodiments, includes a combination of enzymes present in the cell lysate (expressed by the engineered host cell(s)) and at least one purified enzyme. At least one purified enzyme may be selected from the group consisting of α-glucan phosphorylases or cellodextrin phosphorylases, phosphoglucomutases, phosphoglucoisomerase, mannose 6-phosphate isomerases, and mannose 6-phosphate phosphatases.

In some embodiments, the methods also include incubating the heat-inactivated lysate(s) in the presence of a starch and inorganic phosphate to produce mannose. In some embodiments, the methods also include incubating the heat-inactivated lysate(s) in the presence of a cellodextrin and inorganic phosphate to produce mannose. In some embodiments, the heat-inactivated lysates are incubated at a temperature of at least 50 C. In some embodiments, the heat-inactivated lysates are incubated for at least 2 minutes (e.g., at least 3, 4, or 5 minutes). For example, the heat-inactivated lysates may be incubated for 2-5 minutes, or 2-10 minutes. The starch may be, for example, amylose, amylopectin, or a mixture of amylose and amylopectin. In some embodiments, biomass is used instead of starch. In these embodiments, the reaction includes cellodextrin phosphorylase(s). In some embodiments, the starch or cellodextrin is present as a component of a compound.

Also provided herein are cells and cell lysates used for the production of mannose. Thus, an engineered cell (e.g., bacterial cell and/or yeast cell) or cell lysate(s) of the present disclosure may include at least one (e.g., at least two, at least three, at least four, at least five, or at least six) enzyme selected from the group consisting of α-glucan phosphorylases, phosphoglucomutases, phosphoglucoisomerases, mannose 6-phosphate isomerases, and mannose 6-phosphate phosphatases. An engineered cell (e.g., bacterial cell and/or yeast cell) or cell lysate(s) of the present disclosure may include at least one (e.g., at least two, at least three, at least four, at least five, or at least six) enzyme selected from the group consisting of cellodextrin phosphorylases, phosphoglucomutases, phosphoglucoisomerases, mannose 6-phosphate isomerases, and mannose 6-phosphate phosphatases. In some embodiments, an engineered cell (e.g., bacterial cell and/or yeast cell) or cell lysate(s) of the present disclosure includes at least one (e.g., at least two, at least three, at least four, at least five, or at least six) enzyme selected from the group consisting of thermostable α-glucan phosphorylases, thermostable phosphoglucomutases, thermostable phosphoglucoisomerases, thermostable mannose 6-phosphate isomerases, and thermostable mannose 6-phosphate phosphatases. In some embodiments, an engineered cell (e.g., bacterial cell and/or yeast cell) or cell lysate(s) of the present disclosure includes at least one (e.g., at least two, at least three, at least four, at least five, or at least six) enzyme selected from the group consisting of thermostable cellodextrin phosphorylases, thermostable phosphoglucomutases, thermostable phosphoglucoisomerases, thermostable mannose 6-phosphate isomerases, and thermostable mannose 6-phosphate phosphatases.

Sorbitol Production

Still other aspects of the present disclosure provide methods, compositions, and systems for producing sorbitol. These methods, in some embodiments, include culturing cells engineered to express at least one α-glucan phosphorylase and/or at least on cellodextrin phosphorylase, at least one phosphoglucomutase, at least one aldose dehydrogenase, at least one sorbitol-6-phosphate phosphatase, or a combination of at least two of the foregoing enzymes. In some embodiments, the methods include culturing cells engineered to express at least one α-glucan phosphorylase and/or at least on cellodextrin phosphorylase, at least one phosphoglucomutase, at least one phosphoglucoisomerase, at least one sorbitol-6-phosphate 2-dehydrogenase, at least one sorbitol-6-phosphate phosphatase, or a combination of at least two of the foregoing enzymes. In some embodiments, the α-glucan phosphorylase (and/or cellodextrin phosphorylase) and the phosphoglucomutase are expressed as a single fusion (chimeric) protein or a bifunctional protein.

Enzymes of the sorbitol production pathways as provided herein are typically heterologous to the host cell (initially cloned from or obtained from a different cell type), although some of the enzymes may be endogenous (native) to the host cell. Thus, in some embodiments, at least one enzyme (e.g., thermostable enzyme) used to convert starch and/or cellodextrin to sorbitol is heterologous to the host cell. In some embodiments, at least two or at least three enzymes are heterologous to the host cell. In some embodiments, at least one enzyme (e.g., thermostable enzyme) is endogenous (native) to the host cell. In some embodiments, at least two or at least three enzymes are endogenous to the host cell.

The host cells may be prokaryotic cells, such as bacterial cells (e.g., *Escherichia coli* cells), or eukaryotic cells, such as yeast cells or plant cells. Other cell types are described below.

In some embodiments, at least one of the enzymes used to convert starch and/or cellodextrin to sorbitol is a thermostable enzyme. In some embodiments, at least two, at least three, or at least four of the enzymes are thermostable enzymes. In some embodiments, all of the enzymes are thermostable enzymes. Thus, in some embodiments, the methods include culturing cells engineered to express at least one thermostable α-glucan phosphorylase, at least one thermostable phosphoglucomutase, at least one thermostable aldose dehydrogenase, at least one thermostable sorbitol-6-phosphate phosphatase, or a combination of at least two or more of the foregoing thermostable enzymes. In some embodiments, the methods include culturing cells engineered to express at least one thermostable cellodextrin phosphorylase, at least one thermostable phosphoglucomutase, at least one thermostable aldose dehydrogenase, at least one thermostable sorbitol-6-phosphate phosphatase, or a combination of at least two or more of the foregoing thermostable enzymes. In some embodiments, the methods include culturing cells engineered to express at least one thermostable α-glucan phosphorylase, at least one thermostable phosphoglucomutase, at least one thermostable phosphoglucoisomerase, at least one thermostable sorbitol-6-phosphate 2-dehydrogenase, at least one thermostable sorbitol-6-phosphate phosphatase, or a combination of at least two or more of the foregoing thermostable enzymes. In some embodiments, the methods include culturing cells engineered to express at least one thermostable cellodextrin phosphorylase, at least one thermostable phosphoglucomutase, at least one thermostable phosphoglucoisomerase, at least one thermostable sorbitol-6-phosphate 2-dehydrogenase, at least one thermostable sorbitol-6-phosphate phosphatase, or a combination of at least two or more of the foregoing thermostable enzymes.

In some embodiments, the methods of producing sorbitol include lysing (e.g., thermal, mechanical, chemical, or enzymatic lysis) the cultured cells to produce at least one (e.g., at least two, at least three, or at least four) cell lysate. It should be understood that multiple cell lysates (and thus multiple cell populations, e.g., from the same organism (e.g., bacteria) or from different organisms (e.g., bacteria, yeast and or plant cells)) may be used in an enzymatic reaction as provided herein. For example, one cell population may be engineered to express one or more enzymes(s) of the sorbitol production pathway, while another cell population (or several other cell populations) may be engineered to express another (at least one other) enzyme of the sorbitol production pathway. Thus, in some embodiments, the methods comprise culturing at least one population of cells engineered to express at least one α-glucan phosphorylase, culturing at least one cell population engineered to express at least one phosphoglucomutase, culturing at least one cell population engineered to express at least one aldose dehydrogenase, and/or culturing at least one cell population engineered to express at least one sorbitol-6-phosphate phosphatase. In some embodiments, the methods comprise culturing at least one population of cells engineered to express at least one cellodextrin phosphorylase, culturing at least one cell population engineered to express at least one phosphoglucomutase, culturing at least one cell population engineered to express at least one aldose dehydrogenase, and/or culturing at least one cell population engineered to express at least one sorbitol-6-phosphate phosphatase. Following lysis of the cells, the cell lysates are combined such that the enzymes are present in a single cell lysate/reaction mixture.

In some embodiments, the methods further include heating the cell lysate(s) (or a cell lysate mixture) to a temperature that inactivates undesired native enzymatic activities but does not inactivate any of the thermostable enzymes of the production pathway, to produce a heat-inactivated lysate. The cell lysate(s), in some embodiments, is heated to a temperature of at least 50° C. For example, the cell lysate(s) may be heated to a temperature of at least 55° C., 60° C., 65° C., 70° C., 75° C., 80° C., 85° C., or 90° C.

The cell lysate(s) may be heated for a period of time sufficient to inactive native enzymes (or other non-thermostable enzymes) of the cell. For example, the cell lysate(s) may be heated for at least 2, 3, 4, or at least 5 minutes. In some embodiments, the cell lysate(s) are heated for longer than 5 minutes. In some embodiments, the cell lysate(s) are heated for a period of time sufficient to reduce the activity of native enzymes (or other non-thermostable enzymes) by at least 50% (e.g., at least 60%, 70%, 80%, or 90%).

Following heat inactivation, in some embodiments, at least one (e.g., at least two or at least three) purified enzymes is added to the cell lysate/reaction mixture. Thus, a reaction mixture, in some embodiments, includes a combination of enzymes present in the cell lysate (expressed by the engineered host cell(s)) and at least one purified enzyme. At least one purified enzyme may be selected from the group consisting of α-glucan phosphorylases or cellodextrin phosphorylases, phosphoglucomutases, phosphoglucoisomerases, sorbitol-6-phosphate 2-dehydrogenases, aldose dehydrogenases, and sorbitol-6-phosphate phosphatases.

In some embodiments, the methods also include incubating the heat-inactivated lysate(s) in the presence of a starch and inorganic phosphate to produce sorbitol. In some embodiments, the methods also include incubating the heat-inactivated lysate(s) in the presence of a cellodextrin and inorganic phosphate to produce sorbitol. In some embodiments, the heat-inactivated lysates are incubated at a temperature of at least 50 C. In some embodiments, the heat-inactivated lysates are incubated for at least 2 minutes (e.g., at least 3, 4, or 5 minutes). For example, the heat-inactivated lysates may be incubated for 2-5 minutes, or 2-10 minutes. The starch may be, for example, amylose, amylopectin, or a mixture of amylose and amylopectin. In some embodiments, biomass is used instead of starch. In these embodiments, the reaction includes cellodextrin phosphorylase(s). In some embodiments, the starch or cellodextrin is present as a component of a compound.

Also provided herein are cells and cell lysates used for the production of sorbitol. Thus, an engineered cell (e.g., bacterial cell and/or yeast cell) or cell lysate(s) of the present disclosure may include at least one (e.g., at least two or at least three) enzyme selected from the group consisting of α-glucan phosphorylases, phosphoglucomutases, aldose dehydrogenases, and sorbitol-6-phosphate phosphatases. An engineered cell (e.g., bacterial cell and/or yeast cell) or cell lysate(s) of the present disclosure may include at least one (e.g., at least two or at least three) enzyme selected from the group consisting of cellodextrin phosphorylases, phosphoglucomutases, aldose dehydrogenases, and sorbitol-6-phosphate phosphatases. In some embodiments, an engineered cell (e.g., bacterial cell and/or yeast cell) or cell lysate(s) of the present disclosure includes at least one (e.g., at least two or at least three) enzyme selected from the group consisting of thermostable α-glucan phosphorylases, thermostable phosphoglucomutases, thermostable aldose dehydrogenases, and thermostable sorbitol-6-phosphate phosphatases. In some embodiments, an engineered cell (e.g., bacterial cell and/or yeast cell) or cell lysate(s) of the present disclosure includes at least one (e.g., at least two or at least three) enzyme selected from the group consisting of thermostable cellodextrin phosphorylases, thermostable phosphoglucomutases, thermostable aldose dehydrogenases, and thermostable sorbitol-6-phosphate phosphatases. Thus, an engineered cell (e.g., bacterial cell and/or yeast cell) or cell lysate(s) of the present disclosure may include at least one (e.g., at least two or at least three) enzyme selected from the group consisting of α-glucan phosphorylases, phosphoglucomutases, phosphoglucoisomerases, sorbitol-6-phosphate 2-dehydrogenases, and sorbitol-6-phosphate phosphatases. An engineered cell (e.g., bacterial cell and/or yeast cell) or cell lysate(s) of the present disclosure may include at least one (e.g., at least two or at least three) enzyme selected from the group consisting of cellodextrin phosphorylases, phosphoglucomutases, phosphoglucoisomerases, sorbitol-6-phosphate 2-dehydrogenases, and sorbitol-6-phosphate phosphatases. In some embodiments, an engineered cell (e.g., bacterial cell and/or yeast cell) or cell lysate(s) of the present disclosure includes at least one (e.g., at least two or at least three) enzyme selected from the group consisting of thermostable α-glucan phosphorylases, thermostable phosphoglucomutases, thermostable phosphoglucoisomerases, thermostable sorbitol-6-phosphate aldose dehydrogenases, and thermostable sorbitol-6-phosphate phosphatases. In some embodiments, an engineered cell (e.g., bacterial cell and/or yeast cell) or cell lysate(s) of the present disclosure includes at least one (e.g., at least two or at least three) enzyme selected from the group consisting of thermostable cellodextrin phosphorylases, thermostable phosphoglucomutases, thermostable phosphoglucoisomerases, thermostable sorbitol-6-phosphate 2-dehydrogenases, and thermostable sorbitol-6-phosphate phosphatases.

Ribulose Production

Further aspects of the present disclosure provide methods, compositions, and systems for producing ribulose. These methods, in some embodiments, include culturing cells engineered to express at least one α-glucan phosphorylase and/or cellodextrin phosphorylase, at least one phosphoglucomutase, at least one glucose 6-phosphate dehydrogenase, at least one 6-phosphogluconolactonase, at least one 6-phosphogluconate dehydrogenase, at least one ribulose 5-phosphate phosphatase, or a combination of at least two of the foregoing enzymes. In some embodiments, the α-glucan phosphorylase (and/or cellodextrin phosphorylase) and the phosphoglucomutase are expressed as a single fusion (chimeric) protein or a bifunctional protein.

Enzymes of the ribulose production pathways as provided herein are typically heterologous to the host cell (initially cloned from or obtained from a different cell type), although some of the enzymes may be endogenous (native) to the host cell. Thus, in some embodiments, at least one enzyme (e.g., thermostable enzyme) used to convert starch and/or cellodextrin to ribulose is heterologous to the host cell. In some embodiments, at least two, at least three, at least four, or at least five enzymes are heterologous to the host cell. In some embodiments, at least one enzyme (e.g., thermostable enzyme) is endogenous (native) to the host cell. In some embodiments, at least two, at least three, at least four, or at least five enzymes are endogenous to the host cell.

The host cells may be prokaryotic cells, such as bacterial cells (e.g., *Escherichia coli* cells), or eukaryotic cells, such as yeast cells or plant cells. Other cell types are described below.

In some embodiments, at least one of the enzymes used to convert starch and/or cellodextrin to ribulose is a thermostable enzyme. In some embodiments, at least two, at least three, at least four, or at least five of the enzymes are thermostable enzymes. In some embodiments, all of the enzymes are thermostable enzymes. Thus, in some embodiments, the methods include culturing cells engineered to express at least one thermostable α-glucan phosphorylase, at least one thermostable phosphoglucomutase, at least one thermostable glucose 6-phosphate dehydrogenase, at least one thermostable 6-phosphogluconolactonase, at least one thermostable 6-phosphogluconate dehydrogenase, at least one thermostable ribulose 5-phosphate phosphatase, or a combination of at least two or more of the foregoing thermostable enzymes. In some embodiments, the methods include culturing cells engineered to express at least one thermostable cellodextrin phosphorylase, at least one thermostable phosphoglucomutase, at least one thermostable glucose 6-phosphate dehydrogenase, at least one thermostable 6-phosphogluconolactonase, at least one thermostable 6-phosphogluconate dehydrogenase, at least one thermostable ribulose 5-phosphate phosphatase, or a combination of at least two or more of the foregoing thermostable enzymes.

In some embodiments, the methods of producing ribulose include lysing (e.g., thermal, mechanical, chemical, or enzymatic lysis) the cultured cells to produce at least one (e.g., at least two, at least three, or at least four) cell lysate. It should be understood that multiple cell lysates (and thus multiple cell populations, e.g., from the same organism (e.g., bacteria) or from different organisms (e.g., bacteria, yeast and or plant cells)) may be used in an enzymatic reaction as provided herein. For example, one cell population may be engineered to express one or more enzymes(s) of the ribulose production pathway, while another cell population (or several other cell populations) may be engineered to express another (at least one other) enzyme of the ribulose production pathway. Thus, in some embodiments, the methods comprise culturing at least one population of cells engineered to express at least one α-glucan phosphorylase, culturing at least one cell population engineered to express at least one phosphoglucomutase, culturing at least one cell population engineered to express at least one glucose 6-phosphate dehydrogenase, culturing at least one cell population engineered to express at least one 6-phosphogluconolactonase, culturing at least one cell population engineered to express at least one 6-phosphogluconate dehydrogenase, and/or culturing at least one cell population engineered to express at least one ribulose 5-phosphate phosphatase. In some embodiments, the methods comprise culturing at least one population of cells engineered to express at least one cellodextrin phosphorylase, culturing at least one cell population engineered to express at least one phosphoglucomutase, culturing at least one cell population engineered to express at least one glucose 6-phosphate dehydrogenase, culturing at least one cell population engineered to express at least one 6-phosphogluconolactonase, culturing at least one cell population engineered to express at least one 6-phosphogluconate dehydrogenase, and/or culturing at least one cell population engineered to express at least one ribulose 5-phosphate phosphatase. Following lysis of the cells, the cell lysates are combined such that the enzymes are present in a single cell lysate/reaction mixture.

In some embodiments, the methods further include heating the cell lysate(s) (or a cell lysate mixture) to a temperature that inactivates undesired native enzymatic activities but does not inactivate any of the thermostable enzymes of the production pathway, to produce a heat-inactivated lysate. The cell lysate(s), in some embodiments, is heated to a temperature of at least 50° C. For example, the cell lysate(s) may be heated to a temperature of at least 55° C., 60° C., 65° C., 70° C., 75° C., 80° C., 85° C., or 90° C.

The cell lysate(s) may be heated for a period of time sufficient to inactive native enzymes (or other non-thermostable enzymes) of the cell. For example, the cell lysate(s) may be heated for at least 2, 3, 4, or at least 5 minutes. In some embodiments, the cell lysate(s) are heated for longer than 5 minutes. In some embodiments, the cell lysate(s) are heated for a period of time sufficient to reduce the activity of native enzymes (or other non-thermostable enzymes) by at least 50% (e.g., at least 60%, 70%, 80%, or 90%).

Following heat inactivation, in some embodiments, at least one (e.g., at least two or at least three) purified enzymes is added to the cell lysate/reaction mixture. Thus, a reaction mixture, in some embodiments, includes a combination of enzymes present in the cell lysate (expressed by the engineered host cell(s)) and at least one purified enzyme. At least one purified enzyme may be selected from the group consisting of α-glucan phosphorylases or cellodextrin phosphorylases, phosphoglucomutases, glucose 6-phosphate dehydrogenases, 6-phosphogluconolactonases, 6-phosphogluconate dehydrogenases, and ribulose 5-phosphate phosphatases.

In some embodiments, the methods also include incubating the heat-inactivated lysate(s) in the presence of a starch and inorganic phosphate to produce ribulose. In some embodiments, the methods also include incubating the heat-inactivated lysate(s) in the presence of a cellodextrin and inorganic phosphate to produce ribulose. In some embodiments, the heat-inactivated lysates are incubated at a temperature of at least 50 C. In some embodiments, the heat-inactivated lysates are incubated for at least 2 minutes (e.g., at least 3, 4, or 5 minutes). For example, the heat-inactivated lysates may be incubated for 2-5 minutes, or 2-10 minutes. The starch may be, for example, amylose, amylopectin, or a mixture of amylose and amylopectin. In some embodiments, biomass is used instead of starch. In these embodiments, the reaction includes cellodextrin phosphorylase(s). In some embodiments, the starch or cellodextrin is present as a component of a compound.

Also provided herein are cells and cell lysates used for the production of ribulose. Thus, an engineered cell (e.g., bacterial cell and/or yeast cell) or cell lysate(s) of the present disclosure may include at least one (e.g., at least two or at least three) enzyme selected from the group consisting of α-glucan phosphorylases, phosphoglucomutases, glucose 6-phosphate dehydrogenases, 6-phosphogluconolactonases, 6-phosphogluconate dehydrogenases, and ribulose 5-phosphate phosphatases. An engineered cell (e.g., bacterial cell and/or yeast cell) or cell lysate(s) of the present disclosure may include at least one (e.g., at least two or at least three) enzyme selected from the group consisting of cellodextrin phosphorylases, phosphoglucomutases, glucose 6-phosphate dehydrogenases, 6-phosphogluconolactonases, 6-phosphogluconate dehydrogenases, and ribulose 5-phosphate phosphatases. In some embodiments, an engineered cell (e.g., bacterial cell and/or yeast cell) or cell lysate(s) of the present disclosure includes at least one (e.g., at least two or at least three) enzyme selected from the group consisting of thermostable α-glucan phosphorylases, thermostable phosphoglucomutases, thermostable glucose 6-phosphate dehydrogenases, thermostable 6-phosphogluconolactonases, thermostable 6-phosphogluconate dehydrogenases, and thermostable ribulose 5-phosphate phosphatases. In some embodiments, an engineered cell (e.g., bacterial cell and/or yeast cell) or cell lysate(s) of the present disclosure includes at least one (e.g., at least two or at least three) enzyme selected from the group consisting of thermostable cellodextrin phosphorylases, thermostable phosphoglucomutases, thermostable glucose 6-phosphate dehydrogenases, thermostable 6-phosphogluconolactonases, thermostable 6-phosphogluconate dehydrogenases, and thermostable ribulose 5-phosphate phosphatases.

Ribose Production

Further still, some aspects of the present disclosure provide methods, compositions, and systems for producing ribose. These methods, in some embodiments, include culturing cells engineered to express at least one α-glucan phosphorylase and/or at least one cellodextrin phosphorylase, at least one phosphoglucomutase, at least one glucose 6-phosphate dehydrogenase, at least one 6-phosphogluconolactonase, at least one 6-phosphogluconate dehydrogenase, at least one ribose 5-phosphate isomerase, at least one ribose 5-phosphate phosphatase, or a combination of at least two of the foregoing enzymes. In some embodiments, the α-glucan phosphorylase (and/or cellodextrin phosphorylase) and the phosphoglucomutase are expressed as a single fusion (chimeric) protein or a bifunctional protein.

Enzymes of the ribose production pathways as provided herein are typically heterologous to the host cell (initially cloned from or obtained from a different cell type), although some of the enzymes may be endogenous (native) to the host cell. Thus, in some embodiments, at least one enzyme (e.g., thermostable enzyme) used to convert starch and/or cellodextrin to ribose is heterologous to the host cell. In some embodiments, at least two, at least three, at least four, at least five, or at least six enzymes are heterologous to the host cell. In some embodiments, at least one enzyme (e.g., thermostable enzyme) is endogenous (native) to the host cell. In some embodiments, at least two, at least three, at least four, at least five, or at least six enzymes are endogenous to the host cell.

The host cells may be prokaryotic cells, such as bacterial cells (e.g., *Escherichia coli* cells), or eukaryotic cells, such as yeast cells or plant cells. Other cell types are described below.

In some embodiments, at least one of the enzymes used to convert starch and/or cellodextrin to ribose is a thermostable enzyme. In some embodiments, at least two, at least three, at least four, at least five, or at least six of the enzymes are thermostable enzymes. In some embodiments, all of the enzymes are thermostable enzymes. Thus, in some embodiments, the methods include culturing cells engineered to express at least one thermostable α-glucan phosphorylase, at least one thermostable phosphoglucomutase, at least one thermostable glucose 6-phosphate dehydrogenase, at least one thermostable 6-phosphogluconolactonase, at least one thermostable 6-phosphogluconate dehydrogenase, at least one thermostable ribose 5-phosphate isomerase, at least one thermostable ribose 5-phosphate phosphatase, or a combination of at least two or more of the foregoing thermostable enzymes. In some embodiments, the methods include culturing cells engineered to express at least one thermostable cellodextrin phosphorylase, at least one thermostable phosphoglucomutase, at least one thermostable glucose 6-phosphate dehydrogenase, at least one thermostable 6-phosphogluconolactonase, at least one thermostable 6-phosphogluconate dehydrogenase, at least one thermostable ribose 5-phosphate isomerase, at least one thermostable ribose 5-phosphate phosphatase, or a combination of at least two or more of the foregoing thermostable enzymes.

In some embodiments, the methods of producing ribose include lysing (e.g., thermal, mechanical, chemical, or enzymatic lysis) the cultured cells to produce at least one (e.g., at least two, at least three, or at least four) cell lysate. It should be understood that multiple cell lysates (and thus multiple cell populations, e.g., from the same organism (e.g., bacteria) or from different organisms (e.g., bacteria, yeast and or plant cells)) may be used in an enzymatic reaction as provided herein. For example, one cell population may be engineered to express one or more enzymes(s) of the ribose production pathway, while another cell population (or several other cell populations) may be engineered to express another (at least one other) enzyme of the ribose production pathway. Thus, in some embodiments, the methods comprise culturing at least one population of cells engineered to express at least one α-glucan phosphorylase, culturing at least one cell population engineered to express at least one phosphoglucomutase, culturing at least one cell population engineered to express at least one glucose 6-phosphate dehydrogenase, culturing at least one cell population engineered to express at least one 6-phosphogluconolactonase, culturing at least one cell population engineered to express at least one 6-phosphogluconate dehydrogenase, culturing at least one cell population engineered to express at least one ribose 5-phosphate isomerase, and/or culturing at least one cell population engineered to express at least one ribose 5-phosphate phosphatase. In some embodiments, the methods comprise culturing at least one population of cells engineered to express at least one cellodextrin phosphorylase, culturing at least one cell population engineered to express at least one phosphoglucomutase, culturing at least one cell population engineered to express at least one glucose 6-phosphate dehydrogenase, culturing at least one cell population engineered to express at least one 6-phosphogluconolactonase, culturing at least one cell population engineered to express at least one 6-phosphogluconate dehydrogenase, culturing at least one cell population engineered to express at least one ribose 5-phosphate isomerase, and/or culturing at least one cell population engineered to express at least one ribose 5-phosphate phosphatase. Following lysis of the cells, the cell lysates are combined such that the enzymes are present in a single cell lysate/reaction mixture.

In some embodiments, the methods further include heating the cell lysate(s) (or a cell lysate mixture) to a temperature that inactivates undesired native enzymatic activities but does not inactivate any of the thermostable enzymes of the production pathway, to produce a heat-inactivated lysate. The cell lysate(s), in some embodiments, is heated to a temperature of at least 50° C. For example, the cell lysate(s) may be heated to a temperature of at least 55° C., 60° C., 65° C., 70° C., 75° C., 80° C., 85° C., or 90° C.

The cell lysate(s) may be heated for a period of time sufficient to inactive native enzymes (or other non-thermostable enzymes) of the cell. For example, the cell lysate(s) may be heated for at least 2, 3, 4, or at least 5 minutes. In some embodiments, the cell lysate(s) are heated for longer than 5 minutes. In some embodiments, the cell lysate(s) are heated for a period of time sufficient to reduce the activity of native enzymes (or other non-thermostable enzymes) by at least 50% (e.g., at least 60%, 70%, 80%, or 90%).

Following heat inactivation, in some embodiments, at least one (e.g., at least two or at least three) purified enzymes is added to the cell lysate/reaction mixture. Thus, a reaction mixture, in some embodiments, includes a combination of enzymes present in the cell lysate (expressed by the engineered host cell(s)) and at least one purified enzyme. At least one purified enzyme may be selected from the group consisting of α-glucan phosphorylases or cellodextrin phosphorylases, phosphoglucomutases, glucose 6-phosphate dehydrogenases, 6-phosphogluconolactonases, 6-phosphogluconate dehydrogenases, ribose 5-phosphate isomerases, and ribose 5-phosphate phosphatases.

In some embodiments, the methods also include incubating the heat-inactivated lysate(s) in the presence of a starch and inorganic phosphate to produce ribose. In some embodiments, the methods also include incubating the heat-inactivated lysate(s) in the presence of a cellodextrin and inorganic phosphate to produce ribose. In some embodiments, the heat-inactivated lysates are incubated at a temperature of at least 50 C. In some embodiments, the heat-inactivated lysates are incubated for at least 2 minutes (e.g., at least 3, 4, or 5 minutes). For example, the heat-inactivated lysates may be incubated for 2-5 minutes, or 2-10 minutes. The starch may be, for example, amylose, amylopectin, or a mixture of amylose and amylopectin. In some embodiments, biomass is used instead of starch. In these embodiments, the reaction includes cellodextrin phosphorylase(s). In some embodiments, the starch or cellodextrin is present as a component of a compound.

Also provided herein are cells and cell lysates used for the production of ribose. Thus, an engineered cell (e.g., bacterial cell and/or yeast cell) or cell lysate(s) of the present disclosure may include at least one (e.g., at least two, at least three, at least four, at least five, or at least six) enzyme selected from the group consisting of α-glucan phosphorylases, phosphoglucomutases, glucose 6-phosphate dehydrogenases, 6-phosphogluconolactonases, 6-phosphogluconate dehydrogenases, ribose 5-phosphate isomerases, and ribose 5-phosphate phosphatases. An engineered cell (e.g., bacterial cell and/or yeast cell) or cell lysate(s) of the present disclosure may include at least one (e.g., at least two, at least three, at least four, at least five, or at least six) enzyme selected from the group consisting of cellodextrin phosphorylases, phosphoglucomutases, glucose 6-phosphate dehydrogenases, 6-phosphogluconolactonases, 6-phosphogluconate dehydrogenases, ribose 5-phosphate isomerases, and ribose 5-phosphate phosphatases. In some embodiments, an engineered cell (e.g., bacterial cell and/or yeast cell) or cell lysate(s) of the present disclosure includes at least one (e.g., at least two, at least three, at least four, at least five, or at least six) enzyme selected from the group consisting of thermostable α-glucan phosphorylases, thermostable phosphoglucomutases, thermostable glucose 6-phosphate dehydrogenases, thermostable 6-phosphogluconolactonases, thermostable 6-phosphogluconate dehydrogenases, thermostable ribose 5-phosphate isomerases, and thermostable ribose 5-phosphate phosphatases. some embodiments, an engineered cell (e.g., bacterial cell and/or yeast cell) or cell lysate(s) of the present disclosure includes at least one (e.g., at least two, at least three, at least four, at least five, or at least six) enzyme selected from the group consisting of thermostable cellodextrin phosphorylases, thermostable phosphoglucomutases, thermostable glucose 6-phosphate dehydrogenases, thermostable 6-phosphogluconolactonases, thermostable 6-phosphogluconate dehydrogenases, thermostable ribose 5-phosphate isomerases, and thermostable ribose 5-phosphate phosphatases.

Arabinose Production

Further still, some aspects of the present disclosure provide methods, compositions, and systems for producing arabinose. These methods, in some embodiments, include culturing cells engineered to express at least one α-glucan phosphorylase and/or at least one cellodextrin phosphorylase, at least one phosphoglucomutase, at least one glucose 6-phosphate dehydrogenase, at least one 6-phosphogluconolactonase, at least one 6-phosphogluconate dehydrogenase, at least one arabinose 5-phosphate isomerase, at least one arabinose 5-phosphate phosphatase, or a combination of at least two of the foregoing enzymes. In some embodiments, the α-glucan phosphorylase (and/or cellodextrin phosphorylase) and the phosphoglucomutase are expressed as a single fusion (chimeric) protein or a bifunctional protein.

Enzymes of the arabinose production pathways as provided herein are typically heterologous to the host cell (initially cloned from or obtained from a different cell type), although some of the enzymes may be endogenous (native) to the host cell. Thus, in some embodiments, at least one enzyme (e.g., thermostable enzyme) used to convert starch and/or cellodextrin to arabinose is heterologous to the host cell. In some embodiments, at least two, at least three, at least four, at least five, or at least six enzymes are heterologous to the host cell. In some embodiments, at least one enzyme (e.g., thermostable enzyme) is endogenous (native) to the host cell. In some embodiments, at least two, at least three, at least four, at least five, or at least six enzymes are endogenous to the host cell.

The host cells may be prokaryotic cells, such as bacterial cells (e.g., *Escherichia coli* cells), or eukaryotic cells, such as yeast cells or plant cells. Other cell types are described below.

In some embodiments, at least one of the enzymes used to convert starch and/or cellodextrin to arabinose is a thermostable enzyme. In some embodiments, at least two, at least three, at least four, at least five, or at least six of the enzymes are thermostable enzymes. In some embodiments, all of the enzymes are thermostable enzymes. Thus, in some embodiments, the methods include culturing cells engineered to express at least one thermostable α-glucan phosphorylase, at least one thermostable phosphoglucomutase, at least one thermostable glucose 6-phosphate dehydrogenase, at least one thermostable 6-phosphogluconolactonase, at least one thermostable 6-phosphogluconate dehydrogenase, at least one thermostable arabinose 5-phosphate isomerase, at least one thermostable arabinose 5-phosphate phosphatase, or a combination of at least two or more of the foregoing thermostable enzymes. In some embodiments, the methods include culturing cells engineered to express at least one thermostable cellodextrin phosphorylase, at least one thermostable phosphoglucomutase, at least one thermostable glucose 6-phosphate dehydrogenase, at least one thermostable 6-phosphogluconolactonase, at least one thermostable 6-phosphogluconate dehydrogenase, at least one thermostable arabinose 5-phosphate isomerase, at least one thermostable arabinose 5-phosphate phosphatase, or a combination of at least two or more of the foregoing thermostable enzymes.

In some embodiments, the methods of producing arabinose include lysing (e.g., thermal, mechanical, chemical, or enzymatic lysis) the cultured cells to produce at least one (e.g., at least two, at least three, or at least four) cell lysate. It should be understood that multiple cell lysates (and thus multiple cell populations, e.g., from the same organism (e.g., bacteria) or from different organisms (e.g., bacteria, yeast and or plant cells)) may be used in an enzymatic reaction as provided herein. For example, one cell population may be engineered to express one or more enzymes(s) of the arabinose production pathway, while another cell population (or several other cell populations) may be engineered to express another (at least one other) enzyme of the arabinose production pathway. Thus, in some embodiments, the methods comprise culturing at least one population of cells engineered to express at least one α-glucan phosphorylase, culturing at least one cell population engineered to express at least one phosphoglucomutase, culturing at least one cell population engineered to express at least one glucose 6-phosphate dehydrogenase, culturing at least one cell population engineered to express at least one 6-phosphogluconolactonase, culturing at least one cell population engineered to express at least one 6-phosphogluconate dehydrogenase, culturing at least one cell population engineered to express at least one arabinose 5-phosphate isomerase, and/or culturing at least one cell population engineered to express at least one arabinose 5-phosphate phosphatase. In some embodiments, the methods comprise culturing at least one population of cells engineered to express at least one cellodextrin phosphorylase, culturing at least one cell population engineered to express at least one phosphoglucomutase, culturing at least one cell population engineered to express at least one glucose 6-phosphate dehydrogenase, culturing at least one cell population engineered to express at least one 6-phosphogluconolactonase, culturing at least one cell population engineered to express at least one 6-phosphogluconate dehydrogenase, culturing at least one cell population engineered to express at least one arabinose 5-phosphate isomerase, and/or culturing at least one cell population engineered to express at least one arabinose 5-phosphate phosphatase. Following lysis of the cells, the cell lysates are combined such that the enzymes are present in a single cell lysate/reaction mixture.

In some embodiments, the methods further include heating the cell lysate(s) (or a cell lysate mixture) to a temperature that inactivates undesired native enzymatic activities but does not inactivate any of the thermostable enzymes of the production pathway, to produce a heat-inactivated lysate. The cell lysate(s), in some embodiments, is heated to a temperature of at least 50° C. For example, the cell lysate(s) may be heated to a temperature of at least 55° C., 60° C., 65° C., 70° C., 75° C., 80° C., 85° C., or 90° C.

The cell lysate(s) may be heated for a period of time sufficient to inactive native enzymes (or other non-thermostable enzymes) of the cell. For example, the cell lysate(s) may be heated for at least 2, 3, 4, or at least 5 minutes. In some embodiments, the cell lysate(s) are heated for longer than 5 minutes. In some embodiments, the cell lysate(s) are heated for a period of time sufficient to reduce the activity of native enzymes (or other non-thermostable enzymes) by at least 50% (e.g., at least 60%, 70%, 80%, or 90%).

Following heat inactivation, in some embodiments, at least one (e.g., at least two or at least three) purified enzymes is added to the cell lysate/reaction mixture. Thus, a reaction mixture, in some embodiments, includes a combination of enzymes present in the cell lysate (expressed by the engineered host cell(s)) and at least one purified enzyme. At least one purified enzyme may be selected from the group consisting of α-glucan phosphorylases or cellodextrin phosphorylases, phosphoglucomutases, glucose 6-phosphate dehydrogenases, 6-phosphogluconolactonases, 6-phosphogluconate dehydrogenases, arabinose 5-phosphate isomerases, and arabinose 5-phosphate phosphatases.

In some embodiments, the methods also include incubating the heat-inactivated lysate(s) in the presence of a starch and inorganic phosphate to produce arabinose. In some embodiments, the methods also include incubating the heat-inactivated lysate(s) in the presence of a cellodextrin and inorganic phosphate to produce arabinose. In some embodiments, the heat-inactivated lysates are incubated at a temperature of at least 50 C. In some embodiments, the heat-inactivated lysates are incubated for at least 2 minutes (e.g., at least 3, 4, or 5 minutes). For example, the heat-inactivated lysates may be incubated for 2-5 minutes, or 2-10 minutes. The starch may be, for example, amylose, amylopectin, or a mixture of amylose and amylopectin. In some embodiments, biomass is used instead of starch. In these embodiments, the reaction includes cellodextrin phosphorylase(s). In some embodiments, the starch or cellodextrin is present as a component of a compound.

Also provided herein are cells and cell lysates used for the production of arabinose. Thus, an engineered cell (e.g., bacterial cell and/or yeast cell) or cell lysate(s) of the present disclosure may include at least one (e.g., at least two, at least three, at least four, at least five, or at least six) enzyme selected from the group consisting of α-glucan phosphorylases, phosphoglucomutases, glucose 6-phosphate dehydrogenases, 6-phosphogluconolactonases, 6-phosphogluconate dehydrogenases, arabinose 5-phosphate isomerases, and arabinose 5-phosphate phosphatases. An engineered cell (e.g., bacterial cell and/or yeast cell) or cell lysate(s) of the present disclosure may include at least one (e.g., at least two, at least three, at least four, at least five, or at least six) enzyme selected from the group consisting of cellodextrin phosphorylases, phosphoglucomutases, glucose 6-phosphate dehydrogenases, 6-phosphogluconolactonases, 6-phosphogluconate dehydrogenases, arabinose 5-phosphate isomerases, and arabinose 5-phosphate phosphatases. In some embodiments, an engineered cell (e.g., bacterial cell and/or yeast cell) or cell lysate(s) of the present disclosure includes at least one (e.g., at least two, at least three, at least four, at least five, or at least six) enzyme selected from the group consisting of thermostable α-glucan phosphorylases, thermostable phosphoglucomutases, thermostable glucose 6-phosphate dehydrogenases, thermostable 6-phosphogluconolactonases, thermostable 6-phosphogluconate dehydrogenases, thermostable arabinose 5-phosphate isomerases, and thermostable arabinose 5-phosphate phosphatases. In some embodiments, an engineered cell (e.g., bacterial cell and/or yeast cell) or cell lysate(s) of the present disclosure includes at least one (e.g., at least two, at least three, at least four, at least five, or at least six) enzyme selected from the group consisting of thermostable cellodextrin phosphorylases, thermostable phosphoglucomutases, thermostable glucose 6-phosphate dehydrogenases, thermostable 6-phosphogluconolactonases, thermostable 6-phosphogluconate dehydrogenases, thermostable arabinose 5-phosphate isomerases, and thermostable arabinose 5-phosphate phosphatases.

Substrate Flexibility and Debranching Enzymes

For all pathways described herein, a multitude of polymeric glucose substrates can be used. Non-limiting examples of polymeric glucose substrates include starch, glycogen, and cellodextrin. In some embodiments, the substrate is starch. In other embodiments, the substrate is glycogen. In still other embodiments, the substrate is cellodextrin. In some embodiments, a partially hydrolyzed version of a polymeric glucose substrate (e.g., starch, glycogen, or cellulose/cellodextrin) is used. Starch and glycogen include a plurality of glucose monomers linked primarily by α(1-4) bonds, while cellodextrin includes the same glucose monomers linked by β(1-4) bonds. One other major difference between cellodextrin and the other two substrates is the existence of α(1-6) branches off of the α(1-4) chains. Both starch and glycogen contain these branch points, although glycogen is substantially more branched than starch. For the α(1-4) polymers, α-glucan phosphorylases, also referred to as α-glucan phosphorylases or glycogen phosphorylases depending on substrate preference, consume the polymers one glucose at a time releasing glucose 1-phosphate. For cellodextrin, cellodextrin phosphorylase performs the same reaction, also releasing glucose 1-phosphate.

Long polymers of starch and cellulose/cellodextrin are often insoluble in aqueous solutions and in addition to precipitating out, can cause gelling and retrogradation of the solution. When starch and cellulose/cellodextrin are partially hydrolyzed to smaller chain length polymers, either through chemical (e.g., acid hydrolysis) or enzymatic (e.g., α-amylase) methods, the resulting products are maltodextrins and cellodextrins for starch and cellulose, respectively. These hydrolyzed derivatives often solubilize and mix better than their parent molecules, and thus, in some embodiments, are used in the pathways provided herein.

For glycogen, starch, or hydrolyzed maltodextrins, α(1-6) branches will substantially reduce yields of any sugar pathway, as the glucan phosphorylase chew the polymers down to the end of their branches, leaving a large central core of available glucose unconverted. For these substrates/pathways, debranching enzymes may be used to increase substrate availability to the glucan phosphorylase. There are two exemplary classes of debranching enzymes that can be used—isoamylases and pullulanases (see, e.g., Table 3). Enzymatically, both classes perform the same function but differ in substrate specificity. While using the debranching enzyme increases yields, the timing of the use will depend on the process and substrates being used. In some embodiments, an α-glucan is pretreated with α-amylase and a debranching enzyme, and then the resulting debranched maltodextrin(s) is fed into a reactor with the other pathway enzymes. In other embodiments, the debranching occurs concurrent with the pathway and branched α-glucans is fed into the reaction containing all pathway enzymes as well as the debranching enzyme.

TABLE 3

Exemplary Debranching Enzymes

| Enzyme Name | EC No. | Native Organism | NCBI No. |
|---|---|---|---|
| Pullulanase | 3.2.1.41 | *Fervidobacterium pennavorans* | AAD30387 |
| | | *Thermotoga* sp. RQ5 | WP_012310857 |
| | | *Bacillus flavocaldarius* | BAB18516 |
| | | *Thermosipho africanus* | WP_004100450 |
| | | *Kosmotoga olearia* | WP_015868997 |

TABLE 3-continued

Exemplary Debranching Enzymes

| Enzyme Name | EC No. | Native Organism | NCBI No. |
|---|---|---|---|
| Isoamylase | 3.2.1.68 | *Sulfolobus tokodaii* | BAB65940 |
| | | *Metallosphaera hakonensis* | AAS00512 |
| | | *Sphaerobacter thermophilus* | WP_012873143 |
| | | *Bacillus lentus* | AGL34022 |

Cell-Free Production

"Cell-free production" is the use of biological processes for the synthesis of a biomolecule or chemical compound without using living cells. Rather, the cells are lysed and unpurified (crude) portions, containing enzymes, are used for the production of a desired product. As a non-limiting example, cells are cultured, harvested, and lysed by high-pressure homogenization. The cell-free reaction may be conducted in a batch or fed-batch mode. In some instances, the biological reaction networks fill the working volume of the reactor and may be more dilute than the intracellular environment. Yet substantially all of the cellular catalysts are provided, including catalysts that are membrane associated. The inner membrane is fragmented during cell lysis, and the fragments of these membranes form functional membrane vesicles. Thus, complex biotransformations are effected by catalysis. See, e.g., Swartz, *AIChE Journal,* 2012, 58(1), 5-13, incorporated herein by reference.

Cell-free methods and systems of the present disclosure, in some embodiments, utilize cell lysates (e.g., crude or partially purified cell lysates), discussed in greater detail herein. Cell lysates may be prepared, for example, by mechanical means (e.g., shearing or crushing). In some embodiments, cell lysates are distinct from chemically-permeabilized cells. As discussed here, in some embodiments, during cell lysis (e.g., mechanical cell lysis), the inner cell membrane is fragmented such that inverted membrane vesicles are formed in the cells lysates. Cells that are lysed (e.g., at least 75%, 80%, 85%, 90%, or 95%) are no longer intact.

In some embodiments, permeabilized cells are used. Permeabilized cells are intact cells containing perforations (small holes). In some embodiments, cells may be permeabilized to release the cell content for use in a reaction as provided herein.

In some embodiments, partially purified cell fractions are used. A partially purified cell fraction is a cell lysate from which one or more cellular components (e.g., cell membranes) have been partially or completely removed.

Thermostable Enzymes

An enzyme is considered thermostable if the enzyme (a) retains a substantial portion of its activity after exposure to high temperatures that denature other native enzymes or (b) functions at a relatively high rate after exposure to a medium to high temperature where native enzymes function at low rates.

In some embodiments, a thermostable enzyme retains greater than 50% activity following exposure to relatively high temperature that would otherwise denature a similar (non-thermostable) native enzyme. In some embodiments, a thermostable enzyme retains 50-100% activity following exposure to relatively high temperature that would otherwise denature a similar (non-thermostable) native enzyme. For example, a thermostable enzyme may retain 50-90%, 50-85%, 50-80%, 50-75%, 50-70%, 50-65%, 50-60%, or 50-55% of its activity following exposure to relatively high temperature that would otherwise denature a similar (non-thermostable) native enzyme. In some embodiments, a thermostable enzyme retains 25%, 30%, 35%, 40%, 45%, 50%, 55%, 60%, 65%, 70%, 75%, 80%, 85%, 90%, 95%, 98%, 99%, or 100% of its activity following exposure to relatively high temperature that would otherwise denature a similar (non-thermostable) native enzyme.

In some embodiments, the activity of a thermostable enzyme after exposure medium to high temperature is greater than (e.g., 25%, 30%, 35%, 40%, 45%, 50%, 55%, 60%, 65%, 70%, 75%, 80%, 85%, 90%, 95%, 98%, 99%, or 100% greater than) the activity of a similar (non-thermostable) native enzyme.

Thermostable enzymes (e.g., phosphatases or phosphorylases) may remain active (able to catalyze a reaction), for example, at temperatures of 45° C. to 80° C., or higher. In some embodiments, thermostable enzymes remain active at a temperature of 45-80° C., 45-70° C., 45-60° C., 45-50° C., 50-80° C., 50-70° C., 50-60° C., 60-80° C., 60-70° C., or 70-80° C. For example, thermostable enzymes may remain active at a temperature of 45° C., 46° C., 47° C., 48° C., 49° C., 50° C., 51° C., 52° C., 53° C., 54° C., 55° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C. Thermostable enzymes may remain active at relatively high temperatures for 15 minutes to 48 hours, or longer, after exposure to relatively high temperatures. For example, thermostable enzymes may remain active at relatively high temperatures for 1, 2, 3, 4, 5, 6, 7, 8, 9, 10, 11, 12, 13, 14, 15, 16, 17, 18, 19, 20, 24, 36, 42, or 48 hours.

Engineered Cells

Engineered cells of the present disclosure, in some embodiments, comprise at least one, or all, of the enzymatic activities required to convert a starch and/or cellulose/cellodextrin to a sugar. "Engineered cells" are cells that comprise at least one engineered (e.g., recombinant or synthetic) nucleic acid, or are otherwise modified such that they are structurally and/or functionally distinct from their naturally-occurring counterparts. Thus, a cell that contains an engineered nucleic acid is considered an "engineered cell."

Engineered cells of the present disclosure, in some embodiments, comprise a α-glucan phosphorylase (e.g., a thermostable α-glucan phosphorylase) and/or a cellodextrin phosphorylase (e.g., a thermostable cellodextrin phosphorylase), a phosphoglucomutase (e.g., a thermostable phosphoglucomutase), and at least one enzyme (e.g., thermostable enzyme) selected from the group consisting of isomerases, epimerases, dehydrogenases, and sugar phosphatases.

Engineered cells, in some embodiments, express selectable markers. Selectable markers are typically used to select engineered cells that have taken up and express an engineered nucleic acid following transfection of the cell (or following other procedure used to introduce foreign nucleic acid into the cell). Thus, a nucleic acid encoding product may also encode a selectable marker. Examples of selectable markers include, without limitation, genes encoding proteins that increase or decrease either resistance or sensitivity to antibiotics (e.g., ampicillin resistance genes, kanamycin resistance genes, neomycin resistance genes, tetracycline resistance genes and chloramphenicol resistance genes) or other compounds. Other selectable markers may be used in accordance with the present disclosure.

An engineered cell "expresses" a product if the product, encoded by a nucleic acid (e.g., an engineered nucleic acid), is produced in the cell. It is known in the art that gene expression refers to the process by which genetic instructions in the form of a nucleic acid are used to synthesize a product, such as a protein (e.g., an enzyme).

Engineered cells may be prokaryotic cells or eukaryotic cells. In some embodiments, engineered cells are bacterial cells, yeast cells, insect cells, mammalian cells, or other types of cells.

Engineered bacterial cells useful in the present disclosure include, without limitation, engineered *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Therms* spp., *Stenotrophomonas* spp., *Chromobacterium* spp., *Sinorhizobium* spp., *Saccharopolyspora* spp., *Agrobacterium* spp., *Vibrio* spp., and *Pantoea* spp.

Engineered yeast cells useful in the present disclosure include, without limitation, engineered *Saccharomyces* spp., *Schizosaccharomyces, Hansenula, Candida, Kluyveromyces, Yarrowia* and *Pichia*.

In some embodiments, engineered cells useful in the present disclosure are engineered *Escherichia coli* cells, *Bacillus subtilis* cells, *Pseudomonas putida* cells, *Saccharomyces cerevisiae* cells, and/or *Lactobacillus brevis* cells. In some embodiments, engineered cells useful in the present disclosure are engineered *Escherichia coli* cells.

Engineered Nucleic Acids

A "nucleic acid" is at least two nucleotides covalently linked together, and in some instances, may contain phosphodiester bonds (e.g., a phosphodiester "backbone"). Nucleic acids (e.g., components, or portions, of nucleic acids) may be naturally occurring or engineered. "Naturally occurring" nucleic acids are present in a cell that exists in nature in the absence of human intervention. "Engineered nucleic acids" include recombinant nucleic acids and synthetic nucleic acids. A "recombinant nucleic acid" refers to a molecule that is constructed by joining nucleic acid molecules (e.g., from the same species or from different species) and, typically, can replicate in a living cell. A "synthetic nucleic acid" refers to a molecule that is biologically synthesized, chemically synthesized, or by other means synthesized or amplified. A synthetic nucleic acid includes nucleic acids that are chemically modified or otherwise modified but can base pair with naturally-occurring nucleic acid molecules. Recombinant and synthetic nucleic acids also include those molecules that result from the replication of either of the foregoing. Engineered nucleic acids may contain portions of nucleic acids that are naturally occurring, but as a whole, engineered nucleic acids do not occur naturally and require human intervention. In some embodiments, a nucleic acid encoding a product of the present disclosure is a recombinant nucleic acid or a synthetic nucleic acid. In other embodiments, a nucleic acid encoding a product is naturally occurring.

An engineered nucleic acid encoding enzymes, as provided herein, may be operably linked to a "promoter," which is a control region of a nucleic acid at which initiation and rate of transcription of the remainder of a nucleic acid are controlled. A promoter drives expression or drives transcription of the nucleic acid that it regulates.

A promoter may be one naturally associated with a gene or sequence, as may be obtained by isolating the 5' noncoding sequences located upstream of the coding segment of a given gene or sequence. Such a promoter can be referred to as "endogenous."

In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR).

A promoter is considered to be "operably linked" when it is in a correct functional location and orientation in relation to the nucleic acid it regulates to control ("drive") transcriptional initiation and/or expression of that nucleic acid.

Engineered nucleic acids of the present disclosure may contain a constitutive promoter or an inducible promoter. A "constitutive promoter" refers to a promoter that is constantly active in a cell. An "inducible promoter" refers to a promoter that initiates or enhances transcriptional activity when in the presence of, influenced by, or contacted by an inducer or inducing agent, or activated in the absence of a factor that causes repression. Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters, steroid-regulated promoters, metal-regulated promoters, pathogenesis-regulated promoters, temperature/heat-inducible, phosphate-regulated (e.g., PhoA), and light-regulated promoters.

An inducer or inducing agent may be endogenous or a normally exogenous condition (e.g., light), compound (e.g., chemical or non-chemical compound) or protein that contacts an inducible promoter in such a way as to be active in regulating transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter.

Engineered nucleic acids may be introduced into host cells using any means known in the art, including, without limitation, transformation, transfection (e.g., chemical (e.g., calcium phosphate, cationic polymers, or liposomes) or non-chemical (e.g., electroporation, sonoporation, impalefection, optical transfection, hydro dynamic)), and transduction (e.g., viral transduction).

Enzymes or other proteins encoded by a naturally-occurring, intracellular nucleic acid may be referred to as "endogenous enzymes" or "endogenous proteins."

Protease Targeting

Engineered cells of the present disclosure may express (e.g., endogenously express) enzymes necessary for the health of the cells that may have a negative impact on the production of a sugar of interest (e.g., allulose). Such enzymes are referred to herein as "target enzymes." For example, target enzymes expressed by engineered cells may compete for substrates or cofactors with an enzyme that increases the rate of precursor supplied to an sugar production pathway. As another example, target enzymes expressed by the engineered cells may compete for substrates or cofactors with an enzyme that is a key pathway entry enzyme of an sugar production pathway. As yet another example, target enzymes expressed by the engineered cells may compete for substrates or cofactors with an enzyme that supplies a substrate or cofactor of an sugar production pathway.

To negate, or reduce, this negative impact, target enzymes can be modified to include a site-specific protease-recognition sequence in their protein sequence such that the target enzyme may be "targeted" and cleaved for inactivation during sugar production (see, e.g., U.S. Publication No. 2012/0052547 A1, published on Mar. 1, 2012; and International Publication No. WO 2015/021058 A2, published Feb. 12, 2015, each of which is incorporated by reference herein).

Cleavage of a target enzyme containing a site-specific protease-recognition sequence results from contact with a cognate site-specific protease that is sequestered in the periplasm of cell (separate from the target enzyme) during the cell growth phase (e.g., as engineered cells are cultured) and is brought into contact with the target enzyme during the conversion phase (e.g., following cell lysis to produce a cell lysate). Thus, engineered cells of the present disclosure comprise, in some embodiments, (i) an engineered nucleic acid encoding a target enzyme that negatively impacts the rate of conversion and includes a site-specific protease-recognition sequence in the protein sequence of the target enzyme, and (ii) an engineered nucleic acid encoding a site-specific protease that cleaves the site-specific protease-recognition sequence of the target enzyme and includes a periplasmic-targeting sequence. This periplasmic-targeting sequence is responsible for sequestering the site-specific protease to the periplasmic space of the cell until the cell is lysed. Examples of periplasmic-targeting sequences are provided below.

Examples of proteases that may be used in accordance with the present disclosure include, without limitation, alanine carboxypeptidase, astacin, bacterial leucyl aminopeptidase, cancer procoagulant, cathepsin B, clostripain, cytosol alanyl aminopeptidase, elastase, endoproteinase Brg-C, enterokinase, gastricsin, gelatinase, Gly-X carboxypeptidase, glycyl endopeptidase, human rhinovirus 3C protease, hypodermin C, Iga-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2B, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin B, venombin BB and Xaa-pro aminopeptidase.

Periplasmic Targeting

Enzymes of an sugar production pathway may include at least one enzyme that has a negative impact on the health (e.g., viability) of a cell. To negate or reduce this negative impact, an enzyme can be modified to include a relocation sequence such that the enzyme is relocated to a cellular or extra-cellular compartment where it is not naturally located and where the enzyme does not negatively impact the health of the cell (see, e.g., Publication No. US-2011-0275116-A1, published on Nov. 10, 2011, incorporated by reference herein). For example, an enzyme of an sugar production pathway may be relocated to the periplasmic space of a cell.

Thus, in some embodiments, engineered cells of the present disclosure comprise at least one enzyme of an sugar production pathway that is linked to a periplasmic-targeting sequence. A "periplasmic-targeting sequence" is an amino acid sequence that targets to the periplasm of a cell the protein to which it is linked. A protein that is linked to a periplasmic-targeting sequence will be sequestered in the periplasm of the cell in which the protein is expressed.

Periplasmic-targeting sequences may be derived from the N-terminus of bacterial secretory protein, for example. The sequences vary in length from about 15 to about 70 amino acids. The primary amino acid sequences of periplasmic-targeting sequences vary, but generally have a common structure, including the following components: (i) the N-terminal part has a variable length and generally carries a net positive charge; (ii) following is a central hydrophobic core of about 6 to about 15 amino acids; and (iii) the final component includes four to six amino acids which define the cleavage site for signal peptidases.

Periplasmic-targeting sequences of the present disclosure, in some embodiments, may be derived from a protein that is secreted in a Gram negative bacterium. The secreted protein may be encoded by the bacterium, or by a bacteriophage that infects the bacterium. Examples of Gram negative bacterial sources of secreted proteins include, without limitation, members of the genera *Escherichia, Pseudomonas, Klebsiella, Salmonella, Caulobacter, Methylomonas, Acetobacter, Achromobacter, Acinetobacter, Aeromonas, Agrobacterium, Alcaligenes, Azotobacter, Burkholderia, Citrobacter, Comamonas, Enterobacter, Erwinia, Rhizobium, Vibrio,* and *Xanthomonas.*

Examples of periplasmic-targeting sequences for use in accordance with the present disclosure include, without limitation, sequences selected from the group consisting of:

```
                            (SEQ ID NO: 1)
MKIKTGARILALSALTTMMFSASALA;

(SEQ ID NO: 2)
MKQSTIALALLPLLFTPVTKA;

(SEQ ID NO: 3)
MMITLRKLPLAVAVAAGVMSAQAMA;

(SEQ ID NO: 4)
MNKKVLTLSAVMASMLFGAAAHA;

(SEQ ID NO: 5)
MKYLLPTAAAGLLLLAAQPAMA;

(SEQ ID NO: 6)
MKKIWLALAGLVLAFSASA;

(SEQ ID NO: 7)
MMTKIKLLMLIIFYLIISASAHA;

(SEQ ID NO: 8)
MKQALRVAFGFLILWASVLHA;

(SEQ ID NO: 9)
MRVLLFLLLSLFMLPAFS;
and (SEQ ID NO: 10)
MANNDLFQASRRRFLAQLGGLTVAGMLGPSLLTPRRATA.
```

Cell Cultures and Cell Lysates

Typically, engineered cells are cultured. "Culturing" refers to the process by which cells are grown under controlled conditions, typically outside of their natural environment. For example, engineered cells, such as engineered bacterial cells, may be grown as a cell suspension in liquid nutrient broth, also referred to as liquid "culture medium."

In some embodiments, unconverted starch is used as a substrate feed for growing cells.

Examples of commonly used bacterial *Escherichia coli* growth media include, without limitation, LB (Luria Bertani) Miller broth (1% NaCl): 1% peptone, 0.5% yeast extract, and 1% NaCl; LB (Luria Bertani) Lennox Broth (0.5% NaCl): 1% peptone, 0.5% yeast extract, and 0.5% NaCl; SOB medium (Super Optimal Broth): 2% peptone, 0.5% Yeast extract, 10 mM NaCl, 2.5 mM KCl, 10 mM MgC12, 10 mM MgSO4; SOC medium (Super Optimal broth with Catabolic repressor): SOB+20 mM glucose; 2× YT broth (2× Yeast extract and Tryptone): 1.6% peptone, 1% yeast extract, and 0.5% NaCl; TB (Terrific Broth) medium: 1.2% peptone, 2.4% yeast extract, 72 mM K2HPO4, 17 mM KH2PO4 and 0.4% glycerol; and SB (Super Broth) medium: 3.2% peptone, 2% yeast extract, and 0.5% NaCl and or Korz medium (Korz, D J et al. 1995).

Examples of high density bacterial *Escherichia coli* growth media include, but are not limited to, DNAGro™ medium, ProGro™ medium, AutoX™ medium, DetoX™ medium, InduX™ medium, and SecPro™ medium.

In some embodiments, engineered cells are cultured under conditions that result in expression of enzymes or nucleic acids. Such culture conditions may depend on the particular product being expressed and the desired amount of the product.

In some embodiments, engineered cells are cultured at a temperature of 30° C. to 40° C. For example, engineered cells may be cultured at a temperature of 30° C., 31° C., 32° C., 33° C., 34° C., 35° C., 36° C., 37° C., 38° C., 39° C. or 40° C. Typically, engineered cells, such as engineered bacterial cells, are cultured at a temperature of 37° C.

In some embodiments, engineered cells are cultured for a period of time of 12 hours to 72 hours, or more. For example, engineered cells may be cultured for a period of time of 12, 18, 24, 30, 36, 42, 48, 54, 60, 66, or 72 hours. Typically, engineered cells, such as engineered bacterial cells, are cultured for a period of time of 12 to 24 hours. In some embodiments, engineered cells are cultured for 12 to 24 hours at a temperature of 37° C.

In some embodiments, engineered cells are cultured (e.g., in liquid cell culture medium) to an optical density, measured at a wavelength of 600 nm (OD600), of 5 to 25. In some embodiments, engineered cells are cultured to an OD600 of 5, 10, 15, 20, or 25.

In some embodiments, engineered cells are cultured to a density of $1\times10^4$ to $1\times10^8$ viable cells/ml cell culture medium. In some embodiments, engineered cells are cultured to a density of $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $1\times10^9$, or $1\times10^{10}$ viable cells/ml. In some embodiments, engineered cells are cultured to a density of $1\times10^8$ to $1\times10^{10}$ viable cells/ml. In some embodiments, engineered cells are cultured to a density of $2\times10^5$ to $3\times10^7$ viable cells/ml.

In some embodiments, engineered cells are cultured in a bioreactor. A bioreactor refers simply to a container in which cells are cultured, such as a culture flask, a dish, or a bag that may be single-use (disposable), autoclavable, or sterilizable. The bioreactor may be made of glass, or it may be polymer-based, or it may be made of other materials.

Examples of bioreactors include, without limitation, stirred tank (e.g., well mixed) bioreactors and tubular (e.g., plug flow) bioreactors, airlift bioreactors, membrane stirred tanks, spin filter stirred tanks, vibromixers, fluidized bed reactors, and membrane bioreactors. The mode of operating the bioreactor may be a batch or continuous processes and will depend on the engineered cells being cultured. A bioreactor is continuous when the feed and product streams are continuously being fed and withdrawn from the system. A batch bioreactor may have a continuous recirculating flow, but no continuous feeding of nutrient or product harvest. For intermittent-harvest and fed-batch (or batch fed) cultures, cells are inoculated at a lower viable cell density in a medium that is similar in composition to a batch medium. Cells are allowed to grow exponentially with essentially no external manipulation until nutrients are somewhat depleted and cells are approaching stationary growth phase. At this point, for an intermittent harvest batch-fed process, a portion of the cells and product may be harvested, and the removed culture medium is replenished with fresh medium. This process may be repeated several times. For production of recombinant proteins and antibodies, a fed-batch process may be used. While cells are growing exponentially, but nutrients are becoming depleted, concentrated feed medium (e.g., 10-15 times concentrated basal medium) is added either continuously or intermittently to supply additional nutrients, allowing for further increase in cell concentration and the length of the conversion phase. Fresh medium may be added proportionally to cell concentration without removal of culture medium (broth). To accommodate the addition of medium, a fed-batch culture is started in a volume much lower that the full capacity of the bioreactor (e.g., approximately 40% to 50% of the maximum volume).

Some methods of the present disclosure are directed to large-scale production of sugar. For large-scale production methods, engineered cells may be grown in liquid culture medium in a volume of 5 liters (L) to 50 L, or more. In some embodiments, engineered cells may be grown in liquid culture medium in a volume of greater than (or equal to) 10 L. In some embodiments, engineered cells are grown in liquid culture medium in a volume of 5 L, 10 L, 15 L, 20 L, 25 L, 30 L, 35 L, 40 L, 45 L, 50 L, or more. In some embodiments, engineered cells may be grown in liquid culture medium in a volume of 5 L to 10 L, 5 L to 15 L, 5 L to 20 L, 5 L to 25 L, 5 L to 30 L, 5 L to 35 L, 5 L to 40 L, 5 L to 45 L, 10 L to 15 L, 10 L to 20 L, 10 L to 25 L, 20 L to 30 L, 10 L to 35 L, 10 L to 40 L, 10 L to 45 L, 10 L to 50 L, 15 L to 20 L, 15 L to 25 L, 15 L to 30 L, 15 L to 35 L, 15 L to 40 L, 15 L to 45 L, or 15 to 50 L.

Typically, culturing of engineered cells is followed by lysing the cells. "Lysing" refers to the process by which cells are broken down, for example, by viral, enzymatic, mechanical, chemical, heat or osmotic mechanisms. A "cell lysate" refers to a fluid containing the contents of lysed cells (e.g., lysed engineered cells), including, for example, organelles, membrane lipids, proteins, nucleic acids and inverted membrane vesicles. Cell lysates of the present disclosure may be produced by lysing any population of engineered cells, as provided herein. A "cell lysate" may exclude permeabilized/perforated cells.

Methods of cell lysis, referred to as "lysing," are known in the art, any of which may be used in accordance with the present disclosure. Such cell lysis methods include, without limitation, physical/mechanical lysis, such as homogenization, as well as chemical, thermal, and/or enzymatic lysis.

Cell lysis can disturb carefully controlled cellular environments, resulting in protein degradation and modification by unregulated endogenous proteases and phosphatases. Thus, in some embodiments, protease inhibitors and/or phosphatase inhibitors may be added to the cell lysate or cells before lysis, or these activities may be removed by gene inactivation or protease targeting.

Cell lysates, in some embodiments, may be combined with at least one nutrient. For example, cell lysates may be combined with $Na_2HPO_4$, $KH_2PO_4$, $NH_4Cl$, NaCl, $MgSO_4$, $CaCl_2$. Examples of other nutrients include, without limitation, magnesium sulfate, magnesium chloride, magnesium orotate, magnesium citrate, potassium phosphate monobasic, potassium phosphate dibasic, potassium phosphate tribasic, sodium phosphate monobasic, sodium phosphate dibasic, sodium phosphate tribasic, ammonium phosphate monobasic, ammonium phosphate dibasic, ammonium sulfate, ammonium chloride, ammonium hydroxide, In some embodiments, cell lysates may consist of disrupted cell suspensions that are further modified by chemical, thermal, enzymatic or mechanical means to enrich or purify or reduce or eliminate specific components. For example, following disruption via mechanical, thermal, chemical or enzymatic means, as described above, the resulting material may be subjected to mechanical separation, e.g. membrane filtration, centrifugation or others, to partially enrich for a select enzymatic activity or to eliminate an undesired enzymatic activity or lysate component. Further examples may include the addition of salts or solvents to a disrupted cell suspension or alteration of the pH or temperature of the disrupted cell suspension resulting in the precipitation of desired activities followed by mechanical separation of these precipitated components as described above. Conversely, the addition of salts or solvents or the alteration of pH or temperature can be leveraged to eliminate undesired activities through either inactivation of those enzymes or precipitation and subsequent mechanical separation of the undesired enzymatic activity or activities.

Cell lysates, in some embodiments, may be combined with at least one cofactor. For example, cell lysates may be combined with adenosine diphosphate (ADP), adenosine triphosphate (ATP), nicotinamide adenine dinucleotide (NAD+), or other non-protein chemical compounds required for activity of an enzyme (e.g., inorganic ions and coenzymes).

In some embodiments, cell lysates are incubated under conditions that result in conversion of starch or cellulose/cellodextrin to sugar.

The volume of cell lysate used for a single reaction may vary. In some embodiments, the volume of a cell lysate is 1 to 150 $m^3$. For example, the volume of a cell lysate may be 1 $m^3$, 5 $m^3$, 10 $m^3$, 15 $m^3$, 20 $m^3$, 25 $m^3$, 30 $m^3$, 35 $m^3$, 40 $m^3$, 45 $m^3$, 50 $m^3$, 55 $m^3$, 60 $m^3$, 65 $m^3$, 70 $m^3$, 75 $m^3$, 80 $m^3$, 85 $m^3$, 90 $m^3$, 95 $m^3$, 100 $m^3$, 105 $m^3$, 110 $m^3$, 115 $m^3$, 120 $m^3$, 125 $m^3$, 130 $m^3$, 135 $m^3$, 140 $m^3$, 145 $m^3$, or 150 $m^3$. In some embodiments, the volume of a cell lysate is 25 $m^3$ to 150 $m^3$, 50 $m^3$ to 150 $m^3$, or 100 $m^3$ to 150 $m^3$.

Purified Enzymes

In some embodiments of the present invention enzymes may be purified prior to addition to the production reaction. Enzyme purification should be understood to mean any enrichment or extraction of a specific enzyme or enzymatic activity or groups of enzymes or enzymatic activities from a complex mixture of materials, examples including, but not limited to, disrupted cell suspensions or cultured growth media. Thus a purified enzyme or protein should be understood to be an enzyme or protein that has been separated or enriched from a complex matrix, wherein its relative concentration, as compared to other matrix components, is increased. Methods for purifying an enzyme include, but are not limited to, mechanical, chromatographic, chemical, pH or temperature means. For example, the addition of a salt to a disrupted cell suspension resulting in the precipitation of the target enzyme or protein followed by mechanical separation of the precipitated enzyme or protein, e.g., membrane filtration or centrifugation. Further examples may include the separation of an enzyme from a complex matrix through affinity based chromatographic methods (e.g. hexa-histidine-tag or streptavidin based purification).

Enzymatic Specificity

Enzymatic specificity should be understood to be a trait inherent to an enzyme wherein it demonstrates improved reaction enzyme kinetics, thermodynamics or rates for one substrate as compared to another substrate. Enzymes with high specificity are best exemplified by having a high ratio of catalytic rate (defined as turnover number or Kcat) to the Michaelis constant (Km) or Kcat/Km. It is advantageous to have an enzyme with high substrate specificity as this improves the rate of a reaction and improves yield by decreasing the production of non-target products. For example, the pathway described herein for the production of allulose has several intermediates that are similar in chemical structure, namely glucose 1-phosphate, glucose 6-phosphate, fructose 6-phosphate and allulose 6-phosphate. The ultimate enzymatic step in this process is the dephosphorylation of allulose 6-phosphate to the product allulose via an allulose 6-phosphate phosphatase. It is advantageous to utilize an enzyme with a very high-specificity for allulose 6-phosphate and a relatively low specificity for the other pathway intermediates, namely glucose 1-phosphate glucose 6-phosphate and fructose 6-phosphate. Catalytic dephosphorylation of these intermediates would result in the production of either glucose or fructose thus decreasing yield and increasing product complexity.

Additional Embodiments

1. A cell-free method for producing allulose, the method comprising:
   (a) culturing cells engineered to express a thermostable α-glucan phosphorylase (also referred to as a starch phosphorylase), a thermostable phosphoglucomutase, a thermostable phosphoglucoisomerase, a thermostable allulose 6-phosphate epimerase, and a thermostable allulose 6-phosphate phosphatase to produce cultured cells that express the thermostable enzymes;
   (b) lysing the cultured cells to produce a cell lysate;
   (c) heating the cell lysate to a temperature that inactivates native enzymatic activity but does not inactivate the thermostable enzymes of step (a) to produce a heat-inactivated lysate; and
   (d) incubating the heat-inactivated lysate in the presence of a starch and inorganic phosphate to produce allulose.

2. A cell-free method for producing allulose, the method comprising:
   (a) culturing at least two cell populations, wherein cells of each population are engineered to express at least one enzyme selected from the group consisting of thermostable α-glucan phosphorylases, thermostable phosphoglucomutases, thermostable phosphoglucoisomerases, thermostable allulose 6-phosphate epimerases, and thermostable allulose 6-phosphate phosphatases to produce at least two cultured populations of cells expressing different enzymes;
   (b) lysing cells of the at least two cultured populations to produce at least two cell lysates;
   (c) combining the at least two cell lysates to produce a cell lysate mixture that comprises a thermostable α-glucan phosphorylase, a thermostable phosphoglucomutase, a thermostable phosphoglucoisomerase, a thermostable allulose 6-phosphate epimerase, and a thermostable allulose 6-phosphate phosphatase;
   (d) heating the cell lysate mixture to a temperature that inactivates native enzymatic activity but does not inactivate the thermostable enzymes of step (c) to produce a heat-inactivated lysate; and
   (e) incubating the reaction mixture in the presence of a starch and inorganic phosphate to produce allulose.

3. A cell-free method for producing allulose, the method comprising:
   (a) culturing at least two cell populations, wherein cells of each population are engineered to express at least one enzyme selected from the group consisting of thermostable α-glucan phosphorylases, thermostable phosphoglucomutases, thermostable phosphoglucoisomerases, thermostable allulose 6-phosphate epimerases, and thermostable allulose 6-phosphate phosphatases to produce at least two cultured populations of cells expressing different enzymes;
   (b) lysing cells of the at least two cultured populations to produce at least two cell lysates;
   (c) combining the at least two cell lysates to produce a cell lysate mixture;
   (d) heating the cell lysate mixture to a temperature that inactivates native enzymatic activity but does not inactivate the thermostable enzymes of step (a) to produce a heat-inactivated lysate;
   (e) adding to the heat-inactivated lysate at least one purified enzyme selected from the group consisting of thermostable α-glucan phosphorylases, thermostable phosphoglucomutases, thermostable phosphoglucoisomerases, thermostable allulose 6-phosphate epimerases, and thermostable allulose 6-phosphate phosphatases to produce a reaction mixture comprising a α-glucan phosphorylase, a phosphoglucomutase, a phosphoglucoisomerase, an allulose 6-phosphate epimerase, and an allulose 6-phosphate phosphatase; and
   (f) incubating the reaction mixture in the presence of a starch and inorganic phosphate to produce allulose.

4. The cell-free method of any one of embodiments 1-3, wherein the thermostable α-glucan phosphorylase(s) is selected from the group consisting of *Aquifex aeolicus, Thermocrinis minervae, Thermosulfidibacter takaii, Thermosulfurimonas dismutans, Thermococcus litoralis, Palaeococcus pacificus, Thermotoga neapolitana, Ruminiclostridium thermocellum, Pyrococcus abyssi, Thermococcus thioreducens, Deinococcus radiodurans, Sulfolobus acidocaldarius, Thermus caldophilus, Meiothermus silvanus, Oceanithermus profundus, Ardenticatena maritima, Thermococcus barophilus, Pseudothermotoga thermarum, Hydrogenobacter thermophilus, Thermus oshimai, Meiothermus ruber*, and *Marinitoga piezophila* α-glucan phosphorylases.

5. The cell-free method of any one of embodiments 1-4, wherein the thermostable phosphoglucomutase(s) is selected from the group consisting of *Thermococcus kodakaraensis, Pyrococcus kukulkanii, Ammonifex degensii, Methanothermobacter wolfeii, Methanothermus fervidus, Sulfolobus acidocaldarius, Archaeoglobus fulgidus, Ferroglobus placidus, Geoglobus ahangari, Archaeoglobus veneficus, Archaeoglobus sulfaticallidus, Aciduliprofundum boonie, Clostridium*

*thermocellum, Defluviitalea phaphyphila, Caminicella sporogenes, Caloranaerobacter ferrireducens, Thermosipho malanesiensis, Fervidobacterium pennivorans, Symbiobacterium thermophilum, Spirochaeta thermophila,* and *Thermoanaerobacter wiegelii* phosphoglucomutases.

6. The cell-free method of any one of embodiments 1-5, wherein the thermostable phosphoglucomutase(s) is selected from the group consisting of *Therms thermophilus, Meiothermus timidus, Thermus filiformis, Marinithermus hydrothermalis, Thermosipho africanus, Sulfurihydrogenibium azorense, Persephonella marina, Marinitoga piezophila, Kosmotoga olearia, Thermotoga maritima, Geobacillus stearothermophilus, Anoxybacillus flavithermus, Thermosulfidibacter takaii, Fervidobacterium nodosum, Clostridium thermocellum, Thermoanaerobacterium thermosaccharolyticum, Methanococcus jannaschii, Methanotorris igneus, Methanocaldococcus villosus, Methanothermococcus okinawensis, Pseudothermotoga thermarum, Deferribacter desulfuricans,* and *Thermovibrio ammonificans,* phosphoglucomutases.

7. The cell-free method of any one of embodiments 1-6, wherein the thermostable allulose 6-phosphate epimerase(s) is selected from the group consisting of *Thermobacterium thermosaccharolyticum, Thermoanaerobacter brockii, Caldanaerobacter subterraneus, Deferribacter desulfuricans, Thermocrinis ruber, Hydrogenivirga* sp. 128-5-R1-1, *Brevibacillus thermoruber, Thermosipho atlanticus,* and *Thermosulfidibacter takaii* allulose 6-phosphate epimerases.

8. The cell-free method of any one of embodiments 1-7, wherein the thermostable allulose 6-phosphate phosphatase(s) is selected from the group consisting of *Thermoanaerobacter wiegelii, Thermoanaerobacter ethanolicus, Thermus islandicus, Deinococcus geothermalis* DSM 11300, *Thermosphaera aggregans, Crenarchaeota archaeon, Pyrococcus horikoshii* Ot3, *Aquifex aeolicus, Ruminiclostridium thermocellum, Desulfotomaculum kuznetsovii, Caldanaerobacter subterraneus, Acidothermus cellulolyticus, Methanothermobacter thermautotrophicus, Thermobifida fusca, Thermotoga neapolitana, Petrotoga mobilis,* and *Thermodesulfatator indicus,* and *Thermus thermophilus* allulose 6-phosphate phosphatases.

9. A cell-free method for producing glucose, the method comprising:
(a) culturing cells engineered to express a thermostable α-glucan phosphorylase, a thermostable phosphoglucomutase, and a thermostable glucose 6-phosphate phosphatase to produce cultured cells that express the thermostable enzymes;
(b) lysing the cultured cells to produce a cell lysate;
(c) heating the cell lysate to a temperature that inactivates native enzymatic activity but does not inactivate the thermostable enzymes of step (a) to produce a heat-inactivated lysate; and
(d) incubating the heat-inactivated lysate in the presence of a starch and inorganic phosphate to produce glucose.

10. A cell-free method for producing glucose, the method comprising:
(a) culturing at least two cell populations, wherein cells of each population are engineered to express at least one enzyme selected from the group consisting of thermostable α-glucan phosphorylases, thermostable phosphoglucomutases, and thermostable glucose 6-phosphate phosphatases to produce at least two cultured populations of cells expressing different enzymes;
(b) lysing cells of the at least two cultured populations to produce at least two cell lysates;

(c) combining the at least two cell lysates to produce a cell lysate mixture that comprises a thermostable α-glucan phosphorylase, a thermostable phosphoglucomutase, and a thermostable glucose 6-phosphate phosphatase;
(d) heating the cell lysate mixture to a temperature that inactivates native enzymatic activity but does not inactivate the thermostable enzymes of step (c) to produce a heat-inactivated lysate; and
(e) incubating the reaction mixture in the presence of a starch and inorganic phosphate to produce glucose.

11. A cell-free method for producing glucose, the method comprising:
(a) culturing at least two cell populations, wherein cells of each population are engineered to express at least one enzyme selected from the group consisting of thermostable α-glucan phosphorylases, thermostable phosphoglucomutases, and thermostable glucose 6-phosphate phosphatases to produce at least two cultured populations of cells expressing different enzymes;
(b) lysing cells of the at least two cultured populations to produce at least two cell lysates;
(c) combining the at least two cell lysates to produce a cell lysate mixture;
(d) heating the cell lysate mixture to a temperature that inactivates native enzymatic activity but does not inactivate the thermostable enzymes of step (a) to produce a heat-inactivated lysate;
(e) adding to the heat-inactivated lysate at least one purified enzyme selected from the group consisting of thermostable α-glucan phosphorylases, thermostable phosphoglucomutases, and thermostable glucose 6-phosphate phosphatases to produce a reaction mixture comprising a α-glucan phosphorylase, a phosphoglucomutase, and a glucose 6-phosphate phosphatase; and
(f) incubating the reaction mixture in the presence of a starch and inorganic phosphate to produce glucose.

12. A cell-free method for producing fructose, the method comprising:
(a) culturing cells engineered to express a thermostable α-glucan phosphorylase, a thermostable phosphoglucomutase, a thermostable phosphoglucoisomerase, and a thermostable fructose 6-phosphate phosphatase to produce cultured cells that express the thermostable enzymes;
(b) lysing the cultured cells to produce a cell lysate;
(c) heating the cell lysate to a temperature that inactivates native enzymatic activity but does not inactivate the thermostable enzymes of step (a) to produce a heat-inactivated lysate; and
(d) incubating the heat-inactivated lysate in the presence of a starch and inorganic phosphate to produce fructose.

13. A cell-free method for producing fructose, the method comprising:
(a) culturing at least two cell populations, wherein cells of each population are engineered to express at least one enzyme selected from the group consisting of thermostable α-glucan phosphorylases, thermostable phosphoglucomutases, thermostable phosphoglucoisomerases, and thermostable fructose 6-phosphate phosphatases to produce at least two cultured populations of cells expressing different enzymes;
(b) lysing cells of the at least two cultured populations to produce at least two cell lysates;
(c) combining the at least two cell lysates to produce a cell lysate mixture that comprises a thermostable α-glucan phosphorylase, a thermostable phosphoglucomutase, a thermostable phosphoglucoisomerase, and a thermostable fructose 6-phosphate phosphatase;

(d) heating the cell lysate mixture to a temperature that inactivates native enzymatic activity but does not inactivate the thermostable enzymes of step (c) to produce a heat-inactivated lysate; and (e) incubating the reaction mixture in the presence of a starch and inorganic phosphate to produce fructose.

14. A cell-free method for producing fructose, the method comprising:

(a) culturing at least two cell populations, wherein cells of each population are engineered to express at least one enzyme selected from the group consisting of thermostable α-glucan phosphorylases, thermostable phosphoglucomutases, thermostable phosphoglucoisomerases, and thermostable fructose 6-phosphate phosphatases to produce at least two cultured populations of cells expressing different enzymes;

(b) lysing cells of the at least two cultured populations to produce at least two cell lysates;

(c) combining the at least two cell lysates to produce a cell lysate mixture;

(d) heating the cell lysate mixture to a temperature that inactivates native enzymatic activity but does not inactivate the thermostable enzymes of step (a) to produce a heat-inactivated lysate;

(e) adding to the heat-inactivated lysate at least one purified enzyme selected from the group consisting of thermostable α-glucan phosphorylases, thermostable phosphoglucomutases, thermostable phosphoglucoisomerases, and thermostable fructose 6-phosphate phosphatases to produce a reaction mixture comprising a α-glucan phosphorylase, a phosphoglucomutase, a phosphoglucoisomerase, and a fructose 6-phosphate phosphatase; and (f) incubating the reaction mixture in the presence of a starch and inorganic phosphate to produce fructose.

15. A cell-free method for producing sorbitol, the method comprising:

(a) culturing cells engineered to express a thermostable α-glucan phosphorylase, a thermostable phosphoglucomutase, a thermostable aldose dehydrogenase, and a thermostable sorbitol-6-phosphate phosphatase to produce cultured cells that express the thermostable enzymes;

(b) lysing the cultured cells to produce a cell lysate;

(c) heating the cell lysate to a temperature that inactivates native enzymatic activity but does not inactivate the thermostable enzymes of step (a) to produce a heat-inactivated lysate; and (d) incubating the heat-inactivated lysate in the presence of a starch and inorganic phosphate to produce sorbitol.

16. A cell-free method for producing sorbitol, the method comprising:

(a) culturing at least two cell populations, wherein cells of each population are engineered to express at least one enzyme selected from the group consisting of thermostable α-glucan phosphorylases, thermostable phosphoglucomutases, thermostable aldose dehydrogenases, and thermostable sorbitol-6-phosphate phosphatases to produce at least two cultured populations of cells expressing different enzymes;

(b) lysing cells of the at least two cultured populations to produce at least two cell lysates;

(c) combining the at least two cell lysates to produce a cell lysate mixture that comprises a thermostable α-glucan phosphorylase, a thermostable phosphoglucomutase, a thermostable aldose dehydrogenase, and a thermostable sorbitol-6-phosphate phosphatase;

(d) heating the cell lysate mixture to a temperature that inactivates native enzymatic activity but does not inactivate the thermostable enzymes of step (c) to produce a heat-inactivated lysate; and (e) incubating the reaction mixture in the presence of a starch and inorganic phosphate to produce sorbitol.

17. A cell-free method for producing sorbitol, the method comprising:

(a) culturing at least two cell populations, wherein cells of each population are engineered to express at least one enzyme selected from the group consisting of thermostable α-glucan phosphorylases, thermostable phosphoglucomutases, thermostable aldose dehydrogenases, and thermostable sorbitol-6-phosphate phosphatases to produce at least two cultured populations of cells expressing different enzymes;

(b) lysing cells of the at least two cultured populations to produce at least two cell lysates;

(c) combining the at least two cell lysates to produce a cell lysate mixture;

(d) heating the cell lysate mixture to a temperature that inactivates native enzymatic activity but does not inactivate the thermostable enzymes of step (a) to produce a heat-inactivated lysate;

(e) adding to the heat-inactivated lysate at least one purified enzyme selected from the group consisting of thermostable α-glucan phosphorylases, thermostable phosphoglucomutases, thermostable aldose dehydrogenases, and thermostable sorbitol-6-phosphate phosphatases to produce a reaction mixture comprising a α-glucan phosphorylase, a phosphoglucomutase, an aldose dehydrogenase, and a sorbitol-6-phosphate phosphatase; and (f) incubating the reaction mixture in the presence of a starch and inorganic phosphate to produce sorbitol.

18. A cell-free method for producing ribulose, the method comprising:

(a) culturing cells engineered to express a thermostable α-glucan phosphorylase, a thermostable phosphoglucomutase, a thermostable glucose 6-phosphate dehydrogenase, a thermostable 6-phosphogluconolactonase, a thermostable 6-phosphogluconate dehydrogenase, and a thermostable ribulose 5-phosphate phosphatase to produce cultured cells that express the thermostable enzymes;

(b) lysing the cultured cells to produce a cell lysate;

(c) heating the cell lysate to a temperature that inactivates native enzymatic activity but does not inactivate the thermostable enzymes of step (a) to produce a heat-inactivated lysate; and (d) incubating the heat-inactivated lysate in the presence of a starch and inorganic phosphate to produce ribulose.

19. A cell-free method for producing ribulose, the method comprising:

(a) culturing at least two cell populations, wherein cells of each population are engineered to express at least one enzyme selected from the group consisting of thermostable α-glucan phosphorylases, thermostable phosphoglucomutases, thermostable glucose 6-phosphate dehydrogenases, thermostable 6-phosphogluconolactonases, thermostable 6-phosphogluconate dehydrogenases, and thermostable ribulose 5-phosphate phosphatases to produce at least two cultured populations of cells expressing different enzymes;

(b) lysing cells of the at least two cultured populations to produce at least two cell lysates;

(c) combining the at least two cell lysates to produce a cell lysate mixture that comprises a thermostable α-glucan phosphorylase, a thermostable phosphoglucomutase, a thermostable glucose 6-phosphate dehydrogenase, a thermostable 6-phosphogluconolactonase, a thermostable 6-phosphogluconate dehydrogenase, and a thermostable ribulose 5-phosphate phosphatase;

(d) heating the cell lysate mixture to a temperature that inactivates native enzymatic activity but does not inactivate the thermostable enzymes of step (c) to produce a heat-inactivated lysate; and (e) incubating the reaction mixture in the presence of a starch and inorganic phosphate to produce ribulose.

20. A cell-free method for producing ribulose, the method comprising:

(a) culturing at least two cell populations, wherein cells of each population are engineered to express at least one enzyme selected from the group consisting of thermostable α-glucan phosphorylases, thermostable phosphoglucomutases, thermostable glucose 6-phosphate dehydrogenases, thermostable 6-phosphogluconolactonases, thermostable 6-phosphogluconate dehydrogenases, and thermostable ribulose 5-phosphate phosphatases to produce at least two cultured populations of cells expressing different enzymes;

(b) lysing cells of the at least two cultured populations to produce at least two cell lysates;

(c) combining the at least two cell lysates to produce a cell lysate mixture;

(d) heating the cell lysate mixture to a temperature that inactivates native enzymatic activity but does not inactivate the thermostable enzymes of step (a) to produce a heat-inactivated lysate;

(e) adding to the heat-inactivated lysate at least one purified enzyme selected from the group consisting of thermostable α-glucan phosphorylases, thermostable phosphoglucomutases, thermostable glucose 6-phosphate dehydrogenases, thermostable 6-phosphogluconolactonases, thermostable 6-phosphogluconate dehydrogenases, and thermostable ribulose 5-phosphate phosphatases to produce a reaction mixture comprising a α-glucan phosphorylase, a phosphoglucomutase, a glucose 6-phosphate dehydrogenase, a 6-phosphogluconolactonase, a 6-phosphogluconate dehydrogenase, and a ribulose 5-phosphate phosphatase; and (f) incubating the reaction mixture in the presence of a starch and inorganic phosphate to produce ribulose.

21. A cell-free method for producing ribose, the method comprising:

(a) culturing cells engineered to express a thermostable α-glucan phosphorylase, a thermostable phosphoglucomutase, a thermostable glucose 6-phosphate dehydrogenase, a thermostable 6-phosphogluconolactonase, a thermostable 6-phosphogluconate dehydrogenase, a thermostable ribose 5-phosphate isomerase, and a thermostable ribose 5-phosphate phosphatase to produce cultured cells that express the thermostable enzymes;

(b) lysing the cultured cells to produce a cell lysate;

(c) heating the cell lysate to a temperature that inactivates native enzymatic activity but does not inactivate the thermostable enzymes of step (a) to produce a heat-inactivated lysate; and (d) incubating the heat-inactivated lysate in the presence of a starch and inorganic phosphate to produce ribose.

22. A cell-free method for producing ribose, the method comprising:

(a) culturing at least two cell populations, wherein cells of each population are engineered to express at least one enzyme selected from the group consisting of thermostable α-glucan phosphorylases, thermostable phosphoglucomutases, thermostable glucose 6-phosphate dehydrogenases, thermostable 6-phosphogluconolactonases, thermostable 6-phosphogluconate dehydrogenases, thermostable ribose 5-phosphate isomerases, and thermostable ribose 5-phosphate phosphatases to produce at least two cultured populations of cells expressing different enzymes;

(b) lysing cells of the at least two cultured populations to produce at least two cell lysates;

(c) combining the at least two cell lysates to produce a cell lysate mixture that comprises a thermostable α-glucan phosphorylase, a thermostable phosphoglucomutase, a thermostable glucose 6-phosphate dehydrogenase, a thermostable 6-phosphogluconolactonase, a thermostable 6-phosphogluconate dehydrogenase, a thermostable ribose 5-phosphate isomerase, and a thermostable ribose 5-phosphate phosphatase;

(d) heating the cell lysate mixture to a temperature that inactivates native enzymatic activity but does not inactivate the thermostable enzymes of step (c) to produce a heat-inactivated lysate; and (e) incubating the reaction mixture in the presence of a starch and inorganic phosphate to produce ribose.

23. A cell-free method for producing ribose, the method comprising:

(a) culturing at least two cell populations, wherein cells of each population are engineered to express at least one enzyme selected from the group consisting of thermostable α-glucan phosphorylases, thermostable phosphoglucomutases, thermostable glucose 6-phosphate dehydrogenases, thermostable 6-phosphogluconolactonases, thermostable 6-phosphogluconate dehydrogenases, thermostable ribose 5-phosphate isomerases, and thermostable ribose 5-phosphate phosphatases to produce at least two cultured populations of cells expressing different enzymes;

(b) lysing cells of the at least two cultured populations to produce at least two cell lysates;

(c) combining the at least two cell lysates to produce a cell lysate mixture;

(d) heating the cell lysate mixture to a temperature that inactivates native enzymatic activity but does not inactivate the thermostable enzymes of step (a) to produce a heat-inactivated lysate;

(e) adding to the heat-inactivated lysate at least one purified enzyme selected from the group consisting of thermostable α-glucan phosphorylases, thermostable phosphoglucomutases, thermostable glucose 6-phosphate dehydrogenases, thermostable 6-phosphogluconolactonases, thermostable 6-phosphogluconate dehydrogenases, thermostable ribose 5-phosphate isomerases, and thermostable ribose 5-phosphate phosphatases to produce a reaction mixture comprising a α-glucan phosphorylase, a phosphoglucomutase, a glucose 6-phosphate dehydrogenase, a 6-phosphogluconolactonase, a 6-phosphogluconate dehydrogenase, a ribose 5-phosphate isomerase, and a ribose 5-phosphate phosphatase; and (f) incubating the reaction mixture in the presence of a starch and inorganic phosphate to produce ribose.

24. A cell-free method for producing arabinose, the method comprising:
(a) culturing cells engineered to express a thermostable α-glucan phosphorylase, a thermostable phosphoglucomutase, a thermostable glucose 6-phosphate dehydrogenase, a thermostable 6-phosphogluconolactonase, a thermostable 6-phosphogluconate dehydrogenase, a thermostable arabinose 5-phosphate isomerase, and a thermostable arabinose 5-phosphate phosphatase to produce cultured cells that express the thermostable enzymes;
(b) lysing the cultured cells to produce a cell lysate;
(c) heating the cell lysate to a temperature that inactivates native enzymatic activity but does not inactivate the thermostable enzymes of step (a) to produce a heat-inactivated lysate; and
(d) incubating the heat-inactivated lysate in the presence of a starch and inorganic phosphate to produce arabinose.

25. A cell-free method for producing arabinose, the method comprising:
(a) culturing at least two cell populations, wherein cells of each population are engineered to express at least one enzyme selected from the group consisting of thermostable α-glucan phosphorylases, thermostable phosphoglucomutases, thermostable glucose 6-phosphate dehydrogenases, thermostable 6-phosphogluconolactonases, thermostable 6-phosphogluconate dehydrogenases, thermostable arabinose 5-phosphate isomerases, and thermostable arabinose 5-phosphate phosphatases to produce at least two cultured populations of cells expressing different enzymes;
(b) lysing cells of the at least two cultured populations to produce at least two cell lysates;
(c) combining the at least two cell lysates to produce a cell lysate mixture that comprises a thermostable α-glucan phosphorylase, a thermostable phosphoglucomutase, a thermostable glucose 6-phosphate dehydrogenase, a thermostable 6-phosphogluconolactonase, a thermostable 6-phosphogluconate dehydrogenase, a thermostable arabinose 5-phosphate isomerase, and a thermostable arabinose 5-phosphate phosphatase;
(d) heating the cell lysate mixture to a temperature that inactivates native enzymatic activity but does not inactivate the thermostable enzymes of step (c) to produce a heat-inactivated lysate; and
(e) incubating the reaction mixture in the presence of a starch and inorganic phosphate to produce arabinose.

26. A cell-free method for producing arabinose, the method comprising:
(a) culturing at least two cell populations, wherein cells of each population are engineered to express at least one enzyme selected from the group consisting of thermostable α-glucan phosphorylases, thermostable phosphoglucomutases, thermostable glucose 6-phosphate dehydrogenases, thermostable 6-phosphogluconolactonases, thermostable 6-phosphogluconate dehydrogenases, thermostable arabinose 5-phosphate isomerases, and thermostable arabinose 5-phosphate phosphatases to produce at least two cultured populations of cells expressing different enzymes;
(b) lysing cells of the at least two cultured populations to produce at least two cell lysates;
(c) combining the at least two cell lysates to produce a cell lysate mixture;
(d) heating the cell lysate mixture to a temperature that inactivates native enzymatic activity but does not inactivate the thermostable enzymes of step (a) to produce a heat-inactivated lysate;
(e) adding to the heat-inactivated lysate at least one purified enzyme selected from the group consisting of thermostable α-glucan phosphorylases, thermostable phosphoglucomutases, thermostable glucose 6-phosphate dehydrogenases, thermostable 6-phosphogluconolactonases, thermostable 6-phosphogluconate dehydrogenases, thermostable arabinose 5-phosphate isomerases, and thermostable arabinose 5-phosphate phosphatases to produce a reaction mixture comprising a α-glucan phosphorylase, a phosphoglucomutase, a glucose 6-phosphate dehydrogenase, a 6-phosphogluconolactonase, a 6-phosphogluconate dehydrogenase, an arabinose 5-phosphate isomerase, and an arabinose 5-phosphate phosphatase; and
(f) incubating the reaction mixture in the presence of a starch and inorganic phosphate to produce arabinose.

27. A cell-free method for producing mannose, the method comprising:
(a) culturing cells engineered to express a thermostable α-glucan phosphorylase, a thermostable phosphoglucomutase, a thermostable phosphoglucoisomerase, a thermostable mannose 6-phosphate epimerase, and a thermostable mannose 6-phosphate phosphatase to produce cultured cells that express the thermostable enzymes;
(b) lysing the cultured cells to produce a cell lysate;
(c) heating the cell lysate to a temperature that inactivates native enzymatic activity but does not inactivate the thermostable enzymes of step (a) to produce a heat-inactivated lysate; and
(d) incubating the heat-inactivated lysate in the presence of a starch and inorganic phosphate to produce mannose.

28. A cell-free method for producing mannose, the method comprising:
(a) culturing at least two cell populations, wherein cells of each population are engineered to express at least one enzyme selected from the group consisting of thermostable α-glucan phosphorylases, thermostable phosphoglucomutases, thermostable phosphoglucoisomerases, thermostable mannose 6-phosphate epimerases, and thermostable mannose 6-phosphate phosphatases to produce at least two cultured populations of cells expressing different enzymes;
(b) lysing cells of the at least two cultured populations to produce at least two cell lysates;
(c) combining the at least two cell lysates to produce a cell lysate mixture that comprises a thermostable α-glucan phosphorylase, a thermostable phosphoglucomutase, a thermostable phosphoglucoisomerase, a thermostable mannose 6-phosphate epimerase, and a thermostable mannose 6-phosphate phosphatase;
(d) heating the cell lysate mixture to a temperature that inactivates native enzymatic activity but does not inactivate the thermostable enzymes of step (c) to produce a heat-inactivated lysate; and
(e) incubating the reaction mixture in the presence of a starch and inorganic phosphate to produce mannose.

29. A cell-free method for producing mannose, the method comprising:
(a) culturing at least two cell populations, wherein cells of each population are engineered to express at least one enzyme selected from the group consisting of thermostable α-glucan phosphorylases, thermostable phosphoglucomutases, thermostable phosphoglucoisomerases, thermostable mannose 6-phosphate epimerases, and thermostable mannose 6-phosphate phosphatases to produce at least two cultured populations of cells expressing different enzymes;

(b) lysing cells of the at least two cultured populations to produce at least two cell lysates;

(c) combining the at least two cell lysates to produce a cell lysate mixture;

(d) heating the cell lysate mixture to a temperature that inactivates native enzymatic activity but does not inactivate the thermostable enzymes of step (a) to produce a heat-inactivated lysate;

(e) adding to the heat-inactivated lysate at least one purified enzyme selected from the group consisting of thermostable α-glucan phosphorylases, thermostable phosphoglucomutases, thermostable phosphoglucoisomerases, thermostable mannose 6-phosphate epimerases, and thermostable mannose 6-phosphate phosphatases to produce a reaction mixture comprising a α-glucan phosphorylase, a phosphoglucomutase, a phosphoglucoisomerase, an mannose 6-phosphate epimerase, and an mannose 6-phosphate phosphatase; and (f) incubating the reaction mixture in the presence of a starch and inorganic phosphate to produce mannose.

30. The method of any one of embodiments 1-26, wherein the cells comprise bacterial cells.

31. The method of any one of embodiments 1-26, wherein the cells comprise yeast cells.

32. The method for any one of embodiments 1-31, wherein at least one of the enzymes is heterologous to the cells.

33. The method of any one of embodiments 1-32, wherein lysing step (b) comprises mechanically, chemically, or enzymatically lysing the cultured cells.

34. The method for any one of embodiments 1-33, wherein heating step (c) comprises heating the cell lysate to a temperature of at least 50° C.

35. The method for any one of embodiments 1-34, wherein the starch comprises amylose, amylopectin, or both amylose and amylopectin.

36. The method for any one of embodiments 1-35, wherein the thermostable α-glucan phosphorylase and the thermostable phosphoglucomutase are expressed as a single fusion protein or a bifunctional protein.

37. A cell lysate produced by the method for any one of embodiments 1-36.

38. An engineered cell comprising a α-glucan phosphorylase, a phosphoglucomutase, and a glucose 6-phosphate phosphatase, optionally wherein at least one of the foregoing enzymes is a thermostable enzyme.

39. An engineered cell comprising a α-glucan phosphorylase, a phosphoglucomutase, a phosphoglucoisomerase, and a fructose 6-phosphate phosphatase, optionally wherein at least one of the foregoing enzymes is a thermostable enzyme.

40. An engineered cell comprising a α-glucan phosphorylase, a phosphoglucomutase, a phosphoglucoisomerase, an allulose 6-phosphate epimerase, and an allulose 6-phosphate phosphatase, optionally wherein at least one of the foregoing enzymes is a thermostable enzyme.

41. An engineered cell comprising a α-glucan phosphorylase, a phosphoglucomutase, a aldose dehydrogenase, and a sorbitol-6-phosphate phosphatase, optionally wherein at least one of the foregoing enzymes is a thermostable enzyme.

42. An engineered cell comprising a α-glucan phosphorylase, a phosphoglucomutase, a glucose 6-phosphate dehydrogenase, a 6-phosphogluconolactonase, a 6-phosphogluconate dehydrogenase, and a ribulose 5-phosphate phosphatase, optionally wherein at least one of the foregoing enzymes is a thermostable enzyme.

43. An engineered cell comprising a α-glucan phosphorylase, a phosphoglucomutase, a glucose 6-phosphate dehydrogenase, a 6-phosphogluconolactonase, a 6-phosphogluconate dehydrogenase, a ribose 5-phosphate isomerase, and a ribose 5-phosphate phosphatase, optionally wherein at least one of the foregoing enzymes is a thermostable enzyme.

44. An engineered cell comprising a α-glucan phosphorylase, a phosphoglucomutase, a glucose 6-phosphate dehydrogenase, a 6-phosphogluconolactonase, a 6-phosphogluconate dehydrogenase, an arabinose 5-phosphate isomerase, and an arabinose 5-phosphate phosphatase, optionally wherein at least one of the foregoing enzymes is a thermostable enzyme.

45. An engineered cell comprising a α-glucan phosphorylase, a phosphoglucomutase, a phosphoglucoisomerase, a mannose 6-phosphate epimerase, and a mannose 6-phosphate phosphatase, optionally wherein at least one of the foregoing enzymes is a thermostable enzyme.

46. The engineered cell of any one of embodiments embodiment 38-45, wherein the cell is a bacterial cell or a yeast cell.

47. A single cell lysate, a mixture of cell lysates obtained from at least two cell populations, or a reaction mixture comprising a α-glucan phosphorylase, a phosphoglucomutase, and a glucose 6-phosphate phosphatase, optionally wherein at least one of the foregoing enzymes is a thermostable enzyme.

48. A single cell lysate, a mixture of cell lysates obtained from at least two cell populations, or a reaction mixture comprising a α-glucan phosphorylase, a phosphoglucomutase, a phosphoglucoisomerase, and a fructose 6-phosphate phosphatase, optionally wherein at least one of the foregoing enzymes is a thermostable enzyme.

49. A single cell lysate, a mixture of cell lysates obtained from at least two cell populations, or a reaction mixture comprising a α-glucan phosphorylase, a phosphoglucomutase, a phosphoglucoisomerase, an allulose 6-phosphate epimerase, and an allulose 6-phosphate phosphatase, optionally wherein at least one of the foregoing enzymes is a thermostable enzyme.

50. A single cell lysate, a mixture of cell lysates obtained from at least two cell populations, or a reaction mixture comprising a α-glucan phosphorylase, a phosphoglucomutase, a aldose dehydrogenase, and a sorbitol-6-phosphate phosphatase, optionally wherein at least one of the foregoing enzymes is a thermostable enzyme.

51. A single cell lysate, a mixture of cell lysates obtained from at least two cell populations, or a reaction mixture comprising a α-glucan phosphorylase, a phosphoglucomutase, a glucose 6-phosphate dehydrogenase, a 6-phosphogluconolactonase, a 6-phosphogluconate dehydrogenase, and a ribulose 5-phosphate phosphatase, optionally wherein at least one of the foregoing enzymes is a thermostable enzyme.

52. A single cell lysate, a mixture of cell lysates obtained from at least two cell populations, or a reaction mixture comprising a α-glucan phosphorylase, a phosphoglucomutase, a glucose 6-phosphate dehydrogenase, a 6-phosphogluconolactonase, a 6-phosphogluconate dehydrogenase, a ribose 5-phosphate isomerase, and a ribose 5-phosphate phosphatase, optionally wherein at least one of the foregoing enzymes is a thermostable enzyme.

53. A single cell lysate, a mixture of cell lysates obtained from at least two cell populations, or a reaction mixture comprising a α-glucan phosphorylase, a phosphoglucomutase, a glucose 6-phosphate dehydrogenase, a 6-phosphogluconolactonase, a 6-phosphogluconate dehydrogenase, an arabinose 5-phosphate isomerase, and an arabinose 5-phosphate phosphatase, optionally wherein at least one of the foregoing enzymes is a thermostable enzyme.

54. A single cell lysate, a mixture of cell lysates obtained from at least two cell populations, or a reaction mixture comprising a α-glucan phosphorylase, a phosphoglucomutase, a phosphoglucoisomerase, an mannose 6-phosphate epimerase, and an mannose 6-phosphate phosphatase, optionally wherein at least one of the foregoing enzymes is a thermostable enzyme.

55. A cell-free method for producing allulose, the method comprising:
(a) culturing cells engineered to express a thermostable cellodextrin phosphorylase, a thermostable phosphoglucomutase, a thermostable phosphoglucoisomerase, a thermostable allulose 6-phosphate epimerase, and a thermostable allulose 6-phosphate phosphatase to produce cultured cells that express the thermostable enzymes;
(b) lysing the cultured cells to produce a cell lysate;
(c) heating the cell lysate to a temperature that inactivates native enzymatic activity but does not inactivate the thermostable enzymes of step (a) to produce a heat-inactivated lysate; and
(d) incubating the heat-inactivated lysate in the presence of a cellodextrin and inorganic phosphate to produce allulose.

56. A cell-free method for producing allulose, the method comprising:
(a) culturing at least two cell populations, wherein cells of each population are engineered to express at least one enzyme selected from the group consisting of thermostable cellodextrin phosphorylases, thermostable phosphoglucomutases, thermostable phosphoglucoisomerases, thermostable allulose 6-phosphate epimerases, and thermostable allulose 6-phosphate phosphatases to produce at least two cultured populations of cells expressing different enzymes;
(b) lysing cells of the at least two cultured populations to produce at least two cell lysates;
(c) combining the at least two cell lysates to produce a cell lysate mixture that comprises a thermostable cellodextrin phosphorylase, a thermostable phosphoglucomutase, a thermostable phosphoglucoisomerase, a thermostable allulose 6-phosphate epimerase, and a thermostable allulose 6-phosphate phosphatase;
(d) heating the cell lysate mixture to a temperature that inactivates native enzymatic activity but does not inactivate the thermostable enzymes of step (c) to produce a heat-inactivated lysate; and
(e) incubating the reaction mixture in the presence of a cellodextrin and inorganic phosphate to produce allulose.

57. A cell-free method for producing allulose, the method comprising:
(a) culturing at least two cell populations, wherein cells of each population are engineered to express at least one enzyme selected from the group consisting of thermostable cellodextrin phosphorylases, thermostable phosphoglucomutases, thermostable phosphoglucoisomerases, thermostable allulose 6-phosphate epimerases, and thermostable allulose 6-phosphate phosphatases to produce at least two cultured populations of cells expressing different enzymes;
(b) lysing cells of the at least two cultured populations to produce at least two cell lysates;
(c) combining the at least two cell lysates to produce a cell lysate mixture;
(d) heating the cell lysate mixture to a temperature that inactivates native enzymatic activity but does not inactivate the thermostable enzymes of step (a) to produce a heat-inactivated lysate;
(e) adding to the heat-inactivated lysate at least one purified enzyme selected from the group consisting of thermostable cellodextrin phosphorylases, thermostable phosphoglucomutases, thermostable phosphoglucoisomerases, thermostable allulose 6-phosphate epimerases, and thermostable allulose 6-phosphate phosphatases to produce a reaction mixture comprising a cellodextrin phosphorylase, a phosphoglucomutase, a phosphoglucoisomerase, an allulose 6-phosphate epimerase, and an allulose 6-phosphate phosphatase; and
(f) incubating the reaction mixture in the presence of a cellodextrin and inorganic phosphate to produce allulose.

58. The cell-free method of any one of embodiments 55-57, wherein the thermostable cellodextrin phosphorylase(s) is selected from the group consisting of *Aquifex aeolicus, Thermocrinis minervae, Thermosulfidibacter takaii, Thermosulfurimonas dismutans, Thermococcus litoralis, Palaeococcus pacificus, Thermotoga neapolitana, Ruminiclostridium thermocellum, Pyrococcus abyssi, Thermococcus thioreducens, Deinococcus radiodurans, Sulfolobus acidocaldarius, Thermus caldophilus, Meiothermus silvanus, Oceanithermus profundus, Ardenticatena maritima, Thermococcus barophilus, Pseudothermotoga thermarum, Hydrogenobacter thermophilus, Thermus oshimai, Meiothermus ruber*, and *Marinitoga piezophila* cellodextrin phosphorylases.

59. The cell-free method of any one of embodiments 55-58, wherein the thermostable phosphoglucomutase(s) is selected from the group consisting of *Thermococcus kodakaraensis, Pyrococcus kukulkanii, Ammonifex degensii, Methanothermobacter wolfeii, Methanothermus fervidus, Sulfolobus acidocaldarius, Archaeoglobus fulgidus, Ferroglobus placidus, Geoglobus ahangari, Archaeoglobus veneficus, Archaeoglobus sulfaticallidus, Aciduliprofundum boonie, Clostridium thermocellum, Defluviitalea phaphyphila, Caminicella sporogenes, Caloranaerobacter ferrireducens, Thermosipho malanesiensis, Fervidobacterium pennivorans, Symbiobacterium thermophilum, Spirochaeta thermophila*, and *Thermoanaerobacter wiegelii* phosphoglucomutases.

60. The cell-free method of any one of embodiments 55-59, wherein the thermostable phosphoglucomutase(s) is selected from the group consisting of *Thermus thermophilus, Meiothermus timidus, Thermus filiformis, Marinithermus hydrothermalis, Thermosipho africanus, Sulfurihydrogenibium azorense, Persephonella marina, Marinitoga piezophila, Kosmotoga olearia, Thermotoga maritima, Geobacillus stearothermophilus, Anoxybacillus flavithermus, Thermosulfidibacter takaii, Fervidobacterium nodosum, Clostridium thermocellum, Thermoanaerobacterium thermosaccharolyticum, Methanococcus jannaschii, Methanotorris igneus, Methanocaldococcus villosus, Methanother-*

*mococcus okinawensis, Pseudothermotoga thermarum, Deferribacter desulfuricans*, and *Thermovibrio ammonificans*, phosphoglucomutases.

61. The cell-free method of any one of embodiments 55-60, wherein the thermostable allulose 6-phosphate epimerase(s) is selected from the group consisting of *Thermobacterium thermosaccharolyticum, Thermoanaerobacter brockii, Caldanaerobacter subterraneus, Deferribacter desulfuricans, Thermocrinis ruber, Hydrogenivirga* sp. 128-5-R1-1, *Brevibacillus thermoruber, Thermosipho atlanticus*, and *Thermosulfidibacter takaii* allulose 6-phosphate epimerases.

62. The cell-free method of any one of embodiments 55-61, wherein the thermostable allulose 6-phosphate phosphatase(s) is selected from the group consisting of *Thermoanaerobacter wiegelii, Thermoanaerobacter ethanolicus, Thermus islandicus, Deinococcus geothermalis* DSM 11300, *Thermosphaera aggregans, Crenarchaeota archaeon, Pyrococcus horikoshii* Ot3, *Aquifex aeolicus, Ruminiclostridium thermocellum, Desulfotomaculum kuznetsovii, Caldanaerobacter subterraneus, Acidothermus cellulolyticus, Methanothermobacter thermautotrophicus, Thermobifida fusca, Thermotoga neapolitana, Petrotoga mobilis*, and *Thermodesulfatator indicus*, and *Thermus thermophilus* allulose 6-phosphate phosphatases.

63. A cell-free method for producing glucose, the method comprising:
   (a) culturing cells engineered to express a thermostable cellodextrin phosphorylase, a thermostable phosphoglucomutase, and a thermostable glucose 6-phosphate phosphatase to produce cultured cells that express the thermostable enzymes;
   (b) lysing the cultured cells to produce a cell lysate;
   (c) heating the cell lysate to a temperature that inactivates native enzymatic activity but does not inactivate the thermostable enzymes of step (a) to produce a heat-inactivated lysate; and
   (d) incubating the heat-inactivated lysate in the presence of a cellodextrin and inorganic phosphate to produce glucose.

64. A cell-free method for producing glucose, the method comprising:
   (a) culturing at least two cell populations, wherein cells of each population are engineered to express at least one enzyme selected from the group consisting of thermostable cellodextrin phosphorylases, thermostable phosphoglucomutases, and thermostable glucose 6-phosphate phosphatases to produce at least two cultured populations of cells expressing different enzymes;
   (b) lysing cells of the at least two cultured populations to produce at least two cell lysates;
   (c) combining the at least two cell lysates to produce a cell lysate mixture that comprises a thermostable cellodextrin phosphorylase, a thermostable phosphoglucomutase, and a thermostable glucose 6-phosphate phosphatase;
   (d) heating the cell lysate mixture to a temperature that inactivates native enzymatic activity but does not inactivate the thermostable enzymes of step (c) to produce a heat-inactivated lysate; and
   (e) incubating the reaction mixture in the presence of a cellodextrin and inorganic phosphate to produce glucose.

65. A cell-free method for producing glucose, the method comprising:
   (a) culturing at least two cell populations, wherein cells of each population are engineered to express at least one enzyme selected from the group consisting of thermostable cellodextrin phosphorylases, thermostable phosphoglucomutases, and thermostable glucose 6-phosphate phosphatases to produce at least two cultured populations of cells expressing different enzymes;
   (b) lysing cells of the at least two cultured populations to produce at least two cell lysates;
   (c) combining the at least two cell lysates to produce a cell lysate mixture;
   (d) heating the cell lysate mixture to a temperature that inactivates native enzymatic activity but does not inactivate the thermostable enzymes of step (a) to produce a heat-inactivated lysate;
   (e) adding to the heat-inactivated lysate at least one purified enzyme selected from the group consisting of thermostable cellodextrin phosphorylases, thermostable phosphoglucomutases, and thermostable glucose 6-phosphate phosphatases to produce a reaction mixture comprising a cellodextrin phosphorylase, a phosphoglucomutase, and a glucose 6-phosphate phosphatase; and
   (f) incubating the reaction mixture in the presence of a cellodextrin and inorganic phosphate to produce glucose.

66. A cell-free method for producing fructose, the method comprising:
   (a) culturing cells engineered to express a thermostable cellodextrin phosphorylase, a thermostable phosphoglucomutase, a thermostable phosphoglucoisomerase, and a thermostable fructose 6-phosphate phosphatase to produce cultured cells that express the thermostable enzymes;
   (b) lysing the cultured cells to produce a cell lysate;
   (c) heating the cell lysate to a temperature that inactivates native enzymatic activity but does not inactivate the thermostable enzymes of step (a) to produce a heat-inactivated lysate; and
   (d) incubating the heat-inactivated lysate in the presence of a cellodextrin and inorganic phosphate to produce fructose.

67. A cell-free method for producing fructose, the method comprising:
   (a) culturing at least two cell populations, wherein cells of each population are engineered to express at least one enzyme selected from the group consisting of thermostable cellodextrin phosphorylases, thermostable phosphoglucomutases, thermostable phosphoglucoisomerases, and thermostable fructose 6-phosphate phosphatases to produce at least two cultured populations of cells expressing different enzymes;
   (b) lysing cells of the at least two cultured populations to produce at least two cell lysates;
   (c) combining the at least two cell lysates to produce a cell lysate mixture that comprises a thermostable cellodextrin phosphorylase, a thermostable phosphoglucomutase, a thermostable phosphoglucoisomerase, and a thermostable fructose 6-phosphate phosphatase;
   (d) heating the cell lysate mixture to a temperature that inactivates native enzymatic activity but does not inactivate the thermostable enzymes of step (c) to produce a heat-inactivated lysate; and
   (e) incubating the reaction mixture in the presence of a cellodextrin and inorganic phosphate to produce fructose.

68. A cell-free method for producing fructose, the method comprising:
  (a) culturing at least two cell populations, wherein cells of each population are engineered to express at least one enzyme selected from the group consisting of thermostable cellodextrin phosphorylases, thermostable phosphoglucomutases, thermostable phosphoglucoisomerases, and thermostable fructose 6-phosphate phosphatases to produce at least two cultured populations of cells expressing different enzymes;
  (b) lysing cells of the at least two cultured populations to produce at least two cell lysates;
  (c) combining the at least two cell lysates to produce a cell lysate mixture;
  (d) heating the cell lysate mixture to a temperature that inactivates native enzymatic activity but does not inactivate the thermostable enzymes of step (a) to produce a heat-inactivated lysate;
  (e) adding to the heat-inactivated lysate at least one purified enzyme selected from the group consisting of thermostable cellodextrin phosphorylases, thermostable phosphoglucomutases, thermostable phosphoglucoisomerases, and thermostable fructose 6-phosphate phosphatases to produce a reaction mixture comprising a cellodextrin phosphorylase, a phosphoglucomutase, a phosphoglucoisomerase, and a fructose 6-phosphate phosphatase; and
  (f) incubating the reaction mixture in the presence of a cellodextrin and inorganic phosphate to produce fructose.

69. A cell-free method for producing sorbitol, the method comprising:
  (a) culturing cells engineered to express a thermostable cellodextrin phosphorylase, a thermostable phosphoglucomutase, a thermostable aldose dehydrogenase, and a thermostable sorbitol-6-phosphate phosphatase to produce cultured cells that express the thermostable enzymes;
  (b) lysing the cultured cells to produce a cell lysate;
  (c) heating the cell lysate to a temperature that inactivates native enzymatic activity but does not inactivate the thermostable enzymes of step (a) to produce a heat-inactivated lysate; and
  (d) incubating the heat-inactivated lysate in the presence of a cellodextrin and inorganic phosphate to produce sorbitol.

70. A cell-free method for producing sorbitol, the method comprising:
  (a) culturing at least two cell populations, wherein cells of each population are engineered to express at least one enzyme selected from the group consisting of thermostable cellodextrin phosphorylases, thermostable phosphoglucomutases, thermostable aldose dehydrogenases, and thermostable sorbitol-6-phosphate phosphatases to produce at least two cultured populations of cells expressing different enzymes;
  (b) lysing cells of the at least two cultured populations to produce at least two cell lysates;
  (c) combining the at least two cell lysates to produce a cell lysate mixture that comprises a thermostable cellodextrin phosphorylase, a thermostable phosphoglucomutase, a thermostable aldose dehydrogenase, and a thermostable sorbitol-6-phosphate phosphatase;
  (d) heating the cell lysate mixture to a temperature that inactivates native enzymatic activity but does not inactivate the thermostable enzymes of step (c) to produce a heat-inactivated lysate; and
  (e) incubating the reaction mixture in the presence of a cellodextrin and inorganic phosphate to produce sorbitol.

71. A cell-free method for producing sorbitol, the method comprising:
  (a) culturing at least two cell populations, wherein cells of each population are engineered to express at least one enzyme selected from the group consisting of thermostable cellodextrin phosphorylases, thermostable phosphoglucomutases, thermostable aldose dehydrogenases, and thermostable sorbitol-6-phosphate phosphatases to produce at least two cultured populations of cells expressing different enzymes;
  (b) lysing cells of the at least two cultured populations to produce at least two cell lysates;
  (c) combining the at least two cell lysates to produce a cell lysate mixture;
  (d) heating the cell lysate mixture to a temperature that inactivates native enzymatic activity but does not inactivate the thermostable enzymes of step (a) to produce a heat-inactivated lysate;
  (e) adding to the heat-inactivated lysate at least one purified enzyme selected from the group consisting of thermostable cellodextrin phosphorylases, thermostable phosphoglucomutases, thermostable aldose dehydrogenases, and thermostable sorbitol-6-phosphate phosphatases to produce a reaction mixture comprising a cellodextrin phosphorylase, a phosphoglucomutase, an aldose dehydrogenase, and a sorbitol-6-phosphate phosphatase; and
  (f) incubating the reaction mixture in the presence of a cellodextrin and inorganic phosphate to produce sorbitol.

72. A cell-free method for producing ribulose, the method comprising:
  (a) culturing cells engineered to express a thermostable cellodextrin phosphorylase, a thermostable phosphoglucomutase, a thermostable glucose 6-phosphate dehydrogenase, a thermostable 6-phosphogluconolactonase, a thermostable 6-phosphogluconate dehydrogenase, and a thermostable ribulose 5-phosphate phosphatase to produce cultured cells that express the thermostable enzymes;
  (b) lysing the cultured cells to produce a cell lysate;
  (c) heating the cell lysate to a temperature that inactivates native enzymatic activity but does not inactivate the thermostable enzymes of step (a) to produce a heat-inactivated lysate; and
  (d) incubating the heat-inactivated lysate in the presence of a cellodextrin and inorganic phosphate to produce ribulose.

73. A cell-free method for producing ribulose, the method comprising:
  (a) culturing at least two cell populations, wherein cells of each population are engineered to express at least one enzyme selected from the group consisting of thermostable cellodextrin phosphorylases, thermostable phosphoglucomutases, thermostable glucose 6-phosphate dehydrogenases, thermostable 6-phosphogluconolactonases, thermostable 6-phosphogluconate dehydrogenases, and thermostable ribulose 5-phosphate phosphatases to produce at least two cultured populations of cells expressing different enzymes;
  (b) lysing cells of the at least two cultured populations to produce at least two cell lysates;
  (c) combining the at least two cell lysates to produce a cell lysate mixture that comprises a thermostable cellodextrin phosphorylase, a thermostable phosphoglucomutase, a thermostable glucose 6-phosphate dehydrogenase, a thermostable 6-phosphogluconolactonase, a thermostable 6-phosphogluconate dehydrogenase, and a thermostable ribulose 5-phosphate phosphatase;
(d) heating the cell lysate mixture to a temperature that inactivates native enzymatic activity but does not inactivate the thermostable enzymes of step (c) to produce a heat-inactivated lysate; and
(e) incubating the reaction mixture in the presence of a cellodextrin and inorganic phosphate to produce ribulose.

74. A cell-free method for producing ribulose, the method comprising:
(a) culturing at least two cell populations, wherein cells of each population are engineered to express at least one enzyme selected from the group consisting of thermostable cellodextrin phosphorylases, thermostable phosphoglucomutases, thermostable glucose 6-phosphate dehydrogenases, thermostable 6-phosphogluconolactonases, thermostable 6-phosphogluconate dehydrogenases, and thermostable ribulose 5-phosphate phosphatases to produce at least two cultured populations of cells expressing different enzymes;
(b) lysing cells of the at least two cultured populations to produce at least two cell lysates;
(c) combining the at least two cell lysates to produce a cell lysate mixture;
(d) heating the cell lysate mixture to a temperature that inactivates native enzymatic activity but does not inactivate the thermostable enzymes of step (a) to produce a heat-inactivated lysate;
(e) adding to the heat-inactivated lysate at least one purified enzyme selected from the group consisting of thermostable cellodextrin phosphorylases, thermostable phosphoglucomutases, thermostable glucose 6-phosphate dehydrogenases, thermostable 6-phosphogluconolactonases, thermostable 6-phosphogluconate dehydrogenases, and thermostable ribulose 5-phosphate phosphatases to produce a reaction mixture comprising a cellodextrin phosphorylase, a phosphoglucomutase, a glucose 6-phosphate dehydrogenase, a 6-phosphogluconolactonase, a 6-phosphogluconate dehydrogenase, and a ribulose 5-phosphate phosphatase; and
(f) incubating the reaction mixture in the presence of a cellodextrin and inorganic phosphate to produce ribulose.

75. A cell-free method for producing ribose, the method comprising:
(a) culturing cells engineered to express a thermostable cellodextrin phosphorylase, a thermostable phosphoglucomutase, a thermostable glucose 6-phosphate dehydrogenase, a thermostable 6-phosphogluconolactonase, a thermostable 6-phosphogluconate dehydrogenase, a thermostable ribose 5-phosphate isomerase, and a thermostable ribose 5-phosphate phosphatase to produce cultured cells that express the thermostable enzymes;
(b) lysing the cultured cells to produce a cell lysate;
(c) heating the cell lysate to a temperature that inactivates native enzymatic activity but does not inactivate the thermostable enzymes of step (a) to produce a heat-inactivated lysate; and
(d) incubating the heat-inactivated lysate in the presence of a cellodextrin and inorganic phosphate to produce ribose.

76. A cell-free method for producing ribose, the method comprising:
(a) culturing at least two cell populations, wherein cells of each population are engineered to express at least one enzyme selected from the group consisting of thermostable cellodextrin phosphorylases, thermostable phosphoglucomutases, thermostable glucose 6-phosphate dehydrogenases, thermostable 6-phosphogluconolactonases, thermostable 6-phosphogluconate dehydrogenases, thermostable ribose 5-phosphate isomerases, and thermostable ribose 5-phosphate phosphatases to produce at least two cultured populations of cells expressing different enzymes;
(b) lysing cells of the at least two cultured populations to produce at least two cell lysates;
(c) combining the at least two cell lysates to produce a cell lysate mixture that comprises a thermostable cellodextrin phosphorylase, a thermostable phosphoglucomutase, a thermostable glucose 6-phosphate dehydrogenase, a thermostable 6-phosphogluconolactonase, a thermostable 6-phosphogluconate dehydrogenase, a thermostable ribose 5-phosphate isomerase, and a thermostable ribose 5-phosphate phosphatase;
(d) heating the cell lysate mixture to a temperature that inactivates native enzymatic activity but does not inactivate the thermostable enzymes of step (c) to produce a heat-inactivated lysate; and
(e) incubating the reaction mixture in the presence of a cellodextrin and inorganic phosphate to produce ribose.

77. A cell-free method for producing ribose, the method comprising:
(a) culturing at least two cell populations, wherein cells of each population are engineered to express at least one enzyme selected from the group consisting of thermostable cellodextrin phosphorylases, thermostable phosphoglucomutases, thermostable glucose 6-phosphate dehydrogenases, thermostable 6-phosphogluconolactonases, thermostable 6-phosphogluconate dehydrogenases, thermostable ribose 5-phosphate isomerases, and thermostable ribose 5-phosphate phosphatases to produce at least two cultured populations of cells expressing different enzymes;
(b) lysing cells of the at least two cultured populations to produce at least two cell lysates;
(c) combining the at least two cell lysates to produce a cell lysate mixture;
(d) heating the cell lysate mixture to a temperature that inactivates native enzymatic activity but does not inactivate the thermostable enzymes of step (a) to produce a heat-inactivated lysate;
(e) adding to the heat-inactivated lysate at least one purified enzyme selected from the group consisting of thermostable cellodextrin phosphorylases, thermostable phosphoglucomutases, thermostable glucose 6-phosphate dehydrogenases, thermostable 6-phosphogluconolactonases, thermostable 6-phosphogluconate dehydrogenases, thermostable ribose 5-phosphate isomerases, and thermostable ribose 5-phosphate phosphatases to produce a reaction mixture comprising a cellodextrin phosphorylase, a phosphoglucomutase, a glucose 6-phosphate dehydrogenase, a 6-phosphogluconolactonase, a 6-phosphogluconate dehydrogenase, a ribose 5-phosphate isomerase, and a ribose 5-phosphate phosphatase; and
(f) incubating the reaction mixture in the presence of a cellodextrin and inorganic phosphate to produce ribose.

78. A cell-free method for producing arabinose, the method comprising:
- (a) culturing cells engineered to express a thermostable cellodextrin phosphorylase, a thermostable phosphoglucomutase, a thermostable glucose 6-phosphate dehydrogenase, a thermostable 6-phosphogluconolactonase, a thermostable 6-phosphogluconate dehydrogenase, a thermostable arabinose 5-phosphate isomerase, and a thermostable arabinose 5-phosphate phosphatase to produce cultured cells that express the thermostable enzymes;
- (b) lysing the cultured cells to produce a cell lysate;
- (c) heating the cell lysate to a temperature that inactivates native enzymatic activity but does not inactivate the thermostable enzymes of step (a) to produce a heat-inactivated lysate; and
- (d) incubating the heat-inactivated lysate in the presence of a cellodextrin and inorganic phosphate to produce arabinose.

79. A cell-free method for producing arabinose, the method comprising:
- (a) culturing at least two cell populations, wherein cells of each population are engineered to express at least one enzyme selected from the group consisting of thermostable cellodextrin phosphorylases, thermostable phosphoglucomutases, thermostable glucose 6-phosphate dehydrogenases, thermostable 6-phosphogluconolactonases, thermostable 6-phosphogluconate dehydrogenases, thermostable arabinose 5-phosphate isomerases, and thermostable arabinose 5-phosphate phosphatases to produce at least two cultured populations of cells expressing different enzymes;
- (b) lysing cells of the at least two cultured populations to produce at least two cell lysates;
- (c) combining the at least two cell lysates to produce a cell lysate mixture that comprises a thermostable cellodextrin phosphorylase, a thermostable phosphoglucomutase, a thermostable glucose 6-phosphate dehydrogenase, a thermostable 6-phosphogluconolactonase, a thermostable 6-phosphogluconate dehydrogenase, a thermostable arabinose 5-phosphate isomerase, and a thermostable arabinose 5-phosphate phosphatase;
- (d) heating the cell lysate mixture to a temperature that inactivates native enzymatic activity but does not inactivate the thermostable enzymes of step (c) to produce a heat-inactivated lysate; and
- (e) incubating the reaction mixture in the presence of a cellodextrin and inorganic phosphate to produce arabinose.

80. A cell-free method for producing arabinose, the method comprising:
- (a) culturing at least two cell populations, wherein cells of each population are engineered to express at least one enzyme selected from the group consisting of thermostable cellodextrin phosphorylases, thermostable phosphoglucomutases, thermostable glucose 6-phosphate dehydrogenases, thermostable 6-phosphogluconolactonases, thermostable 6-phosphogluconate dehydrogenases, thermostable arabinose 5-phosphate isomerases, and thermostable arabinose 5-phosphate phosphatases to produce at least two cultured populations of cells expressing different enzymes;
- (b) lysing cells of the at least two cultured populations to produce at least two cell lysates;
- (c) combining the at least two cell lysates to produce a cell lysate mixture;
- (d) heating the cell lysate mixture to a temperature that inactivates native enzymatic activity but does not inactivate the thermostable enzymes of step (a) to produce a heat-inactivated lysate;
- (e) adding to the heat-inactivated lysate at least one purified enzyme selected from the group consisting of thermostable cellodextrin phosphorylases, thermostable phosphoglucomutases, thermostable glucose 6-phosphate dehydrogenases, thermostable 6-phosphogluconolactonases, thermostable 6-phosphogluconate dehydrogenases, thermostable arabinose 5-phosphate isomerases, and thermostable arabinose 5-phosphate phosphatases to produce a reaction mixture comprising a cellodextrin phosphorylase, a phosphoglucomutase, a glucose 6-phosphate dehydrogenase, a 6-phosphogluconolactonase, a 6-phosphogluconate dehydrogenase, an arabinose 5-phosphate isomerase, and an arabinose 5-phosphate phosphatase; and
- (f) incubating the reaction mixture in the presence of a cellodextrin and inorganic phosphate to produce arabinose.

81. A cell-free method for producing mannose, the method comprising:
- (a) culturing cells engineered to express a thermostable cellodextrin phosphorylase, a thermostable phosphoglucomutase, a thermostable phosphoglucoisomerase, a thermostable mannose 6-phosphate epimerase, and a thermostable mannose 6-phosphate phosphatase to produce cultured cells that express the thermostable enzymes;
- (b) lysing the cultured cells to produce a cell lysate;
- (c) heating the cell lysate to a temperature that inactivates native enzymatic activity but does not inactivate the thermostable enzymes of step (a) to produce a heat-inactivated lysate; and
- (d) incubating the heat-inactivated lysate in the presence of a cellodextrin and inorganic phosphate to produce mannose.

82. A cell-free method for producing mannose, the method comprising:
- (a) culturing at least two cell populations, wherein cells of each population are engineered to express at least one enzyme selected from the group consisting of thermostable cellodextrin phosphorylases, thermostable phosphoglucomutases, thermostable phosphoglucoisomerases, thermostable mannose 6-phosphate epimerases, and thermostable mannose 6-phosphate phosphatases to produce at least two cultured populations of cells expressing different enzymes;
- (b) lysing cells of the at least two cultured populations to produce at least two cell lysates;
- (c) combining the at least two cell lysates to produce a cell lysate mixture that comprises a thermostable cellodextrin phosphorylase, a thermostable phosphoglucomutase, a thermostable phosphoglucoisomerase, a thermostable mannose 6-phosphate epimerase, and a thermostable mannose 6-phosphate phosphatase;
- (d) heating the cell lysate mixture to a temperature that inactivates native enzymatic activity but does not inactivate the thermostable enzymes of step (c) to produce a heat-inactivated lysate; and
- (e) incubating the reaction mixture in the presence of a cellodextrin and inorganic phosphate to produce mannose.

83. A cell-free method for producing mannose, the method comprising:
  (a) culturing at least two cell populations, wherein cells of each population are engineered to express at least one enzyme selected from the group consisting of thermostable cellodextrin phosphorylases, thermostable phosphoglucomutases, thermostable phosphoglucoisomerases, thermostable mannose 6-phosphate epimerases, and thermostable mannose 6-phosphate phosphatases to produce at least two cultured populations of cells expressing different enzymes;
  (b) lysing cells of the at least two cultured populations to produce at least two cell lysates;
  (c) combining the at least two cell lysates to produce a cell lysate mixture;
  (d) heating the cell lysate mixture to a temperature that inactivates native enzymatic activity but does not inactivate the thermostable enzymes of step (a) to produce a heat-inactivated lysate;
  (e) adding to the heat-inactivated lysate at least one purified enzyme selected from the group consisting of thermostable cellodextrin phosphorylases, thermostable phosphoglucomutases, thermostable phosphoglucoisomerases, thermostable mannose 6-phosphate epimerases, and thermostable mannose 6-phosphate phosphatases to produce a reaction mixture comprising a cellodextrin phosphorylase, a phosphoglucomutase, a phosphoglucoisomerase, an mannose 6-phosphate epimerase, and an mannose 6-phosphate phosphatase; and
  (f) incubating the reaction mixture in the presence of a cellodextrin and inorganic phosphate to produce mannose.

84. The method of any one of embodiments 1-80, wherein the cells comprise bacterial cells.

85. The method of any one of embodiments 1-80, wherein the cells comprise yeast cells.

86. The method of any one of embodiments 1-85, wherein at least one of the enzymes is heterologous to the cells.

87. The method of any one of embodiments 1-86, wherein lysing step (b) comprises mechanically, chemically, or enzymatically lysing the cultured cells.

88. The method for any one of embodiments 1-87, wherein heating step (c) comprises heating the cell lysate to a temperature of at least 50° C.

89. The method for any one of embodiments 1-88, wherein the cellodextrin comprises amylose, amylopectin, or both amylose and amylopectin.

90. The method for any one of embodiments 1-89, wherein the thermostable cellodextrin phosphorylase and the thermostable phosphoglucomutase are expressed as a single fusion protein or a bifunctional protein.

91. A cell lysate produced by the method for any one of embodiments 1-90.

92. An engineered cell comprising a cellodextrin phosphorylase, a phosphoglucomutase, and a glucose 6-phosphate phosphatase, optionally wherein at least one of the foregoing enzymes is a thermostable enzyme.

93. An engineered cell comprising a cellodextrin phosphorylase, a phosphoglucomutase, a phosphoglucoisomerase, and a fructose 6-phosphate phosphatase, optionally wherein at least one of the foregoing enzymes is a thermostable enzyme.

94. An engineered cell comprising a cellodextrin phosphorylase, a phosphoglucomutase, a phosphoglucoisomerase, an allulose 6-phosphate epimerase, and an allulose 6-phosphate phosphatase, optionally wherein at least one of the foregoing enzymes is a thermostable enzyme.

95. An engineered cell comprising a cellodextrin phosphorylase, a phosphoglucomutase, a aldose dehydrogenase, and a sorbitol-6-phosphate phosphatase, optionally wherein at least one of the foregoing enzymes is a thermostable enzyme.

96. An engineered cell comprising a cellodextrin phosphorylase, a phosphoglucomutase, a glucose 6-phosphate dehydrogenase, a 6-phosphogluconolactonase, a 6-phosphogluconate dehydrogenase, and a ribulose 5-phosphate phosphatase, optionally wherein at least one of the foregoing enzymes is a thermostable enzyme.

97. An engineered cell comprising a cellodextrin phosphorylase, a phosphoglucomutase, a glucose 6-phosphate dehydrogenase, a 6-phosphogluconolactonase, a 6-phosphogluconate dehydrogenase, a ribose 5-phosphate isomerase, and a ribose 5-phosphate phosphatase, optionally wherein at least one of the foregoing enzymes is a thermostable enzyme.

98. An engineered cell comprising a cellodextrin phosphorylase, a phosphoglucomutase, a glucose 6-phosphate dehydrogenase, a 6-phosphogluconolactonase, a 6-phosphogluconate dehydrogenase, an arabinose 5-phosphate isomerase, and an arabinose 5-phosphate phosphatase, optionally wherein at least one of the foregoing enzymes is a thermostable enzyme.

99. An engineered cell comprising a cellodextrin phosphorylase, a phosphoglucomutase, a phosphoglucoisomerase, an mannose 6-phosphate epimerase, and an mannose 6-phosphate phosphatase, optionally wherein at least one of the foregoing enzymes is a thermostable enzyme.

100. The engineered cell of any one of embodiments embodiment 35-41, wherein the cell is a bacterial cell or a yeast cell.

101. A single cell lysate, a mixture of cell lysates obtained from at least two cell populations, or a reaction mixture comprising a cellodextrin phosphorylase, a phosphoglucomutase, and a glucose 6-phosphate phosphatase, optionally wherein at least one of the foregoing enzymes is a thermostable enzyme.

102. A single cell lysate, a mixture of cell lysates obtained from at least two cell populations, or a reaction mixture comprising a cellodextrin phosphorylase, a phosphoglucomutase, a phosphoglucoisomerase, and a fructose 6-phosphate phosphatase, optionally wherein at least one of the foregoing enzymes is a thermostable enzyme.

103. A single cell lysate, a mixture of cell lysates obtained from at least two cell populations, or a reaction mixture comprising a cellodextrin phosphorylase, a phosphoglucomutase, a phosphoglucoisomerase, an allulose 6-phosphate epimerase, and an allulose 6-phosphate phosphatase, optionally wherein at least one of the foregoing enzymes is a thermostable enzyme.

104. A single cell lysate, a mixture of cell lysates obtained from at least two cell populations, or a reaction mixture comprising a cellodextrin phosphorylase, a phosphoglucomutase, a aldose dehydrogenase, and a sorbitol-6-phosphate phosphatase, optionally wherein at least one of the foregoing enzymes is a thermostable enzyme.

105. A single cell lysate, a mixture of cell lysates obtained from at least two cell populations, or a reaction mixture comprising a cellodextrin phosphorylase, a phosphoglucomutase, a glucose 6-phosphate dehydrogenase, a 6-phosphogluconolactonase, a 6-phosphogluconate dehydrogenase, and a ribulose 5-phosphate phosphatase, optionally wherein at least one of the foregoing enzymes is a thermostable enzyme.

106. A single cell lysate, a mixture of cell lysates obtained from at least two cell populations, or a reaction mixture comprising a cellodextrin phosphorylase, a phosphoglucomutase, a glucose 6-phosphate dehydrogenase, a 6-phosphogluconolactonase, a 6-phosphogluconate dehydrogenase, a ribose 5-phosphate isomerase, and a ribose 5-phosphate phosphatase, optionally wherein at least one of the foregoing enzymes is a thermostable enzyme.

107. A single cell lysate, a mixture of cell lysates obtained from at least two cell populations, or a reaction mixture comprising a cellodextrin phosphorylase, a phosphoglucomutase, a glucose 6-phosphate dehydrogenase, a 6-phosphogluconolactonase, a 6-phosphogluconate dehydrogenase, an arabinose 5-phosphate isomerase, and an arabinose 5-phosphate phosphatase, optionally wherein at least one of the foregoing enzymes is a thermostable enzyme.

108. A single cell lysate, a mixture of cell lysates obtained from at least two cell populations, or a reaction mixture comprising a cellodextrin phosphorylase, a phosphoglucomutase, a phosphoglucoisomerase, an mannose 6-phosphate epimerase, and an mannose 6-phosphate phosphatase, optionally wherein at least one of the foregoing enzymes is a thermostable enzyme.

109. A cell-free method for producing a sugar, the method comprising:
  (a) culturing cells engineered to express a thermostable α-glucan phosphorylase, a thermostable phosphoglucomutase, and at least one thermostable enzyme selected from the group consisting of isomerases, epimerases, dehydrogenases, and sugar phosphatases to produce cultured cells that express the enzymes;
  (b) lysing cultured cells of step (a) to produce a cell lysate;
  (c) heating the cell lysate to a temperature that inactivates native enzymatic activity but does not inactivate the thermostable enzymes of step (a) to produce a heat-inactivated lysate; and
  (d) incubating the heat-inactivated lysate in the presence of a starch and inorganic phosphate to produce the sugar.

110. The method for embodiment 109, wherein the at least one thermostable enzyme is an isomerase selected from the group consisting of: phosphoglucoisomerase, ribose 5-phosphate isomerase, and arabinose 5-phosphate isomerase.

111. The method for embodiment 109 or 110, wherein the at least one thermostable enzyme is allulose 6-phosphate epimerase.

112. The method for any one of embodiments 109-111, wherein the at least one thermostable enzyme is a dehydrogenase selected from the group consisting of aldose dehydrogenase, glucose 6-phosphate dehydrogenase, and 6-phosphogluconate dehydrogenase.

113. The method for any one of embodiments 109-112, wherein the at least one thermostable enzyme is a sugar phosphatase selected from the group consisting of glucose 6-phosphate phosphatase, fructose 6-phosphate phosphatase, allulose 6-phosphate phosphatase, sorbitol-6-phosphate phosphatase, ribulose 5-phosphate phosphatase, ribose 5-phosphate phosphatase, and arabinose 5-phosphate phosphatase.

114. The method for embodiment 109, wherein the sugar is selected from the group consisting of glucose, fructose, allulose, sorbitol, ribulose, ribose, and arabinose.

115. The method for embodiment 114, wherein the sugar is glucose, and the at least one thermostable enzyme comprises glucose 6-phosphate phosphatase.

116. The method of embodiment 115, wherein the cells are engineered to express a thermostable α-glucan phosphorylase, a thermostable phosphoglucomutase, and a thermostable glucose 6-phosphate phosphatase.

117. The method for embodiment 114, wherein the sugar is fructose, and the at least one thermostable enzyme is selected from phosphoglucoisomerases and fructose 6-phosphate phosphatases.

118. The method for embodiment 117, wherein the cells are engineered to express a thermostable α-glucan phosphorylase, a thermostable phosphoglucomutase, a thermostable phosphoglucoisomerase, and a thermostable fructose 6-phosphate phosphatase.

119. The method for embodiment 114, wherein the sugar is allulose, and the at least one thermostable enzyme is selected from phosphoglucoisomerases, allulose 6-phosphate epimerases, and allulose 6-phosphate phosphatases.

120. The method for embodiment 119, wherein the cells are engineered to express a thermostable α-glucan phosphorylase, a thermostable phosphoglucomutase, a thermostable phosphoglucoisomerase, a thermostable allulose 6-phosphate epimerase, and a thermostable allulose 6-phosphate phosphatase.

121. The method for embodiment 114, wherein the sugar is sorbitol, and the at least one thermostable enzyme is selected from aldose dehydrogenases and sorbitol-6-phosphate phosphatases.

122. The method for embodiment 121, wherein the cells are engineered to express a thermostable α-glucan phosphorylase, a thermostable phosphoglucomutase, a thermostable aldose dehydrogenase, and a thermostable sorbitol-6-phosphate phosphatase.

123. The method for embodiment 114, wherein the sugar is ribulose, and the at least one thermostable enzyme is selected from glucose 6-phosphate dehydrogenases, 6-phosphogluconolactonases, 6-phosphogluconate dehydrogenases, and ribulose 5-phosphate phosphatases.

124. The method for embodiment 123, wherein the cells are engineered to express a thermostable α-glucan phosphorylase, a thermostable phosphoglucomutase, a thermostable glucose 6-phosphate dehydrogenase, a thermostable 6-phosphogluconolactonase, a thermostable 6-phosphogluconate dehydrogenase, and a thermostable ribulose 5-phosphate phosphatase.

125. The method for embodiment 114, wherein the sugar is ribose, and the at least one thermostable enzyme is selected from glucose 6-phosphate dehydrogenases, 6-phosphogluconolactonases, 6-phosphogluconate dehydrogenases, ribose 5-phosphate isomerases, and ribose 5-phosphate phosphatases.

126. The method for embodiment 125, wherein the cells are engineered to express a thermostable α-glucan phosphorylase, a thermostable phosphoglucomutase, a thermostable glucose 6-phosphate dehydrogenase, a thermostable 6-phosphogluconolactonase, a thermostable 6-phosphogluconate dehydrogenase, a thermostable ribose 5-phosphate isomerase, and a thermostable ribose 5-phosphate phosphatase.

127. The method for embodiment 114, wherein the sugar is arabinose, and the at least one thermostable enzyme is selected from glucose 6-phosphate dehydrogenases, 6-phosphogluconolactonases, 6-phosphogluconate dehydrogenases, arabinose 5-phosphate isomerases, and arabinose 5-phosphate phosphatases.

128. The method for embodiment 127, wherein the cells are engineered to express a thermostable α-glucan phosphorylase, a thermostable phosphoglucomutase, a thermostable glucose 6-phosphate dehydrogenase, a thermostable 6-phosphogluconolactonase, a thermostable 6-phosphogluconate dehydrogenase, a thermostable arabinose 5-phosphate isomerase, and a thermostable arabinose 5-phosphate phosphatase.

129. The method for any one of embodiments 109-128, wherein the cells are bacterial cells.

130. The method for any one of embodiments 109-128, wherein the cells are yeast cells.

131. The method for any one of embodiments 109-130, wherein the thermostable α-glucan phosphorylase, the thermostable phosphoglucomutase, and/or the at least one thermostable enzyme is/are heterologous to the cells.

132. The method for any one of embodiments 109-131, wherein lysing step (b) comprises mechanically, chemically, or enzymatically lysing the cultured cells.

133. The method for any one of embodiments 109-132, wherein heating step (c) comprises heating the cell lysate to a temperature of at least 50° C.

134. The method for any one of embodiments 109-133, wherein the starch comprises amylose, amylopectin, or both amylose and amylopectin.

135. The method for any one of embodiments 109-134, wherein the thermostable α-glucan phosphorylase and the thermostable phosphoglucomutase are expressed as a single fusion protein.

136. A cell-free method for producing a sugar, the method comprising:
(a) culturing cells engineered to express a α-glucan phosphorylase, a phosphoglucomutase, and at least one enzyme selected from the group consisting of isomerases, epimerases, dehydrogenases, and sugar phosphatases to produce cultured cells that express the enzymes;
(b) lysing cultured cells of step (a) to produce a cell lysate; and
(c) incubating the lysate in the presence of a starch and inorganic phosphate to produce the sugar.

137. A cell-free method for producing a sugar, the method comprising:
(a) culturing cells engineered to express (ii) a fusion protein that comprises a α-glucan phosphorylase fused to a phosphoglucomutase, and (ii) at least one enzyme selected from the group consisting of isomerases, epimerases, dehydrogenases, and sugar phosphatases to produce cultured cells that express the enzymes;
(b) lysing cultured cells of step (a) to produce a cell lysate; and
(c) incubating the lysate in the presence of a starch and inorganic phosphate to produce the sugar.

138. A cell-free method for producing a sugar, the method comprising:
(a) culturing cells engineered to express a fusion protein that comprises a α-glucan phosphorylase fused to a phosphoglucomutase;
(b) culturing cells engineered to express at least one enzyme selected from the group consisting of isomerases, epimerases, dehydrogenases, and sugar phosphatases to produce cultured cells that express the enzymes;
(c) lysing cultured cells of step (a) and step (b) to produce cell lysates; and
(d) incubating the lysates in the presence of a starch and inorganic phosphate to produce the sugar.

139. The method for embodiment 137 or 138, wherein the enzymes of steps (a) and/or (b) are thermostable enzymes.

140. The method for embodiment 139, wherein the method further comprises heating the cell lysate(s) to a temperature that inactivates native enzymatic activity but does not inactivate the thermostable enzymes to produce heat-inactivated lysate(s).

141. A cell lysate produced by the method for any one of embodiments 109-138.

142. An engineered cell comprising a thermostable α-glucan phosphorylase, a thermostable phosphoglucomutase, and at least one thermostable enzyme selected from the group consisting of isomerases, epimerases, dehydrogenases, and sugar phosphatases.

143. The engineered cell of embodiment 142 comprising:
(a) a thermostable α-glucan phosphorylase, a thermostable phosphoglucomutase, and a thermostable glucose 6-phosphate phosphatase;
(b) a thermostable α-glucan phosphorylase, a thermostable phosphoglucomutase, a phosphoglucoisomerase, and a fructose 6-phosphate phosphatase;
(c) a thermostable α-glucan phosphorylase, a thermostable phosphoglucomutase, a phosphoglucoisomerase, an allulose 6-phosphate epimerase, and an allulose 6-phosphate phosphatase;
(d) a thermostable α-glucan phosphorylase, a thermostable phosphoglucomutase, an aldose dehydrogenase, and a sorbitol-6-phosphate phosphatase;
(e) a thermostable α-glucan phosphorylase, a thermostable phosphoglucomutase, a glucose 6-phosphate dehydrogenase, a 6-phosphogluconolactonase, a 6-phosphogluconate dehydrogenase, and a ribulose 5-phosphate phosphatase;
(f) a thermostable α-glucan phosphorylase, a thermostable phosphoglucomutase, a glucose 6-phosphate dehydrogenase, a 6-phosphogluconolactonase, a 6-phosphogluconate dehydrogenase, a ribose 5-phosphate isomerase, and a ribose 5-phosphate phosphatase; or
(g) a thermostable α-glucan phosphorylase, a thermostable phosphoglucomutase, a glucose 6-phosphate dehydrogenase, a 6-phosphogluconolactonase, a 6-phosphogluconate dehydrogenase, an arabinose 5-phosphate isomerase, and an arabinose 5-phosphate phosphatase.

144. The engineered cell of embodiment 142 or 143, wherein the cell is a bacterial cell or a yeast cell.

EXAMPLES

Example 1

Cell Free Conversion of Starch to Allulose

This example describes the conversion of starch to allulose. Cells (e.g., bacterial or yeast cells) engineered to express at least one heterologous genes encoding at least one enzyme for the conversion of starch to allulose are grown in liquid cultures to high cell density. Examples of heterologous enzymes that may be used in this example include thermostable variants of a α-glucan phosphorylase (EC 2.4.1.1), a phosphoglucomutase (EC 5.4.2.2, 5.4.2.5, or 5.4.2.6), a phosphoglucoisomerase (EC 5.3.1.9), an allulose 6-phosphate epimerase (EC 5.3.1.–), and an allulose 6-phosphate phosphatase (EC 5.3.1.–). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A starch feedstock, inorganic phosphate and optionally other additional nutrients are added to the heat inactivated lysate to enable conversion of starch to allulose (FIG. 1).

Example 2

Cell Free Conversion of Starch to Glucose

Figure 2:
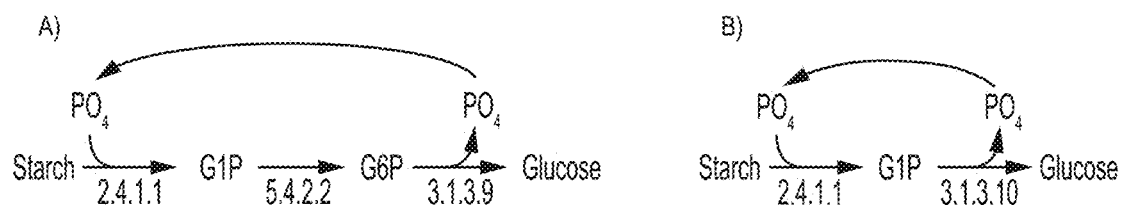
FIG. 2 is a schematic of two enzymatic pathways for the conversion of starch to glucose. The meaning of the abbreviations is as follows: G1P=glucose 1-phosphate, G6P=glucose 6-phosphate, and $PO_4$=inorganic phosphate.

This example describes the conversion of starch to glucose. Cells (e.g., bacterial or yeast cells) engineered to express at least one heterologous genes encoding at least one enzyme for the conversion of starch to glucose are grown in liquid cultures to high cell density. Examples of heterologous enzymes that may be used in this example include thermostable variants of a α-glucan phosphorylase (EC 2.4.1.1), a phosphoglucomutase (EC 5.4.2.2, 5.4.2.5, or 5.4.2.6) and a glucose 6-phosphate phosphatase (EC 5.3.1.–). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A starch feedstock, inorganic phosphate and optionally other additional nutrients are added to the heat inactivated lysate to enable conversion of starch to glucose (FIG. 2A).

This example also describes another pathway for the conversion of starch to glucose. Cells (e.g., bacterial or yeast cells) engineered to express at least one heterologous genes encoding at least one enzyme for the conversion of starch to glucose are grown in liquid cultures to high cell density. Examples of heterologous enzymes that may be used in this example include thermostable variants of a α-glucan phosphorylase (EC 2.4.1.1), and a glucose 1-phosphate phosphatase (EC 3.1.3.10). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A starch feedstock, inorganic phosphate and optionally other additional nutrients are added to the heat inactivated lysate to enable conversion of starch to glucose (FIG. 2B).

Example 3

Cell Free Conversion of Starch to Fructose

Figure 3:
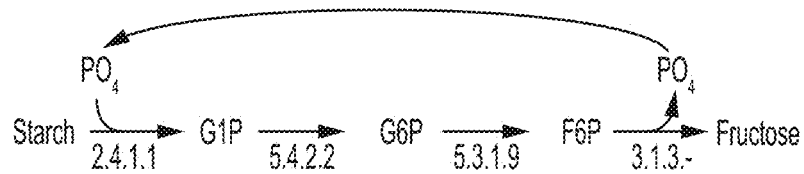
FIG. 3 is a schematic of two enzymatic pathways for the conversion of starch to fructose. The meaning of the abbreviations is as follows: G1P=glucose 1-phosphate, G6P=glucose 6-phosphate, F6P=fructose 6-phosphate, and $PO_4$=inorganic phosphate.

This example describes the conversion of starch to fructose. Cells (e.g., bacterial or yeast cells) engineered to express at least one heterologous genes encoding at least one enzyme for the conversion of starch to fructose are grown in liquid cultures to high cell density. Examples of heterologous enzymes that may be used in this example include thermostable variants of a α-glucan phosphorylase (EC 2.4.1.1), a phosphoglucomutase (EC 5.4.2.2, 5.4.2.5, or 5.4.2.6), a phosphoglucoisomerase (EC 5.3.1.9), and a fructose 6-phosphate phosphatase (EC 5.3.1.–). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A starch feedstock, inorganic phosphate and optionally other additional nutrients are added to the heat inactivated lysate to enable conversion of starch to fructose (FIG. 3).

Example 4

Cell Free Conversion of Starch to Sorbitol

Figure 4:
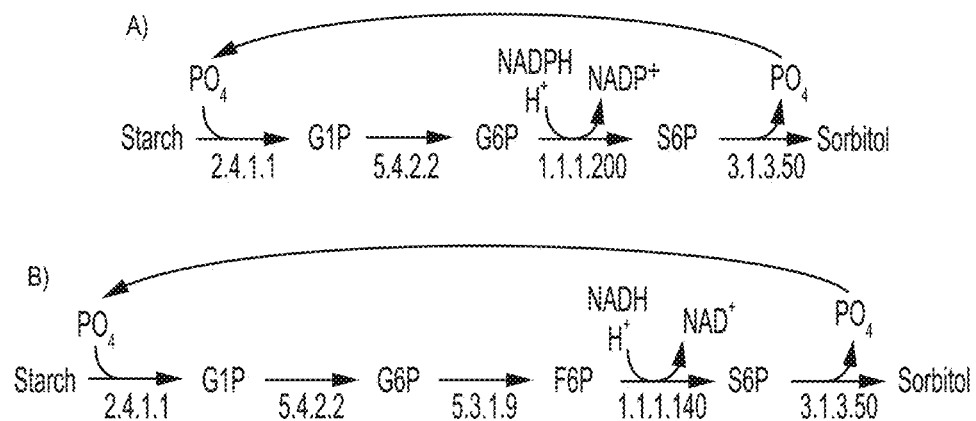
FIG. 4 is a schematic of an enzymatic pathway for the conversion of starch to sorbitol. The meaning of the abbreviations is as follows: G1P=glucose 1-phosphate, G6P=glucose 6-phosphate, S6P=sorbitol-6-phosphate, F6P=fructose 6-phosphate, NADPH=nicotinamide adenine dinucleotide phosphate (reduced form), $NADP^+$=nicotinamide adenine dinucleotide phosphate, and $PO_4$=inorganic phosphate.

This example describes the conversion of starch to sorbitol. Cells (e.g., bacterial or yeast cells) engineered to express at least one heterologous genes encoding at least one enzyme for the conversion of starch to sorbitol are grown in liquid cultures to high cell density. Examples of heterologous enzymes that may be used in this example include thermostable variants of a α-glucan phosphorylase (EC 2.4.1.1), a phosphoglucomutase (EC 5.4.2.2, 5.4.2.5, or 5.4.2.6), an aldose dehydrogenase (EC 1.1.1.200), and a sorbitol-6-phosphate phosphatase (EC 5.3.1.–). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A starch feedstock, inorganic phosphate and optionally other additional nutrients are added to the heat inactivated lysate to enable conversion of starch to sorbitol (FIG. 4).

Example 5

Cell Free Conversion of Starch to Ribulose

Figure 5:
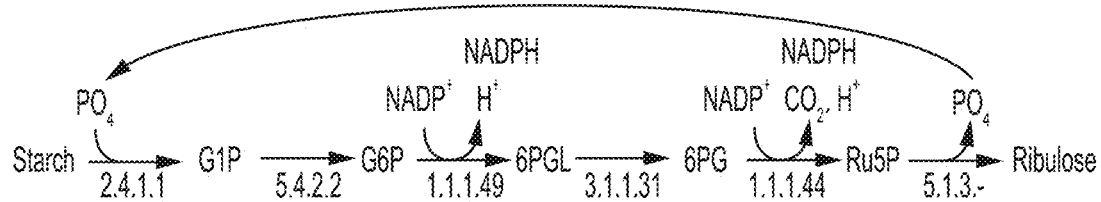
FIG. 5 is a schematic of an enzymatic pathway for the conversion of starch to ribulose. The meaning of the abbreviations is as follows: G1P=glucose 1-phosphate, G6P=glucose 6-phosphate, 6PGL=6-phosphogluconolactone, 6PG=6-phosphogluconate, Ru5P=ribulose 5-phosphate, NADPH=nicotinamide adenine dinucleotide phosphate (reduced form), $NADP^+$=nicotinamide adenine dinucleotide phosphate, $CO_2$=carbon dioxide, and $PO_4$=inorganic phosphate.

This example describes the conversion of starch to ribulose. Cells (e.g., bacterial or yeast cells) engineered to express at least one heterologous genes encoding at least one enzyme for the conversion of starch to ribulose are grown in liquid cultures to high cell density. Examples of heterologous enzymes that may be used in this example include thermostable variants of a α-glucan phosphorylase (EC 2.4.1.1), a phosphoglucomutase (EC 5.4.2.2, 5.4.2.5, or 5.4.2.6), a glucose 6-phosphate dehydrogenase (EC 1.1.1.49), a 6-phosphogluconolactonase (EC 3.1.1.31), a 6-phosphogluconate dehydrogenase (EC 1.1.1.44), and a ribulose 5-phosphate phosphatase (EC 5.3.1.–), and an ribulose 6-phosphate phosphatase (EC 5.3.1.–). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A starch feedstock, inorganic phosphate and optionally other additional nutrients are added to the heat inactivated lysate to enable conversion of starch to ribulose (FIG. 5).

Example 6

Cell Free Conversion of Starch to Ribose

Figure 6:
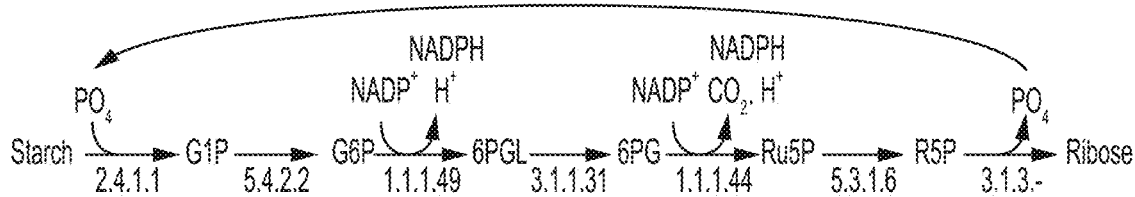
FIG. 6 is a schematic of an enzymatic pathway for the conversion of starch to ribose. The meaning of the abbreviations is as follows: G1P=glucose 1-phosphate, G6P=glucose 6-phosphate, 6PGL=6-phosphogluconolactone, 6PG=6-phosphogluconate, Ru5P=ribulose 5-phosphate, R5P=ribose 5-phosphate, NADPH=nicotinamide adenine dinucleotide phosphate (reduced form), $NADP^+$= nicotinamide adenine dinucleotide phosphate, $CO_2$=carbon dioxide, and $PO_4$=inorganic phosphate.

This example describes the conversion of starch to ribose. Cells (e.g., bacterial or yeast cells) engineered to express at least one heterologous genes encoding at least one enzyme for the conversion of starch to ribose are grown in liquid cultures to high cell density. Examples of heterologous enzymes that may be used in this example include thermostable variants of a α-glucan phosphorylase (EC 2.4.1.1), a phosphoglucomutase (EC 5.4.2.2, 5.4.2.5, or 5.4.2.6), a glucose 6-phosphate dehydrogenase (EC 1.1.1.49), a 6-phosphogluconolactonase (EC 3.1.1.31), a 6-phosphogluconate dehydrogenase (EC 1.1.1.44), a ribose 5-phosphate isomerase (EC 5.3.1.6) and a ribose 5-phosphate phosphatase (EC 5.3.1.–). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A starch feedstock, inorganic phosphate and optionally other additional nutrients are added to the heat inactivated lysate to enable conversion of starch to ribose (FIG. 6).

Example 7

Cell Free Conversion of Starch to Arabinose

Figure 7:
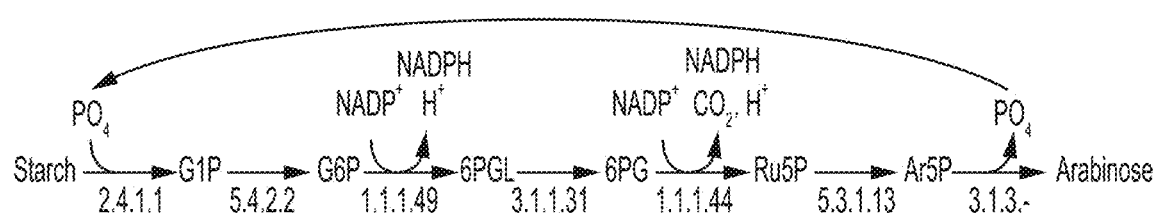
FIG. 7 is a schematic of an enzymatic pathway for the conversion of starch to arabinose. The meaning of the abbreviations is as follows: G1P=glucose 1-phosphate, G6P=glucose 6-phosphate, 6PGL=6-phosphogluconolactone, 6PG=6-phosphogluconate, Ru5P=ribulose 5-phosphate, Ar5P=arabinose 5-phosphate, NADPH=nicotinamide adenine dinucleotide phosphate (reduced form), $NADP^+$= nicotinamide adenine dinucleotide phosphate, $CO_2$=carbon dioxide, and $PO_4$=inorganic phosphate.
Figure 8:
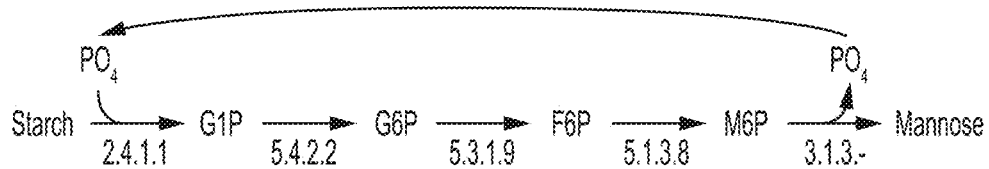
FIG. 8 is a schematic of an enzymatic pathway for the conversion of starch to mannose. The meaning of the abbreviations is as follows: G1P=glucose 1-phosphate, G6P=glucose 6-phosphate, F6P=fructose 6-phosphate, M6P=mannose 6-phosphate, and PO4=inorganic phosphate.

This example describes the conversion of starch to arabinose. Cells (e.g., bacterial or yeast cells) engineered to express at least one heterologous genes encoding at least one enzyme for the conversion of starch to arabinose are grown in liquid cultures to high cell density. Examples of heterologous enzymes that may be used in this example include thermostable variants of a α-glucan phosphorylase (EC 2.4.1.1), a phosphoglucomutase (EC 5.4.2.2, 5.4.2.5, or 5.4.2.6), a glucose 6-phosphate dehydrogenase (EC 1.1.1.49), a 6-phosphogluconolactonase (EC 3.1.1.31), a 6-phosphogluconate dehydrogenase (EC 1.1.1.44), an arabinose 5-phosphate isomerase (EC 5.3.1.6) and an arabinose 5-phosphate phosphatase (EC 5.3.1.–). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A starch feedstock, inorganic phosphate and optionally other additional nutrients are added to the heat inactivated lysate to enable conversion of starch to arabinose (FIG. 7).

Example 8

Cell Free Conversion of Cellulose/Cellodextrin to Allulose

This example describes the conversion of cellulose/cellodextrin to allulose. Cells (e.g., bacterial or yeast cells) engineered to express at least one heterologous genes encoding at least one enzyme for the conversion of cellulose/cellodextrin to allulose are grown in liquid cultures to high cell density. Examples of heterologous enzymes that may be used in this example include thermostable variants of a cellodextrin phosphorylase (EC 2.4.1.49), a phosphoglucomutase (EC 5.4.2.2, 5.4.2.5, or 5.4.2.6), a phosphoglucoisomerase (EC 5.3.1.9), an allulose 6-phosphate epimerase (EC 5.3.1.–), and an allulose 6-phosphate phosphatase (EC 5.3.1.–). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A cellulose/cellodextrin feedstock, inorganic phosphate and optionally other additional nutrients are added to the heat inactivated lysate to enable conversion of cellulose/cellodextrin to allulose.

Example 9

Cell Free Conversion of Cellulose/Cellodextrin to Glucose

This example describes the conversion of cellulose/cellodextrin to glucose. Cells (e.g., bacterial or yeast cells) engineered to express at least one heterologous genes encoding at least one enzyme for the conversion of cellulose/cellodextrin to glucose are grown in liquid cultures to high cell density. Examples of heterologous enzymes that may be used in this example include thermostable variants of a cellodextrin phosphorylase (EC 2.4.1.49), a phosphoglucomutase (EC 5.4.2.2, 5.4.2.5, or 5.4.2.6) and a glucose 6-phosphate phosphatase (EC 5.3.1.–). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A cellulose/cellodextrin feedstock, inorganic phosphate and optionally other additional nutrients are added to the heat inactivated lysate to enable conversion of cellulose/cellodextrin to glucose.

This example also describes another pathway for the conversion of cellulose/cellodextrin to glucose. Cells (e.g., bacterial or yeast cells) engineered to express at least one heterologous genes encoding at least one enzyme for the conversion of cellulose/cellodextrin to glucose are grown in liquid cultures to high cell density. Examples of heterologous enzymes that may be used in this example include thermostable variants of a cellodextrin phosphorylase (EC 2.4.1.49), and a glucose 1-phosphate phosphatase (EC 3.1.3.10). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A cellulose/cellodextrin feedstock, inorganic phosphate and optionally other additional nutrients are added to the heat inactivated lysate to enable conversion of cellulose/cellodextrin to glucose.

Example 10

Cell Free Conversion of Cellulose/Cellodextrin to Fructose

This example describes the conversion of cellulose/cellodextrin to fructose. Cells (e.g., bacterial or yeast cells) engineered to express at least one heterologous genes encoding at least one enzyme for the conversion of cellulose/cellodextrin to fructose are grown in liquid cultures to high cell density. Examples of heterologous enzymes that may be used in this example include thermostable variants of a cellodextrin phosphorylase (EC 2.4.1.49), a phosphoglucomutase (EC 5.4.2.2, 5.4.2.5, or 5.4.2.6), a phosphoglucoisomerase (EC 5.3.1.9), and a fructose 6-phosphate phosphatase (EC 5.3.1.–). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A cellulose/cellodextrin feedstock, inorganic phosphate and optionally other additional nutrients are added to the heat inactivated lysate to enable conversion of cellulose/cellodextrin to fructose.

Example 11

Cell Free Conversion of Cellulose/Cellodextrin to Sorbitol

This example describes the conversion of cellulose/cellodextrin to sorbitol. Cells (e.g., bacterial or yeast cells) engineered to express at least one heterologous genes encoding at least one enzyme for the conversion of cellulose/cellodextrin to sorbitol are grown in liquid cultures to high cell density. Examples of heterologous enzymes that may be used in this example include thermostable variants of a cellodextrin phosphorylase (EC 2.4.1.49), a phosphoglucomutase (EC 5.4.2.2, 5.4.2.5, or 5.4.2.6), an aldose dehydrogenase (EC 1.1.1.200), and a sorbitol-6-phosphate phosphatase (EC 5.3.1.-). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A cellulose/cellodextrin feedstock, inorganic phosphate and optionally other additional nutrients are added to the heat inactivated lysate to enable conversion of cellulose/cellodextrin to sorbitol.

Example 12

Cell Free Conversion of Cellulose/Cellodextrin to Ribulose

This example describes the conversion of cellulose/cellodextrin to ribulose. Cells (e.g., bacterial or yeast cells) engineered to express at least one heterologous genes encoding at least one enzyme for the conversion of cellulose/cellodextrin to ribulose are grown in liquid cultures to high cell density. Examples of heterologous enzymes that may be used in this example include thermostable variants of a cellodextrin phosphorylase (EC 2.4.1.49), a phosphoglucomutase (EC 5.4.2.2, 5.4.2.5, or 5.4.2.6), a glucose 6-phosphate dehydrogenase (EC 1.1.1.49), a 6-phosphogluconolactonase (EC 3.1.1.31), a 6-phosphogluconate dehydrogenase (EC 1.1.1.44), and a ribulose 5-phosphate phosphatase (EC 5.3.1.-), and an ribulose 6-phosphate phosphatase (EC 5.3.1.-). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A cellulose/cellodextrin feedstock, inorganic phosphate and optionally other additional nutrients are added to the heat inactivated lysate to enable conversion of cellulose/cellodextrin to ribulose.

Example 13

Cell Free Conversion of Cellulose/Cellodextrin to Ribose

This example describes the conversion of cellulose/cellodextrin to ribose. Cells (e.g., bacterial or yeast cells) engineered to express at least one heterologous genes encoding at least one enzyme for the conversion of cellulose/cellodextrin to ribose are grown in liquid cultures to high cell density. Examples of heterologous enzymes that may be used in this example include thermostable variants of a cellodextrin phosphorylase (EC 2.4.1.49), a phosphoglucomutase (EC 5.4.2.2, 5.4.2.5, or 5.4.2.6), a glucose 6-phosphate dehydrogenase (EC 1.1.1.49), a 6-phosphogluconolactonase (EC 3.1.1.31), a 6-phosphogluconate dehydrogenase (EC 1.1.1.44), a ribose 5-phosphate isomerase (EC 5.3.1.6) and a ribose 5-phosphate phosphatase (EC 5.3.1.-). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A cellulose/cellodextrin feedstock, inorganic phosphate and optionally other additional nutrients are added to the heat inactivated lysate to enable conversion of cellulose/cellodextrin to ribose.

Example 14

Cell Free Conversion of Cellulose/cellodextrin to Arabinose

This example describes the conversion of cellulose/cellodextrin to arabinose. Cells (e.g., bacterial or yeast cells) engineered to express at least one heterologous genes encoding at least one enzyme for the conversion of cellulose/cellodextrin to arabinose are grown in liquid cultures to high cell density. Examples of heterologous enzymes that may be used in this example include thermostable variants of a cellodextrin phosphorylase (EC 2.4.1.49), a phosphoglucomutase (EC 5.4.2.2, 5.4.2.5, or 5.4.2.6), a glucose 6-phosphate dehydrogenase (EC 1.1.1.49), a 6-phosphogluconolactonase (EC 3.1.1.31), a 6-phosphogluconate dehydrogenase (EC 1.1.1.44), an arabinose 5-phosphate isomerase (EC 5.3.1.6) and an arabinose 5-phosphate phosphatase (EC 5.3.1.-). At the end of the growth stage, expression of the heterologous enzyme(s) is induced, and the cell biomass is subsequently harvested. The harvested biomass is then lysed via mechanical, chemical or enzymatic means. The cell lysate is then heated to a temperature that inactivates native enzymatic activities but does not inactivate the heterologous enzyme(s). A cellulose/cellodextrin feedstock, inorganic phosphate and optionally other additional nutrients are added to the heat inactivated lysate to enable conversion of cellulose/cellodextrin to arabinose.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for producing allulose, the method comprising:
   (i) converting fructose 6-phosphate (F6P) to allulose-6-phosphate (A6P), catalyzed by an allulose 6-phosphate epimerase (A6PE) selected from the group consisting of Thermobacterium *thermosaccharolyticum* A6PE, *Thermoanaerobacter* brockii A6PE, Caldanaerobacter *subterraneus* A6PE, Deferribacter *desulfuricans* A6PE, *Thermocrinis ruber* A6PE, *Hydrogenivirga* sp. 128-5-R1-1 A6PE, *Thermosipho atlanticus* A6PE, and *Thermosulfidibacter takaii* A6PE; and
   (ii) converting A6P to allulose, catalyzed by an allulose 6-phosphate phosphatase (A6PP) selected from the group consisting of *Thermoanaerobacter wiegelii* A6PP, *Thermoanaerobacter ethanolicus* A6PP, *Thermus islandicus* A6PP, *Deinococcus geothermalis* A6PP, *Thermosphaera aggregans* A6PP, Crenarchaeota archaeon A6PP, *Pyrococcus horikoshii* A6PP, *Aquifex aeolicus* A6PP, *Desulfotomaculum kuznetsovii* A6PP, *Caldanaerobacter subterraneus* A6PP, *Acidothermus cellulolyticus* A6PP, *Methanothermobacter thermautotrophicus* A6PP, *Thermobifida fusca* A6PP, *Thermotoga neapolitana* A6PP, *Petrotoga mobilis* A6PP, *Thermodesulfatator indicus* A6PP, *Thermus thermophilus* A6PP, *Bacteroides vulgatus* A6PP, and *Bacteroides fragilis* A6PP.

2. The method of claim 1, wherein the A6PE, the A6PP, or both the A6PE and A6PP are thermostable or engineered to be thermostable.

3. The method of claim 1 further comprising converting glucose 6-phosphate (G6P) to F6P, catalyzed by a phosphoglucoisomerase.

4. The method of claim 3 further comprising converting glucose 1-phosphate (G1P) to G6P, catalyzed by a phosphoglucomutase.

5. The method of claim 4 further comprising converting a polymeric glucose carbohydrate to G1P, catalyzed by an α-glucan phosphorylase or a cellodextrin phosphorylase.

6. The method of claim 5, wherein the polymeric glucose carbohydrate is selected from starches, cellodextrins, maltodextrins, and glycogens.

7. The method of claim 5 further comprising treating the polymeric glucose carbohydrate with a debranching enzyme.

8. The method of claim 7, wherein the debranching enzyme is selected from isoamylases and pullulanases.

9. A method for producing allulose, the method comprising:
   converting fructose 6-phosphate (F6P) to allulose 6-phosphate (A6P), catalyzed by an allulose 6-phosphate epimerase (A6PE), and
   converting A6P to allulose, catalyzed by an allulose 6-phosphate phosphatase (A6PP), in a cell lysate mixture comprising cell lysates from microbial cells that express one or both of the allulose 6-phosphate epimerase (A6PE) and the allulose 6-phosphate phosphatase (A6PP),
   wherein the A6PE is derived from an organism selected from the group consisting of Thermobacterium *thermosaccharolyticum*, *Thermoanaerobacter brockii*, *Caldanaerobacter subterraneus*, *Deferribacter desulfuricans*, *Thermocrinis ruber*, *Hydrogenivirga* sp. 128-5-R1-1, *Thermosipho atlanticus*, and *Thermosulfidibacter takaii*; and
   wherein the A6PP is derived from an organism selected from the group consisting of *Thermoanaerobacter wiegelii*, *Thermoanaerobacter ethanolicus*, *Thermus islandicus*, *Deinococcus geothermalis*, *Thermosphaera aggregans*, Crenarchaeota archaeon, *Pyrococcus horikoshii*, *Aquifex aeolicus*, *Desulfotomaculum kuznetsovii*, *Caldanaerobacter subterraneus*, *Acidothermus cellulolyticus*, *Methanothermobacter thermautotrophicus*, *Thermobifida fusca*, *Thermotoga neapolitana*, *Petrotoga mobilis*, *Thermodesulfatator indicus*, *Thermus thermophilus*, *Bacteroides vulgatus*, and *Bacteroides fragilis*.

10. The method of claim 9, wherein the A6PE, the A6PP, or both the A6PE and the A6PP are thermostable or engineered to be thermostable.

11. The method of claim 9 further comprising converting glucose 6-phosphate (G6P) to F6P, catalyzed by a phosphoglucoisomerase.

12. The method of claim 11 further comprising converting glucose 1-phosphate (G1P) to G6P, catalyzed by a phosphoglucomutase.

13. The method of claim 12 further comprising converting a polymeric glucose carbohydrate to G1P, catalyzed by an α-glucan phosphorylase or a cellodextrin phosphorylase.

14. The method of claim 13 further comprising treating the polymeric glucose carbohydrate with a debranching enzyme.

15. The method of claim 9, wherein the microbial cells comprise bacterial cells.

16. A method for producing allulose, the method comprising:
   (i) converting fructose 6-phosphate (F6P) to allulose-6-phosphate (A6P), catalyzed by an allulose 6-phosphate epimerase (A6PE); and
   (ii) converting A6P to allulose, catalyzed by an allulose 6-phosphate phosphatase (A6PP), wherein:
      (a) the A6PE is selected from the group consisting of Thermobacterium *thermosaccharolyticum* A6PE, *Thermoanaerobacter brockii* A6PE, *Caldanaerobacter subterraneus* A6PE, *Deferribacter desulfuricans* A6PE, *Thermocrinis ruber* A6PE, *Hydrogenivirga* sp. 128-5-R1-1 A6PE, *Thermosipho atlanticus* A6PE, and *Thermosulfidibacter takaii* A6PE; and/or
      (b) the A6PP is selected from the group consisting of *Thermoanaerobacter wiegelii* A6PP, *Thermoanaerobacter ethanolicus* A6PP, *Thermus islandicus* A6PP, *Deinococcus geothermalis* A6PP, *Thermosphaera*

*aggregans* A6PP, Crenarchaeota archaeon A6PP, *Pyrococcus horikoshii* A6PP, *Aquifex aeolicus* A6PP, *Desulfotomaculum kuznetsovii* A6PP, *Caldanaerobacter subterraneus* A6PP, *Acidothermus cellulolyticus* A6PP, *Methanothermobacter thermautotrophicus* A6PP, *Thermobifida fusca* A6PP, *Thermotoga neapolitana* A6PP, *Petrotoga mobilis* A6PP, *Thermodesulfatator indicus* A6PP, *Thermus thermophilus* A6PP, *Bacteroides vulgatus* A6PP, and *Bacteroides fragilis* A6PP.

17. The method of claim 14, wherein the debranching enzyme is selected from isoamylases and pullulanases.

18. The method of claim 15, wherein the bacterial cells are *Escherichia coli* cells.

19. The method of claim 16, wherein:
(a) the A6PE is selected from the group consisting of Thermobacterium *thermosaccharolyticum* A6PE, *Thermoanaerobacter brockii* A6PE, *Caldanaerobacter subterraneus* A6PE, *Deferribacter desulfuricans* A6PE, *Thermocrinis ruber* A6PE, *Hydrogenivirga* sp. 128-5-R1-1 A6PE, *Thermosipho atlanticus* A6PE, and *Thermosulfidibacter takaii* A6PE; or
(b) the A6PP is selected from the group consisting of *Thermoanaerobacter wiegelii* A6PP, *Thermoanaerobacter ethanolicus* A6PP, *Thermus islandicus* A6PP, *Deinococcus geothermalis* A6PP, *Thermosphaera aggregans* A6PP, Crenarchaeota archaeon A6PP, *Pyrococcus horikoshii* A6PP, *Aquifex aeolicus* A6PP, *Desulfotomaculum kuznetsovii* A6PP, *Caldanaerobacter subterraneus* A6PP, *Acidothermus cellulolyticus* A6PP, *Methanothermobacter thermautotrophicus* A6PP, *Thermobifida fusca* A6PP, *Thermotoga neapolitana* A6PP, *Petrotoga mobilis* A6PP, *Thermodesulfatator indicus* A6PP, *Thermus thermophilus* A6PP, *Bacteroides vulgatus* A6PP, and *Bacteroides fragilis* A6PP.

20. The method of claim 16, wherein:
(a) the A6PE is selected from the group consisting of Thermobacterium *thermosaccharolyticum* A6PE, *Thermoanaerobacter brockii* A6PE, *Caldanaerobacter subterraneus* A6PE, *Deferribacter desulfuricans* A6PE, *Thermocrinis ruber* A6PE, *Hydrogenivirga* sp. 128-5-R1-1 A6PE, *Thermosipho atlanticus* A6PE, and *Thermosulfidibacter takaii* A6PE; and
(b) the A6PP is selected from the group consisting of *Thermoanaerobacter wiegelii* A6PP, *Thermoanaerobacter ethanolicus* A6PP, *Thermus islandicus* A6PP, *Deinococcus geothermalis* A6PP, *Thermosphaera aggregans* A6PP, Crenarchaeota archaeon A6PP, *Pyrococcus horikoshii* A6PP, *Aquifex aeolicus* A6PP, *Desulfotomaculum kuznetsovii* A6PP, *Caldanaerobacter subterraneus* A6PP, *Acidothermus cellulolyticus* A6PP, *Methanothermobacter thermautotrophicus* A6PP, *Thermobifida fusca* A6PP, *Thermotoga neapolitana* A6PP, *Petrotoga mobilis* A6PP, *Thermodesulfatator indicus* A6PP, *Thermus thermophilus* A6PP, *Bacteroides vulgatus* A6PP, and *Bacteroides fragilis* A6PP.

* * * * *

```
                           SEQUENCE LISTING

<160> NUMBER OF SEQ ID NOS: 10

<210> SEQ ID NO 1
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 1

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 2
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 2

Met Lys Gln Ser Thr Ile Ala Leu Ala Leu Leu Pro Leu Leu Phe Thr
1               5                   10                  15

Pro Val Thr Lys Ala
            20

<210> SEQ ID NO 3
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 3

Met Met Ile Thr Leu Arg Lys Leu Pro Leu Ala Val Ala Val Ala Ala
1               5                   10                  15

Gly Val Met Ser Ala Gln Ala Met Ala
            20                  25

<210> SEQ ID NO 4
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 4

Met Asn Lys Lys Val Leu Thr Leu Ser Ala Val Met Ala Ser Met Leu
1               5                   10                  15

Phe Gly Ala Ala Ala His Ala
            20

<210> SEQ ID NO 5
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 5
```

-continued

```
Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 6
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 6

Met Lys Lys Ile Trp Leu Ala Leu Ala Gly Leu Val Leu Ala Phe Ser
1               5                   10                  15

Ala Ser Ala

<210> SEQ ID NO 7
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 7

Met Met Thr Lys Ile Lys Leu Leu Met Leu Ile Ile Phe Tyr Leu Ile
1               5                   10                  15

Ile Ser Ala Ser Ala His Ala
            20

<210> SEQ ID NO 8
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 8

Met Lys Gln Ala Leu Arg Val Ala Phe Gly Phe Leu Ile Leu Trp Ala
1               5                   10                  15

Ser Val Leu His Ala
            20

<210> SEQ ID NO 9
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 9

Met Arg Val Leu Leu Phe Leu Leu Leu Ser Leu Phe Met Leu Pro Ala
1               5                   10                  15

Phe Ser

<210> SEQ ID NO 10
<211> LENGTH: 39
<212> TYPE: PRT
<213> ORGANISM: Artificial Sequence
<220> FEATURE:
<223> OTHER INFORMATION: Synthetic polypeptide

<400> SEQUENCE: 10

Met Ala Asn Asn Asp Leu Phe Gln Ala Ser Arg Arg Arg Phe Leu Ala
```

-continued

```
1               5                   10                  15
Gln Leu Gly Gly Leu Thr Val Ala Gly Met Leu Gly Pro Ser Leu Leu
            20                  25                  30
Thr Pro Arg Arg Ala Thr Ala
            35
```